US008227240B2

(12) United States Patent
Elson et al.

(10) Patent No.: US 8,227,240 B2
(45) Date of Patent: *Jul. 24, 2012

(54) SYSTEMS FOR SCREENING PHARMACEUTICAL CHEMICALS

(75) Inventors: Elliot Elson, University City, MO (US); William B. McConnaughey, St. Louis, MO (US); Tetsuro Wakatsuki, Milwaukee, WI (US)

(73) Assignee: The Washington University, St. Louis, MO (US)

( * ) Notice: Subject to any disclaimer, the term of this patent is extended or adjusted under 35 U.S.C. 154(b) by 833 days.

This patent is subject to a terminal disclaimer.

(21) Appl. No.: 11/774,393

(22) Filed: Jul. 6, 2007

(65) Prior Publication Data

US 2008/0038812 A1 Feb. 14, 2008

Related U.S. Application Data

(63) Continuation-in-part of application No. 10/219,097, filed on Aug. 14, 2002, now Pat. No. 7,449,306.

(60) Provisional application No. 60/806,690, filed on Jul. 6, 2006, provisional application No. 60/312,322, filed on Aug. 14, 2001.

(51) Int. Cl.
*C12M 1/34* (2006.01)

(52) U.S. Cl. ............... 435/287.1; 435/283.1; 435/289.1; 435/297.5

(58) Field of Classification Search ............... 435/283.1, 435/287.1, 289.1, 297.5; 623/13.17, 13.18, 623/14.12, 16.11, 20.17
See application file for complete search history.

(56) References Cited

U.S. PATENT DOCUMENTS

| 4,593,042 A | 6/1986 | Liang |
| 4,705,785 A | 11/1987 | Schwender et al. |
| 4,839,280 A | 6/1989 | Banes |
| 4,940,856 A | 7/1990 | Bock |
| 5,038,795 A | 8/1991 | Roush et al. |
| 5,326,357 A | 7/1994 | Kandel |
| 5,464,853 A | 11/1995 | Chan et al. |
| 5,571,083 A | 11/1996 | Lemelson |
| 5,665,391 A | 9/1997 | Lea |

(Continued)

FOREIGN PATENT DOCUMENTS

DE 19500498 7/1996

(Continued)

OTHER PUBLICATIONS

Eschenhagen, T. et al. "Transfection Studies using a new cardiac 3D gel system" Molecular Approaches to Heart Failure Thearpy. Editors: Hasenfuss, Gerd, Marban Eduardo. Publisher: Dr. Dietrich Steinkopff Verlag GMBH & Co. 2000 pp. 144-156.*

(Continued)

*Primary Examiner* — William H Beisner
*Assistant Examiner* — Michael Hobbs
(74) *Attorney, Agent, or Firm* — Michael Best & Friedrich LLP

(57) ABSTRACT

An apparatus for culturing a bio-artificial tissue including a multi-well plate and a scaffold is disclosed herein. Also disclosed is a tissue indentation system that includes a probe, an isometric force transducer, a computer and a computer-controlled motor. A tissue response system is provided and has a well including a scaffold with a bio-artificial tissue suspended on the scaffold and the tissue indentation system.

24 Claims, 35 Drawing Sheets

U.S. PATENT DOCUMENTS

| | | | | |
|---|---|---|---|---|
| 5,706,815 | A | 1/1998 | Sarvazyan et al. | |
| 5,843,766 | A | 12/1998 | Applegate et al. | |
| 6,197,575 | B1 * | 3/2001 | Griffith et al. | 435/288.4 |
| 6,332,364 | B1 | 12/2001 | Buschmann | |
| 6,881,584 | B1 | 4/2005 | Lenhard et al. | |
| 8,071,381 | B2 * | 12/2011 | Elson et al. | 435/383 |
| 2003/0064358 | A1 | 4/2003 | Elson et al. | |
| 2003/0091979 | A1 | 5/2003 | Eschenhagen | |
| 2006/0105357 | A1 | 5/2006 | Benesch et al. | |
| 2009/0068701 | A1 | 3/2009 | Elson et al. | |

FOREIGN PATENT DOCUMENTS

| | | |
|---|---|---|
| EP | 1250416 | 5/2006 |
| WO | 90/00595 | 1/1990 |
| WO | 98/38490 | 9/1998 |
| WO | 00/69355 | 11/2000 |
| WO | 01/11340 | 2/2001 |
| WO | WO 01/55297 | 8/2001 |
| WO | WO 03/016860 | 2/2003 |
| WO | 2005/039396 | 5/2005 |

OTHER PUBLICATIONS

Allen, F.D. et al., "Calpain regulated cell adhesion in EGF-stimulated fibroblast-populated-collagen-lattice contraction," BED (American Society of Mechanical Engineers), 50 (Proceedings of the Bioengineering Conference, Jun. 27-Jul. 1, 2001), 353-354.

Dewolf, C. et al., "Interaction of dystrophin fragments with model membranes," Biophys. J. (1997) 72:2599-2604.

Eschenhagen, T. et al., "Transfection studies using a new cardiac 3D gel system," Molecular Approaches to Heart Failure Therapy, Hasenfuss et al. eds., Verlag Gmbh & Co., Germany (2000) 144-156.

Eschenhagen, T. et al., "Three-dimensional reconstitution of embryonic cardiomyocytes in a collagen matrix: a new heart muscle model system," FASEB J. (1997) 11(8):683-694.

Fink, C. et al., "Chronic stretch of engineered heart tissue induces hypertrophy and functional improvement," FASEB J. (2000) 14(5):669-679.

Floyd Jr., S.S. et al., "Ex vivo gene transfer using adenovirus-mediated full-length dystrophin delivery to dystrophic muscles," Gene Therapy (1998) 5:19-30.

Kolodney, M.S. et al., "Correlation of myosin light chain phosphorylation with isometric contraction of fibroblasts," J. Biol. Chem. (1993) 268(32):23850-23855.

Kolodney, M.S. et al., "Isometric contraction by fibroblasts and endothelial cells in tissue culture: a quantitative study," J. Cell Biol. (1992) 117(1):73-82.

Pasternak, C. et al., "Mechanical function of dystrophin in muscle cells," J. Cell Biol. (1995) 128(3):355-361.

Paul, R.J. et al., "Effects of microtubule disruption on force, velocity, stiffness and [Ca2+] in porcine coronary arteries," Am. J. Physiol. Heart Circ. Physiol. (2000) 279:H2493-H2501.

Petersen, N.W. et al., "Dependence of locally measured cellular deformability on position on the cell, temperature, and cytochalasin B," Proc. Natl. Acad. Sci. USA (1982) 79:5327-5331.

Shen, X. et al., "Pharmacological modulation of the mechanical response of airway smooth muscle to length oscillation," J. Appl. Physiol. (1997) 83(3):739-745.

Sundberg, S.A., "High-throughput and ultra-high-throughput screening: solution- and cell-based approaches," Curr. Opin. Biotechnol. (2000) 11:47-53.

Wakatsuki, T. et al., "Phenotypic screening for pharmaceuticals using tissue constructs," Curr. Pharm. Biotech. (2004) 5(2):181-189.

Wakatsuki, T. et al, "Effects of cytochalasin D and latrunculin B on mechanical properties of cells," J. Cell Science (2001) 114(5):1025-1036.

Wakatsuki et al., "Cell mechanics studied by a reconsituted model tissue," Biophys. J. (2000) 79:2353-2368.

Website for Webster's Third International Dictionary, unabridged, www.lionreference.chadwyck.com, 6 pages; retrieved on Sep. 19, 2006.

Zahalak, G.I. et al., "Determination of cellular mechanical properties by cell poking, with an application to leukocytes," J. Biomech. Engin. (1990) 112:283-294.

Zimmerman, W.H. et al., "Three-dimensional engineered heart tissue from neonatal rat cardiac myocytes," Biotech. Bioeng. (2000) 68(1):106-114.

Canadian Patent Office Action for Application No. 2,497,343 dated Feb. 11, 2010 (3 pages).

European Patent Office Search Report for Application No. 02752832.2 dated Feb. 22, 2005 (3 pages).

European Patent Office Action for Application No. 02752832.2 dated Sep. 16, 2005 (4 pages).

European Patent Office Action for Application No. 02752832.2 dated Apr. 4, 2007 (4 pages).

European Patent Office Action for Application No. 02752832.2 dated Mar. 10, 2008 (4 pages).

European Patent Office Action for Application No. 02752832.2 dated Jul. 24, 2008 (5 pages).

European Patent Office Action for Application No. 08009189.5 dated Sep. 22, 2008 (8 pages).

European Patent Office Action for Application No. 08009189.5 dated Mar. 23, 2010 (4 pages).

Japanese Patent Office Action for Application No. 2003-521318 dated Mar. 17, 2009 (10 pages) with English translation.

Japanese Patent Office Action for Application No. 2003-521318 dated Jun. 10, 2008 (5 pages) with English translation.

Japanese Patent Office Action for Application No. 2003-521318 dated Apr. 6, 2010 (4 pages) English translation only.

United States Patent Office Action for U.S. Appl. No. 12/268,783 dated Sep. 2, 2010 (7 pages).

Bilsland, J. et al., "A rapid method for semi-quantitative analysis of neurite outgrowth from chick DRG explants using image analysis," J. Neurosci. Meth. (1999) 92:75-85.

Canadian Patent Office Action for Application No. 2,497,343 dated Nov. 23, 2011 (3 pages).

European Patent Office Action for Application No. 09759521.9 dated Oct. 6, 2011 (8 pages).

Takakuda, K. et al., "Strengthening of fibrous tissues under mechanical stimuli (in vitro experiments)," JSME Int. J. Ser. A. (1998) 41:576-583.

United States Office Action for U.S. Appl. No. 10/219,097 dated Dec. 14, 2005 (13 pages).

United States Office Action for U.S. Appl. No. 10/219,097 dated Sep. 29, 2006 (9 pages).

United States Office Action for U.S. Appl. No. 10/219,097 dated Oct. 9, 2007 (8 pages).

United States Office Action for U.S. Appl. No. 10/219,097 dated Apr. 8, 2008 (5 pages).

International Search Report for PCT/US02/25761 dated Apr. 21, 2003 (5 pages).

Written Opinion for PCT/US02/25761 dated Aug. 5, 2004 (6 pages).

International Preliminary Report on Patentability for PCT/US02/25761 dated Feb. 17, 2005 (6 pages).

* cited by examiner

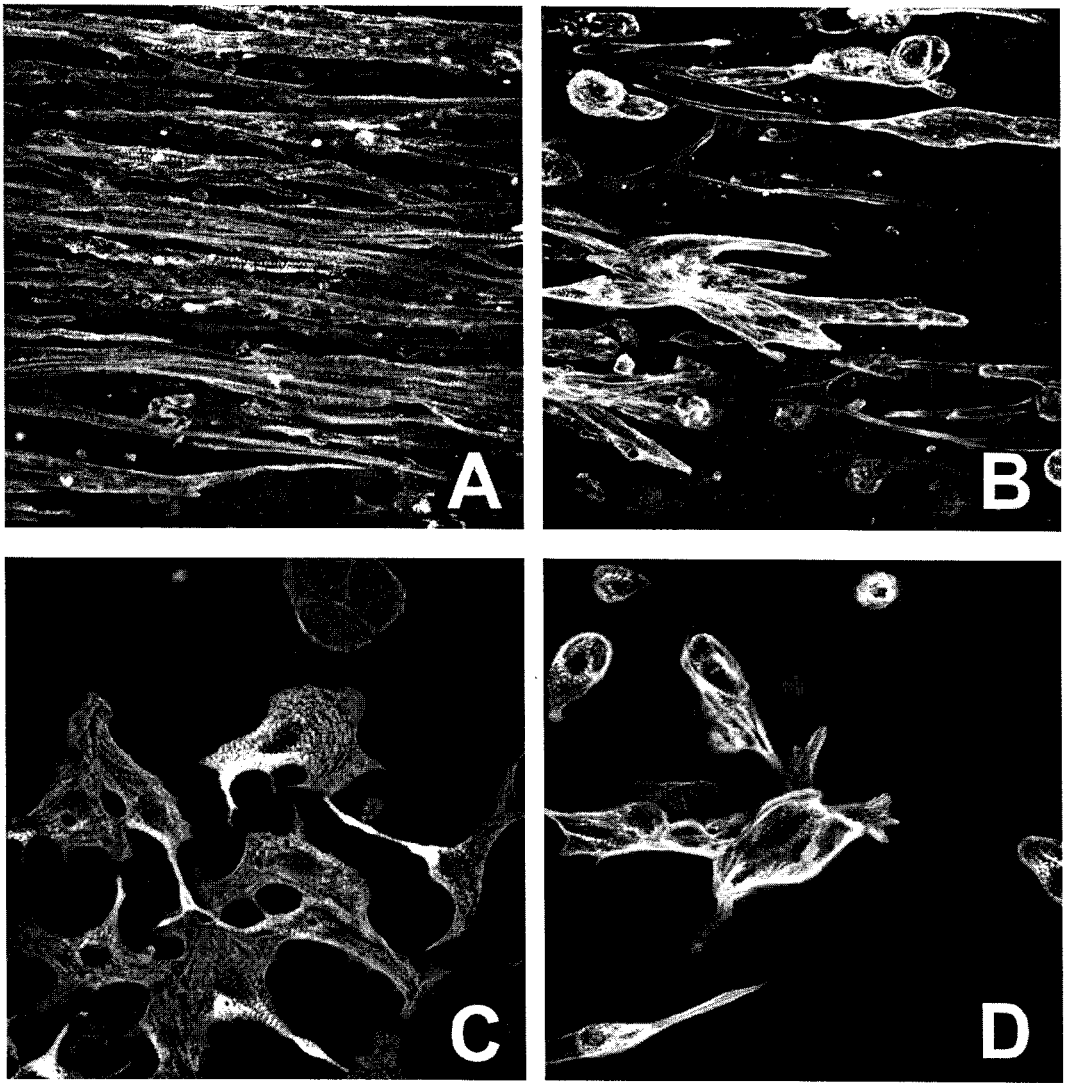

| Conditions | Contractility |
|---|---|
| DMEM supplemented with 10% FBS | No contraction |
| Cardiac Tissue Medium | Contraction after 7 to 8 days |
| Fibroblasts Conditioning Medium | Contraction after 4 to 5 days |
| Cocluture with Feeding Fibroblast Layer | Strong Contraction after 4 to 5 days |
| Coculture with Artificial Tissue with Fibroblasts | Strong Contraction after 4 to 5 days |
| Mixing Fibroblasts in the Tissue | Contraction after 4 to 5 days but reduction in contraction in 7 to 8 days |

FIG. 5

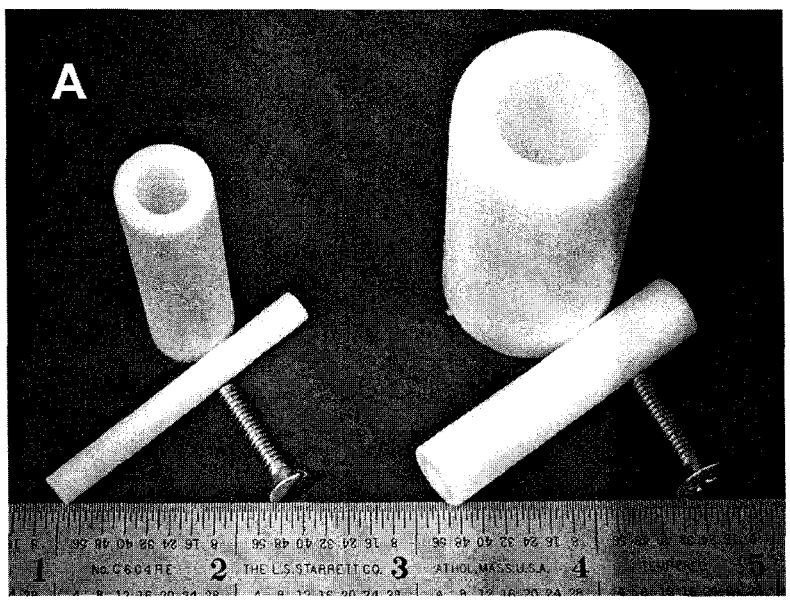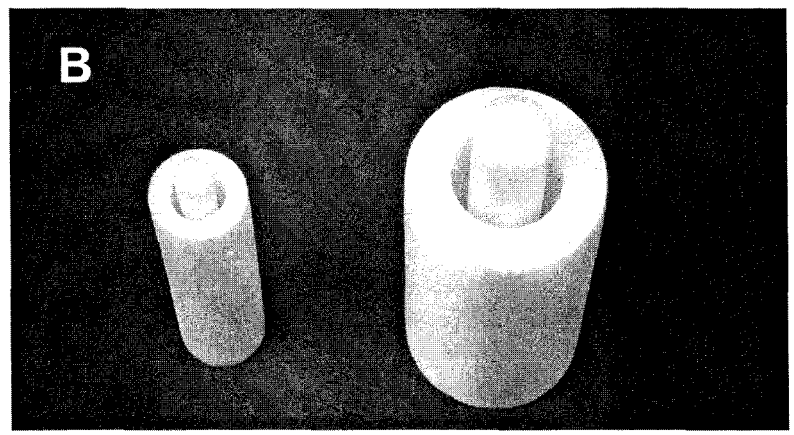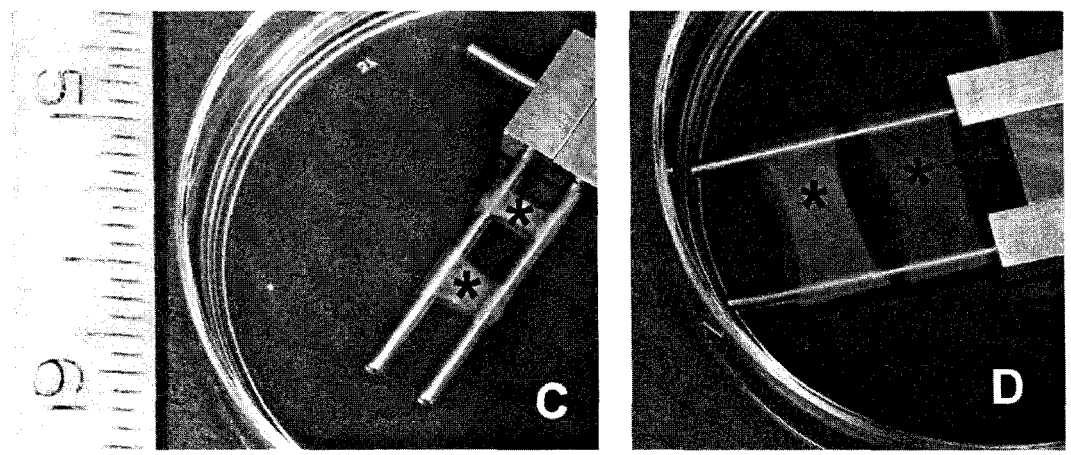
FIG. 8

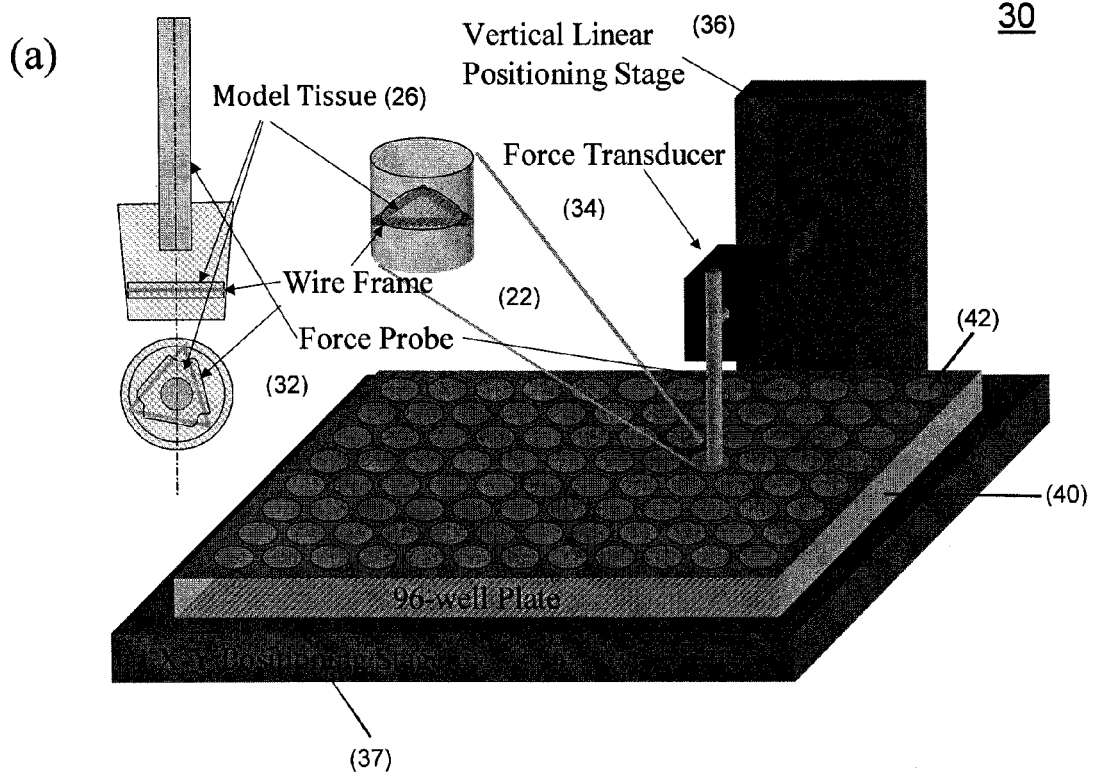
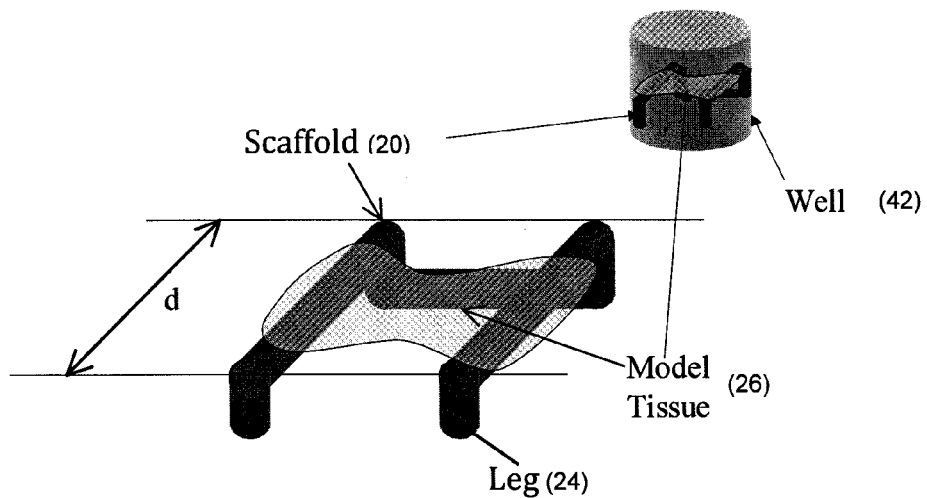
FIG. 11

Scaffold (20)
A.
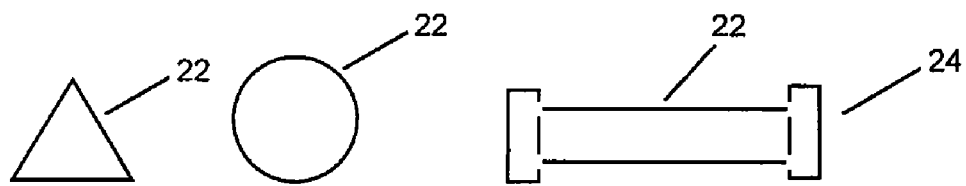
B.
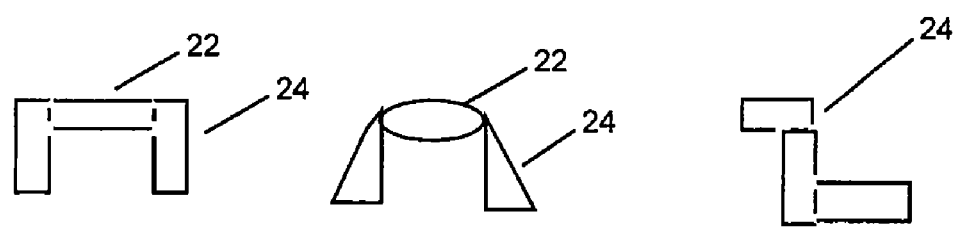
C.
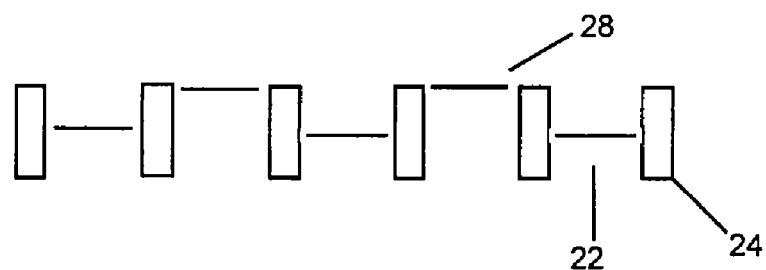
FIG 25

Prototype ver.beta1. 8 parallel force transducers indent mini-tissues in 96-well plates.
Insert: Close-up probes

SYSTEMS FOR SCREENING PHARMACEUTICAL CHEMICALS

CROSS-REFERENCE TO RELATED APPLICATIONS

This application claims priority to U.S. Provisional Application No. 60/806,690 filed on Jul. 6, 2006, which is incorporated by reference in its entirety. This application is a Continuation-in-part of U.S. patent application Ser. No. 10/219,097, filed Aug. 14, 2002, now U.S. Pat. No. 7,449,306, which claims priority to U.S. Provisional Application No. 60/312,322 filed Aug. 14, 2001, each of which are incorporated herein by reference in its entirety their entireties.

STATEMENT REGARDING FEDERALLY SPONSORED RESEARCH OR DEVELOPMENT

This invention was made with Government support under the terms of an STTR phase 1 grant from the National Institutes of Health, awarded as grant No. 1-R41 GM69072-01A1, and under the terms of an SBIR grant from the National Institute of Health, awarded as grant No. R41-AT003984-01. The Government has certain rights in this invention.

BACKGROUND OF THE INVENTION

This invention relates to systems and methods for screening pharmaceutical chemicals. More in particular, this invention relates to systems and methods for screening pharmaceutical chemicals in tissue models.

The number of pharmaceutical chemicals that must be tested for efficacy has increased enormously, mainly due to the development of large libraries of chemicals obtained using parallel and combinatorial chemical synthesis methods. Correspondingly, the number of identified therapeutic targets such as receptor and intracellular regulatory proteins has greatly increased since the application of functional genomics. Therefore, there is a great need for rapid and quantitative methods with which to screen pharmaceutical chemical(s) for their ability to elicit specific cellular responses and to identify leading pharmaceutical candidates.

Initial screening of large libraries of chemicals is carried out by testing for specific binding to target molecules using assay methods that operate in solution. High throughput methods have been developed based on scintillation proximity assay or fluorescence detection techniques (Sundberg, 2000). These methods, while readily adapted to screen thousands of compounds per day, provide information only about the strength and specificity of chemical interaction, not about cell responses. Hence, chemicals that are initially selected based on their ability to bind to a target in solution must be rescreened to assess their ability to elicit a desired cellular response. These secondary and tertiary levels of screening add increased expense and time to the process of detecting promising or lead pharmaceutical chemicals.

Stimulation of receptors and activation of ion channels have been assessed using fluorescence methods to detect changes in, e.g., calcium ion concentration, membrane potential and pH (Sundberg, 2000). These changes in ion concentration and transport often occur relatively early in the process of signal transduction and lead to more specific end responses such as the activation of specific enzymes. Hence, measurement of these responses does not necessarily provide information about the ultimate cellular responses that are activated or inhibited by a test pharmaceutical compound.

BRIEF SUMMARY OF THE INVENTION

The present invention provides an apparatus for culturing a bio-artificial tissue. The apparatus includes a multi-well plate with a plurality of wells. At least one of the wells includes a scaffold made of a non-porous material. The scaffold has at least one member with a cross-sectional diameter between about 100 µm and about 2.0 mm, and the member is disposed above the bottom of the well.

In another aspect, the invention provides a tissue indentation system which includes a probe for exerting a force on a test tissue; an isometric force transducer, which is operatively connected to the probe, for receiving a force signal from the probe; a computer which is operatively connected to the transducer, for processing the force signal into a signal corresponding to a tissue indentation; and a first computer-controlled motor which is operatively connected to the probe, for moving the probe relative to the test tissue.

In yet another aspect, the invention provides a tissue response system which includes a well with a scaffold and a bio-artificial tissue suspended on the scaffold. The well may be used for holding a test agent in contact with the tissue. Also included is a tissue indentation system which includes a probe for exerting an applied force on the tissue; an isometric force transducer which is operatively connected to the probe, for receiving a force signal corresponding to the applied force; a computer which is operatively connected to the transducer, for processing the force signal into a signal corresponding to a tissue response to the test agent; and a first computer-controlled motor which is operatively connected to the probe, for moving the probe relative to the tissue.

In another embodiment, the invention provides methods for obtaining a response of a multi-cell tissue model system to an agent which comprises contacting a tissue model with the agent and determining the cellular mechanical response to that contact of at least one of contractile force and tissue stiffness.

In yet another embodiment, a system is provided for obtaining a response of a tissue model system to an agent which comprises constructing a tissue model, contacting a test agent with the tissue model, and measuring cellular mechanical response to contact of the agent to the system of at least one of contractile force and hysteresis.

In a further embodiment, a system is provided for obtaining a mechanical response profile based on mechanical measurements of the response of reconstituted muscle and non-muscle tissue models to an agent, which comprises constructing a tissue model system having cells reconstituted in collagen and contacting the reconstituted cells with an agent. The mechanical response comprises at least one of contractile force and tissue stiffness.

In another aspect, the invention provides a method for screening pharmaceuticals, which comprises contacting a tissue model comprising reconstituted cells in collagen with an effective amount of a pharmaceutical chemical and measuring cellular response to the chemical in terms of at least one of contractile force or tissue stiffness.

In a further embodiment, the invention provides a method for managing a library of one or more pharmaceuticals or pharmaceutical chemicals which comprises obtaining a profile of a mechanical response to the contact of an agent with a tissue model, storing that profile in a database, storing at least one additional profile of another pharmaceutical in the database, setting up a means for comparing more than one profile with another profile, comparing the profile of a first pharmaceutical with a profile of a second pharmaceutical based on a pre-established or ordered standard/hierarchy of comparison and ranking the pharmaceuticals in an order of activity with respect to mechanical effect on a tissue model.

In a further embodiment, a method is provided for obtaining a multi-parameter mechanical response profile for a tissue model contacted with a pharmaceutical measuring the cellular response thereof.

In a further embodiment, a tissue model is provided, the tissue model comprises tissue assembled in the form of a ring mounted on a system comprising an isometric force transducer electrically coupled to a computer. The tissue model spans the isometric force transducer and a computer-controlled stepping motor provides an application of stretching and strain to the tissue.

In a further embodiment, a tissue model is provided wherein said tissue model comprises a membrane of reconstituted tissue supported by a frame. The mechanical properties of the membrane of reconstituted tissue are determined from resistance to stretching as the tissue is moved against a probe attached to an isometric force transducer.

In a further embodiment, a method is provided for preparing a tissue model, said method comprises placing self assembling tissue in a shape on a support, and subjecting said shaped tissue to an application of stretch by application of indentation.

In a further embodiment, a method is provided for establishing a mechanical response profile of a pharmaceutical which comprises contacting or relaxing a tissue model with a pharmaceutical and determining the mechanical response(s) of the tissue model in terms of at least one of contractile force and stiffness.

In another aspect, a method of culturing a cardiac tissue is provided using a medium(s) conditioned by a fibroblast(s).

In another aspect, this invention comprises a method to identify the effect of a drug upon a tissue which comprises treating a tissue using this invention and measuring the effect so resulting, and thereafter comparing such measured effect with a standard drug effect on the same or similar tissue.

In another aspect, this invention comprises a method to data mine a library of pharmaceutical moieties for activity in tissue, which comprises treating a tissue using this invention and measuring the effect so resulting. Optionally, the measured effect may be compared with a correspondingly measured effect of a standard drug on the same or similar tissue.

In another aspect, this invention comprises a method of optimizing tissue culture conditions for constructing implantable artificial cardiac tissue, with additional different factors influencing cardiac tissue development including growth factors, and matrix proteins and hormones to a tissue model of the invention.

BRIEF DESCRIPTION OF THE DRAWINGS

FIG. 1 illustrates an exemplary method of preparation and measurement overall.

FIG. 3a shows the change in force and dynamic stiffness in response to activation by fetal bovine serum. FIG. 3b shows the change in force and dynamic stiffness resulting from disruption of the actin cytoskeleton by 2 µM cytochalasin D (CD) FIG. 3c is a summary of the data from both 3a and 3b to show the overall (linear) dependence of dynamic stiffness on force.

FIGS. 4a and 4b show contractile force and stiffness, respectively, generated by the tissue models after treatment with various concentrations of CD. FIGS. 4c and 4d show contractile force and stiffness, respectively, generated by the tissue models after treatment with various concentrations of LA-B.

FIG. 5 shows the degrees of cardiac myocytes spreading in various tissue culture conditions. FIG. 5a shows well spread cardiac myocytes in a cardiac tissue model made in a conditioned medium prepared with cardiac fibroblasts. Cardiac myocytes cultured in Dulbecco's modified Eagle's medium (DMEM) with 10% fetal bovine serum, shown in FIG. 5b, do not spread well. Cardiac myocytes cultured on tissue culture dishes with and without conditioned medium are shown in FIGS. 5c and 5d, respectively. The supplemental table in the FIG. 5 shows spontaneous contractility of cardiac tissue models made with various culture conditions.

FIG. 8 shows photo images of regular and small size tissue molds and the tissue models. FIG. 8a shows disassembled small and regular size molds schematically shown in FIG. 1e. FIG. 8b shows assembled small and regular size molds schematically shown in FIG. 1c. FIG. 8c shows photo images of small size tissue models made using small size mold held by a spacer. FIG. 8d shows photo image of regular size tissue models held by the spacer schematically shown in FIG. 6.

FIG. 11a shows a high throughput system illustrating use of triangular and rectangular (alternative shape) frames shown in FIG. 11b, made of stainless steel wire about one millimeter in diameter, which provide scaffold supports on which reconstituted tissues form to provide samples from an indentation method of measuring tissue contractile force and stiffness.

FIG. 12(b) shows a plot of force verses indentation depth for the same data as for FIG. 12(a) including also the effect of adding 40 nM CD and 2 µM CD.

FIG. 17 shows the inhibition by different butane dione monoxime ("BDM") concentrations of a contractile response previously stimulated by 20% FBS. Panel a, b, c and d are treated with 2, 4, 20, and 40 .μM BDM, respectively.

FIG. 25 shows several views of the scaffold. FIG. 25a is a top elevation view of the scaffolds. FIG. 25b is a side elevation view of the scaffold. FIG. 25c is a side elevation view of one way of connecting several scaffolds to each other for ease of use in high throughput applications.

DETAILED DESCRIPTION OF THE INVENTION

Figure 1:
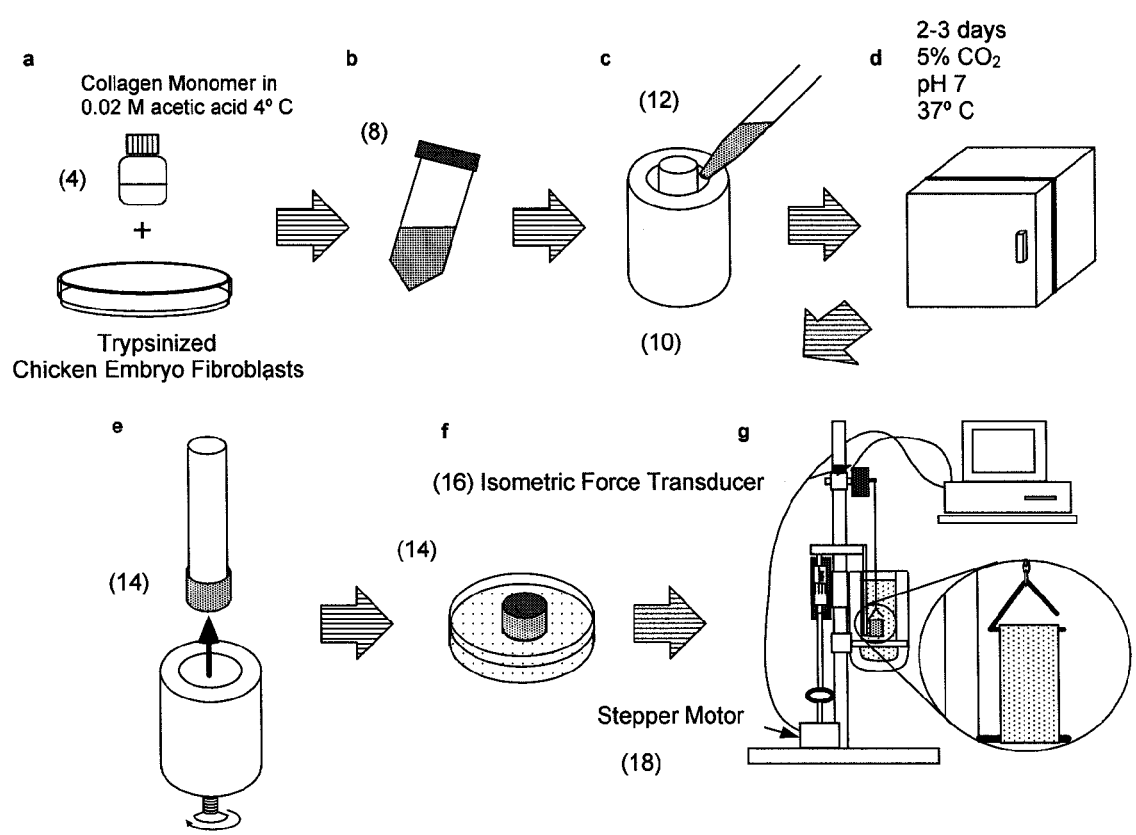
FIG. 1 is a schematic of an illustrative method for preparing and measuring fibroblast populated matrices (FPMs) (including live tissue models).

There are an estimated 20-30 trillion cells in the human body apportioned among tissues with distinct characteristics and functions. These cells include muscle and non-muscle cells. Muscle cells develop contractile force, and respond to nerve signals, which send out messengers, such as calcium ions and cyclic AMP that regulate the generation of contractile force. Non-muscle cells, e.g., fibroblasts and endothelial cells, respond to activators such as a polypeptide growth factor or hormones by generating contractile force.

Before any embodiments of the invention are explained in detail, it is to be understood that the invention is not limited in its application to the details of the structure and function of the invention set forth in the following description or illustrated in the appended figures of the drawing. The invention is capable of other embodiments and of being practiced or carried out in various ways. The use of terms such as "including," "comprising," or "having" and variations thereof is meant to encompass the item listed thereafter and equivalents thereof as well as additional items.

Unless otherwise noted, technical terms are used according to conventional usage. As used herein, however, the following definitions may be useful in aiding the skilled practitioner in understanding the invention:

As used herein the term "treated or contacted with" includes, but is not limited to exposed to, contacted with and placed in contact with. As used herein, the term "tissue model" includes, but is not limited to, reconstituted cells and tissues from living cells and extracellular matrix material. As used herein, the term "isometric force" includes, but is not limited to the force change without substantial change in the tissue length or tissue physical dimensions. As used herein the term "extracellular matrix (ECM)" includes, but is not limited to fibrin, fibronectin, laminin and similar constituents/components and synthetic materials such as polylactic acid and polyglycolic acid.

Tissue models such as the bio-artificial tissue models reconstituted from cells and extracellular matrix (ECM), simulate natural tissues. Such tissue models provide a polydisperse or monodisperse population of living cells in a uniform or substantially uniform collagenous matrix.

The mechanical properties of a tissue are influenced by the cells. Cytoskeletal and matrix proteins control the forces exerted by a tissue model and the stiffness of a tissue model. Cells regulate cystoskeletal structure and remodel ECM to produce mechanical changes during tissue development and wound healing. The disclosed system allows analysis of mechanical changes caused by both cytoskeletal and matrix proteins and allows differentiation of the various causes for mechanical changes.

Contractile forces result from activation of non-muscle myosin. The increase of contractile force over time after activation can be measured in tissues reconstituted from muscle and non-muscle cells. Such cell responses can lead to reorganization of the cytoskeleton within the cells of the extracellular matrix (ECM) in which the cells are embedded. The development of contractile forces and the mechanical effects of cytoskeletal and matrix reorganization provide indicators of cellular response to a candidate pharmaceutical(s). Changes in contractile forces and stiffness result from activation or deactivation of cellular myosin, from other cytoskeletal perturbations, or from perturbations of the extracellular matrix within which the cells are embedded.

Use of reconstituted tissue permits assembly of tissue models, which may be generated using specifically isolated cell types or with combinations of cell types. Hence, responses of reconstituted tissues to a candidate pharmaceutical provide mechanical measurements for these cell types without complicating contributions of other cell types normally present in natural tissues. An association is established between a specific cell type and a profile of changes in mechanical responses, such as force and stiffness, which result when the cells are contacted by an agent.

Contractile force and tissue stiffness change due to contraction and relaxation of the cells within the reconstituted tissue upon effective contact with an agent. As used herein the term "agent" includes, but is not limited to, one or more candidate pharmaceuticals, which may or may not have any pharmaceutical activity or cellular response. Agents include chemicals, toxins, pathogens (such as viruses or bacteria) and physical trauma (such as tearing or starvation). Agents also include, but are not limited to, activators, antagonists and the like. As used herein, the term "effective contact" means placing an effective amount of an activator in contact with the tissue model, for example, as by adding an agent to a tissue model. As used herein, the term "pharmaceutical" means having to do with medicine, which affects an animal or a person. Pharmaceuticals include, but are not limited to, chemicals, peptides and nucleic acids.

Cells may be suitably obtained from a variety of tissue sources so that the tissue models used in the methods in accordance with the present invention provide tissue-specific information regarding responses to candidate pharmaceutical(s).

As used herein, the term "tissue stiffness" is the force required to stretch tissue by a defined amount. In other words, tissue stiffness is the ratio of force applied to the tissue to the extent of stretch of the tissue. The force required to stretch an elastic object increases as the extent of stretching of the object (the "strain") increases. Biological tissues, however, are viscoelastic. That is, viscous forces that depend on the rate of stretching also contribute to resistance to stretch. Measurements of the contribution of viscous forces may be determined from the dependence of the stiffness on the rate of stretching. For linearly elastic materials, the force increases linearly with strain, i.e. stiffness is constant, independent of strain. Biological tissues and reconstituted tissue models are mechanically nonlinear and tissue stiffness increases with strain. Over a range of forces, the stiffness varies linearly with the force either generated within the tissue or externally applied to it. This linear variation indicates that the force is an exponential function of strain.

One method of measuring tissue stiffness includes subjecting the tissue in a tissue model system to a relatively large steady stretch and observing the change in force as the strain increases. Such measurements of tissue stiffness enable measurements and determinations of parameters including hysteresis (area), phase lag and dynamic stiffness.

Once a preset strain is achieved during the measurement of tissue stiffness, the extent of stretching (strain) can then be reduced at the same rate in a return to the tissue's initial strain and stiffness values. A plot of force as a function of strain as strain decreases (unloading curve) is always at lower force levels than during the increase of strain (loading curve). The area enclosed by the aforementioned two curves is the hysteresis area, which is an indicator of tissue viscosity. The hysteresis area measures a loss of energy in the tissue during the respective loading-unloading cycle.

Another method of measuring tissue stiffness uses oscillatory stretch, i.e., periodic increases and decreases of strain at a defined frequency (e.g. sinusoidal) selected by an experimenter. The force increases and decreases correspondingly at the same frequency, but possibly with a shift in phase, i.e. a phase lag. The phase shift or phase lag is another indicator of the viscosity of the tissue models. The type of tissue stiffness measured by oscillatory stretch is "dynamic stiffness". Dynamic stiffness depends on the magnitude of the stretch (because tissue models are nonlinear) and on the frequency of oscillation because the tissues are effectively viscous.

In illustrative embodiments of this invention, mechanical measurements are carried out on reconstituted tissue models. The invention provides a method of quantitatively characterizing mechanical properties of connective tissue models, such as fibroblast-populated matrices (FPM's), via uniaxial stretch measurements in response to contact with one or more activators.

The connective tissue models, which are composites of selected living cells and ECM (i.e. a bio-artificial system), usually Type I collagen, respond by stiffening due to contact with activators which activate contractile forces. In one embodiment illustrative of a tissue model system of this invention, the tissue is assembled in the form of a ring that is mounted on a system in which the tissue spans an isometric force transducer and a computer-controlled stepping motor for measurements of contractile force and strain.

In another embodiment suitable for high throughput screening, tissue stiffening is measured by an indentation method using a multi-well plate system. In the indentation method, contractile force is measured (as peak force) along with tissue stiffness, which is registered as a resistance to indentation of the tissue model by a probe contacting the tissue model. The probe is attached to a force transducer. Many tissue composites can be rapidly tested (high throughput) for their mechanical responses to agents in this embodiment. The system is suitably adapted in size and design to use small amounts of tissue model and reagents.

The system described may be used to test a variety of agents. For example, agents may be screened for their ability to activate a contractile response. Candidate pharmaceuticals that inhibit a contractile response can be screened for their ability to prevent such a response evoked by a well-characterized activating agent. Moreover, candidate pharmaceuticals that cause cells to remodel the collagen, thereby stiffening or softening the collagen, can be tested using the methods disclosed herein.

A system and method for characterizing and profiling the mechanical response(s) of reconstituted tissue models to contact with one or more agents is provided. Rapid and quantitative screening of many potential activators or inhibitors of cell contraction, cytoskeletal change, cell-matrix interactions, and matrix remodeling are possible. The methods described herein provide a quantitative readout of changes in tissue stiffness, which can be calibrated to supply corresponding quantitative data on the extent of activation or inhibition of myosin modulation of cytoskeleton components or of interaction between the cell and matrix or properties of the matrix itself.

The systems and methods described herein are not limited to the specific embodiments exemplified. In addition, components of each system and each method can be practiced independently and separately from other components and methods described herein. Each component and method can be used in combination with other components and other methods.

Collagens useful in formation of bio-artificial tissues include collagen Classes 1-4 which include all Types I-XIII and combinations thereof. Various types of extracellular matrix may also be in formation of bio-artificial tissues, such as Matrigel®.

Reconstituted tissue models can be used to assess quantitatively and rapidly the effects of many different classes of potential pharmaceuticals, toxins, and pathogens as agent(s) on the mechanical properties of cells and matrix. These mechanical properties provide general indicators of the overall organization of cellular mechanical systems, especially the cytoskeleton, of the operation of signal transduction pathways, and of the organization imposed on the matrix by the cells during tissue development. Therefore they provide potential applications in a wide range of disease areas.

Agents useful as activators include, but are not limited to, fetal bovine serum (FBS), lysophosphatidic Acid (LPA); thrombin, growth factors including epidermal growth factor (EGF), platelet derived growth factor (PDGF), angotensin-II, endothelin-1, vasopressin and combinations thereof. As used herein, the term "agonist" includes a chemical substance that activates a cellular response.

Inhibitors include, but are not limited to, inhibitors which bind cell surface receptors including a receptor antagonist for angiotensin II receptor and also inhibitors that act within the cell. Inhibitors useful herein include, but are not limited to, those which inhibit signal transduction pathways including genistein, herbimycin and agents which act on the cytoskeleton. These include, but are not limited to, cytochalasin D, latrunclin B, paclitoxol, nocodazole, calyculin A, butane-dione-monoxime (BDM) and combinations thereof.

The amount of agent(s) provided to the reconstituted cell is an amount effective to elicit a response from or by a tissue model. An effective amount is generally between about 1 nM to 100 mM. suitably 100 nM to 1 mM, more suitably 500 nM to 500 µM.

There are several mechanical parameters which may be determined using the disclosed system and methods, as follows:

Ring Type System:

| | |
|---|---|
| Baseline force | Force measured at 0 strain (no stretch). |
| Dynamic stiffness | Amplitude of force response to the sinusoidal stretch divided by amplitude of applied oscillatory strain. The measurements are taken at various strain levels. Dynamic stiffness can also be obtained during a ramp stretch. |
| Phase angle | Phase angle indicates time dependent viscosity of a sample. It is obtained by the angle of phase delayed between force response and sinusoidal driving function. The measurements are normally taken at 0 strain but can be measured at various strains as long as the mean force level reaches a steady state for a short period of time. |
| *Storage modulus, G" | In-phase component stress (force divided by cross G' sectional area of sample) in response to a sinusoidal stretch divided by the strain. |
| *Loss modulus, G" | Out-of-phase component stress in response to a G" sinusoidal stretch divided by the strain. |
| Peak force | Peak force in response to a ramp stretch. |
| Hysteresis curve area | Hysteresis curve is a plot of force response to a area ramp stretch plotted against strain. Force response during the sample elongation is always higher than that during the sample shortening. The area enclosed by the two lines is related to the viscosity of the sample. |

Tissue Indentation Procedure:

| | |
|---|---|
| Peak force | Peak force in response to tissue indentation. |
| Hysteresis curve, area | Hysteresis curve is a plot of force response to a area tissue indentation. Force response during the indentation (loading) is always higher than that during the retraction (unloading). The area enclosed by the two curves is related to the viscosity of the sample. |

*G' and G" can be calculated from dynamic stiffness and phase angle by knowing the cross sectional area of samples. G' and G" are parameters indicating the mechanical properties of samples independent of their sizes and shapes.

There are suitably many additional utilities in accordance with the present invention. For guiding treatment of cardiac diseases, reconstituted tissue models assembled from cardiac myocytes and/or cardiac fibroblasts can be used to test the effects of candidate pharmaceuticals on cell and matrix remodeling processes that result from pressure overload and on tissue restructuring that occurs in response to trauma or infarction. Additionally, the methods and systems of the present invention can be employed to guide treatment of dental connective tissue diseases, cancer metastasis (contraction, traction force in cell motility), diabetes (stiffening of connective tissues and skin by collagen cross linking), pulmonary diseases such as emphysema, chronic inflammation (elastase secreted from neutrophils), muscular dystrophy and aging skin.

The present invention also comprises a method of managing a library of pharmaceuticals. This method comprises obtaining a profile of mechanical response to the contact of an agent with a tissue model system wherein a tissue model has been contacted with the pharmaceutical, storing that profile in a database, storing at least one additional profile of another pharmaceutical in a tissue model system in that database, setting up a means for comparing at least two profiles, comparing the profile of the first pharmaceutical with the profile of a second pharmaceutical based on a pre-established or ordered standard of comparison. The pharmaceuticals are ranked in an order of activity with respect to mechanical effect on the tissue model system based on their respective profile.

More details are set forth below regarding FIGS. 1-35. Although specific exemplary embodiments of methods and systems for using tissue models are described herein, the methods and systems are not limited to such specific exemplary embodiments.

FIG. 1 is an illustrative schematic of a ring method for preparing and measuring FPM's (illustratively shaped as a ring). In one embodiment, chicken embryo fibroblasts (CEF's) (2) and monomeric collagen (4) are mixed in DMEM (6) at pH 7 to form a suspension (8). This suspension (8) is poured into casting wells (10) having a mandrel (12) and polymerized at 37° C. The casting wells (10) are incubated for a day or more during which time the cells compress and remodel the polymerized collagen matrix. After incubation the mandrel (12) is removed from the casting well (10) and the FPM-ring (14) is removed gently from the mandrel (12). The FPM-ring (14) is connected to the force measuring apparatus (an isometric force transducer) (16) and a stepper motor (18) that controls and sets the tissue strain.

Figure 2:
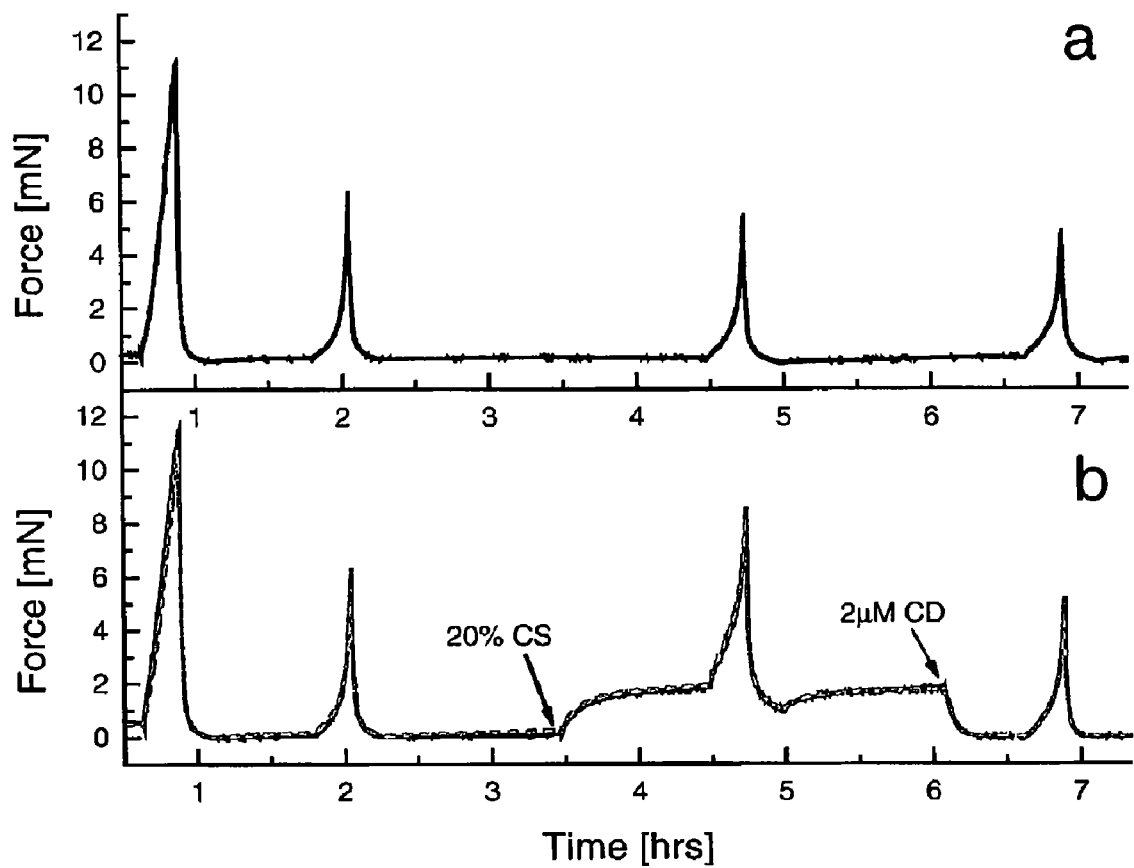
FIG. 2 illustrates a force response to stretch from a tissue model and illustrates a profile obtained from a sequence of four stretch cycles applied to one FPM plotted over time. Profile a of FIG. 2 illustrates a substantially larger peak force for a first stretch than for subsequent cycles. Profile b of FIG. 2 illustrates the excellent reproducibility of the measurements by showing force responses of measurements carried out on two FPM's.

FIG. 2 depicts a force response to stretch of a FPM. Force responses from a sequence of four stretch cycles applied to one FPM were traced over time. The first stretch cycle (as shown in panel a) produces a substantially larger peak force than subsequent cycles. A much smaller (~6%) reduction in peak force is seen in each of the subsequent cycles (panel a). Panel b of FIG. 2 illustrates the reproducibility of the measurement by showing stretch sequences form two FPM's. (solid line and gray broken line). The effects of treatment by both 20% calf serum (increase in contractility) and 2 uM Cytochalasin D (abolition of active contractility of the tissue) are almost identical in the two samples. The cycle time was set to 30 minutes instead of the previously used 60 minutes cycle time for this test to accommodate additional test manipulations. (The force-strain and stiffness-strain curves from the 30 and the 60 minute cycle times, however, are almost identical.)

Figure 3:
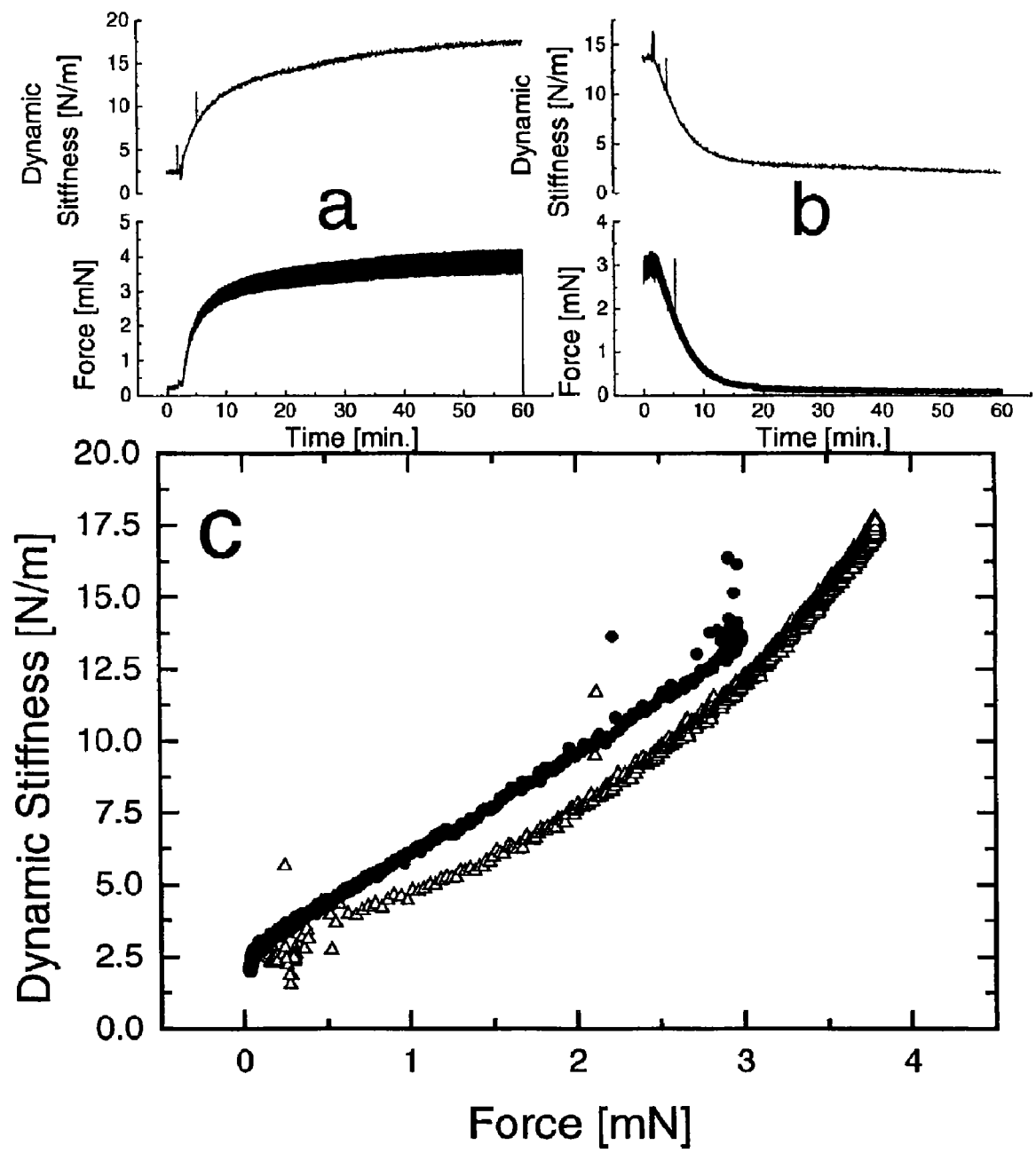
FIG. 3 is a graph which displays tissue stiffness as a function of cell generated force.

FIG. 3 compares tissue stiffness to cell-generated force. In this test, the tissue model was stretched sinusoidally by 0.3% at 1 Herz. The stiffness was measured as the peak-to-peak change in the force (approximated by the breadth of the trace at this time scale). Each stiffness point represents the average stiffness for 5 seconds.

FIG. 3, graph (A) shows that stiffness changes with a magnitude and time course similar to force during FBS (5%) stimulation. FIG. 3, graph (B) shows actin filament disruption by Cytochalasin D (2 μM). As in FIG. 3 (A) stiffness changes correspond to force changes.

FIG. 3, graph (C) shows stiffness plotted against force for measurement data shown in FIG. 3 parts (A) and (B). The force-stiffness relation for the rise in force after FBS (closed circles) is very similar to the force-stiffness relationship for the decline in force after addition of Cytochalasin D (open triangles). Each circle point and triangle point of this figure represents both force and stiffness. Stiffness increases approximately linearly with force.

Figure 4:
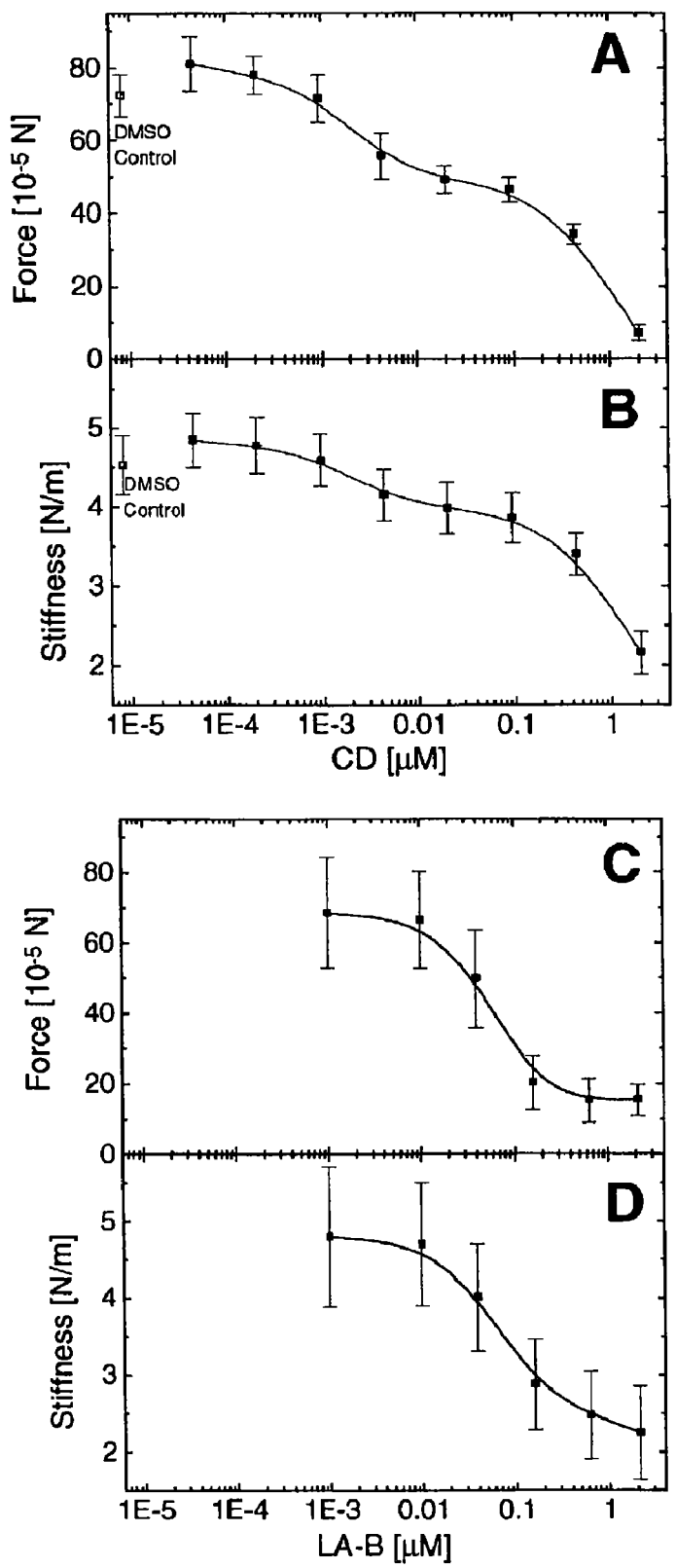
FIG. 4 displays a dependence of contractile force and dynamic stiffness on CD and Latrunculin B (LA-B, Calbiochem-Novabiochem Corporation, San Diego, Calif.) concentrations.

FIG. 4 illustrates the dependence of force and dynamic stiffness on CD and LA-B concentrations. The force and dynamic stiffness were significantly diminished at a CD concentration of 2 nM and continued to fall as the CD concentration was increased (A, B). In contrast, for LA-B the force and dynamic stiffness began to diminish only when the concentration reached 40 nM, and reached their minimum values at a concentration of ~600 nM (C, D). This figure illustrates the sensitivity of the measurement method, which can detect force and stiffness changes at low concentrations of CD that cause no changes in the actin cytoskeleton detectable by light microscopy.

Figure 10:
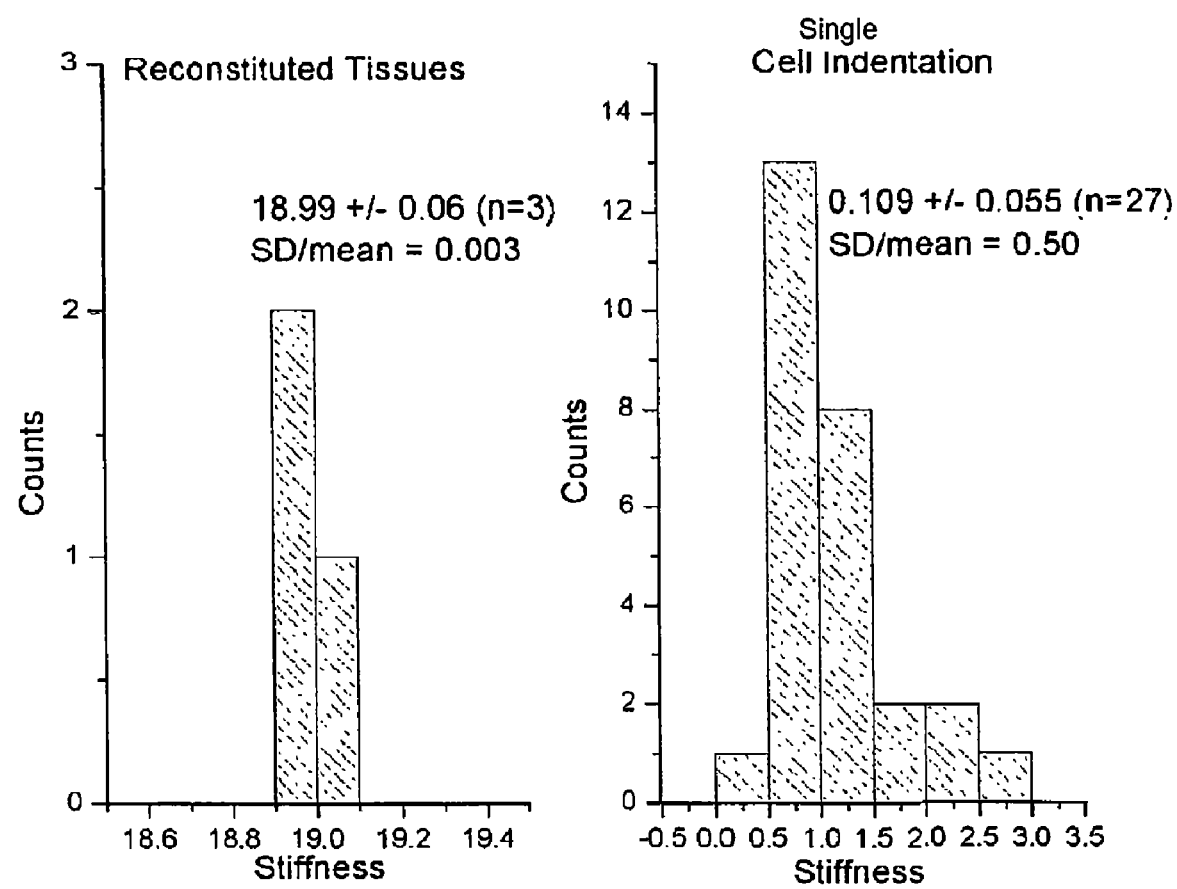
FIG. 10 is a comparison of data variance for measurements of tissue stiffness using the reconstituted tissue ring method (left side) and a single cell indentation method (right side).

FIG. 10 illustrates a comparison of data variance in tissue model stiffness measured using reconstituted tissues with a ring method (left bar graph) and in cell stiffness measured by indentation of individual cells (right bar graph). Fewer measurements are required to obtain statistically significant data using tissue models than using single cells. This is because, even in a cultured population of cells of a single type, there is substantial cell-to-cell variation for many experimental parameters. Hence, measurements on many individual cells must be averaged to characterize the population. Therefore high throughput screening devices that measure the biological activity of chemical compounds on single cells require many measurements to obtain statistically significant data. Since the tissue models tested contained at least 10,000 cells, each measurement represents an average of many cells in the tissue. Therefore, the efficiency of high throughput screening on tissue models is improved over that on single cells. (See Pertersen et al. 1982, Zahalak et al. 1990). For example, stiffness of the reconstituted tissues was measured with statistical significance after ten-fold fewer measurements using the ring system than are required for cell indentation measurements on individual cells (FIG. 10).

Many signal transduction pathways contribute to the mechanical properties of reconstituted tissues by regulating contractile force, the organization of the cytoskeleton, and the integrity of the extracellular matrix. Therefore, a wide range of intracellular and extracellular target molecules can be assayed by determining their effects on the mechanical properties of reconstituted tissues using this invention.

The cells in the reconstituted tissue models of the present invention are in an environment that resembles their condition in natural tissues and organs. Therefore, results of the assays using this method yield results similar to those obtained using animal models. Some of the animal testing can be replaced by using tissue models. For example, some tests of agents acting on skin can be conducted using artificial living tissues.

The methods in accordance with the present invention also may be used to detect the effects of toxic materials on the mechanical properties of reconstituted tissues. For example, the inventors discovered that a 10% solution of ethanol reduces force and stiffness of tissue models significantly. The inventors observed that infection of cells in tissue models by viruses can diminish force and stiffness. Therefore, the methods can be utilized to determine the toxicological effects of substances and biological materials.

FIG. 11 illustrates an exemplary high throughput screening system utilizing an indentation method for measuring the mechanical response of a tissue system.

A frame, generally designated as reference numeral (22), e.g., a triangular frame, made of stainless steel wire provides a scaffold (20) on which reconstituted tissue (26) forms in the Examples. In this illustration, the wells (42) are slightly tapered toward the bottom and the frame is securely positioned about 1 mm above the bottom of the well. The non-polymerized solution of collagen containing cells and appropriate cell culture media as described is poured into the wells, filling them to a level 3 mm above the bottom (FIG. 11a). The 96-well plate (40) may be incubated at 37° C. with 5% $CO_2$. During incubation, the cells self-assemble into a bio-artificial tissue and compress the collagen matrix by squeezing out liquid thereby reducing the total volume by about ten fold.

Without the scaffold or wire frame, the reconstituted tissue contracted into a small sphere floating in the tissue culture medium. The collagen matrix can be compressed into different shapes using different frame shapes such as a circle or rectangle as depicted in FIG. 25. One of skill in the art will appreciate that a wide array of shapes could be used. Other wire frame shapes, such as those shown in FIG. 11*b* and FIG. 25, produced tissue strips with different widths and shapes. Any shape frame (22) can be used to form a scaffold (20), including but not limited to, circular, rectangular, triangular, pentagonal, hexagonal, or other higher order polygons. The scaffold may also be formed of more than one member. For example, the scaffold (22) could be formed of two parallel members spaced apart with or without one or more perpendicular member connecting them (FIG. 11*b* and FIG. 25).

The scaffolds are suitably made of any non-porous, biocompatible material, such as metal, nonmetal, or plastic. In the Examples, the scaffold was made of stainless steel. One of skill in the art will appreciate that other materials including, but not limited to, glass, polypropylene or polystyrene may also be suitably used to produce the scaffold.

In accordance with the present invention, cells self-assemble to form a tissue model conforming to the shape of the scaffold or support. In forming, the tissue overlays the members of the scaffold, spanning the space between the members. For example, on a triangular wire frame, the cells form a membrane spanning among the three edges, which is illustrated in FIG. 11*a*. The scaffold or wire frame in the Examples was about 1 mm in diameter, but frames may suitably have smaller or larger cross-sectional diameters. Suitably, the scaffold is made up of one or more members with cross-sectional diameters between about 100 µm and about 2 mm. The frame is comprised of generally cylindrical or tubular members that allow the tissue to form around the members such that the tissue overlays the members. The members comprising the frame are suitably somewhat rounded to minimize ripping of the tissue when force is applied. For example, members with a rectangular cross-section could be utilized if the edges were rounded such that the tissue did not tear when force was applied. The members are suitably made of a non-porous material and have a cross-sectional diameter of less than about 2 mm, suitably about 1 mm.

The bio-artificial tissue forms a membrane structure spanning a horizontal cross-sectional space between or across the members comprising the frame. The horizontal cross-sectional space the bio-artificial tissue spans is suitably larger than 10 µm, but can be as large as the well (42) allows, suitably the tissue spans a space between about 100 µm and about 5 mm, more suitably between 1 mm and 4 mm. A typical bio-artificial tissue depicted in FIG. 29C-E is approximately 4×4×0.8 mm and formed in a 8×8 square chamber. (The shape of chamber was modified for viewing the sample. The ET was fixed with formaldehyde (10%) and stained with orange dye for clear viewing).

The frame (22) is suitably supported above the bottom (43) of the well (42). The frame (22) may be supported by the side of the well by using tissue culture plates with tapered wells. Alternatively, the frame may be supported above the bottom of the well by using specially designed plates with built-in scaffolds attached to the side of the well or with wells having ledges on which the frame rests. In another alternative embodiment, the scaffold may include a frame with at least one leg (24) attached to the frame (22) to support the frame above the bottom of the well. The number of legs (24) required to support the frame will vary depending on the shape of the frame. FIG. 11*b* depicts a scaffold with 4 legs, but scaffolds may be designed with fewer or more legs as depicted in FIG. 25. The legs (24) may be used to support the frames (22) by projecting down from the frame and touching the bottom of the well (42) or the legs (24) may project upwards from the frame (22) and support the frame of the scaffold (20) by anchoring the scaffold to the top (45) of the well (42). For example, the leg (24) may have a small hook structure at the end that allows the scaffold (20) to hang from the top of the well (FIG. 25(*b*)). Although the frame (22) of the scaffold is supported above the bottom of the well, the exact distance is not critical as long as the tissue can be bathed in media. Suitably, the scaffold is at least about 0.5 mm above the bottom of the well, more suitably the scaffold is at least about 1.0 mm above the bottom of the well.

FIG. 29B depicts a prototype multi-well plate (4) comprising scaffolds (20). The 8-well plate was machined from a polycarbonate bar (25×60×10 mm) using a tabletop CNC mill (Sherline Products Inc., Vista, Calif.). The 8 square wells (42) of 8×8 mm contained 2 stainless steel bars (22) (1 mm diameter). The centers of the stainless steel bars were located 2 mm above the bottom of the well and 2 mm from the side of the well such that the 2 bars were 4 mm apart. A microscope coverslip (No. 1 thickness, Fisherbrand) was used to seal the bottom of each well using silicon glue (Dow Chemical Co., Midland, Mich.) to facilitate microscopic imaging.

For ease of use in a high throughput system using a multi-well plate format, the scaffolds (20) may be joined together by a connector (28) in groups including but not limited to, 2, 4, 8, 12 or 96 scaffolds as depicted in FIG. 25C. By joining scaffolds (20) together in groups, the scaffolds can be readily positioned in a multi-well plate (40). The connectors (28) may be made to be readily separable, e.g., such that a quick tugging motion will break the connection and allow the user to customize the number of scaffolds used. The scaffolds and bio-artificial tissue system described herein may also be adopted for use by one of skill in the art in any multi-well plate, including but not limited to, 6 well, 8 well, 12 well, 24 well, 48 well, 192 well or 384 well plates.

As seen in the Examples below, a porous support material, or other fastener, such as a Velcro fastener, was not needed to facilitate tissue adhesion even to the non-porous stainless steel surfaces of the wire frame used. The collagen was compressed to a greater extent at the outer portion of the membrane or tissue strip and allowed the tissue to be suspended on the scaffold without the need for a fastener. Therefore, this outer portion of the membrane can withstand the stress produced by the cells and prevents ripping the bio-artificial tissue off from the wire frame.

FIG. 11*a*, FIG. 26, FIG. 27 and FIG. 29 contain depictions of high throughput tissue indentation apparatus. In FIG. 11*a*, a single probe (32) is operatively connected to an isometric force transducer (34) and the force transducer (34) is operatively connected to a vertical linear positioning stage (36) that may be operatively connected to a stepper motor that drives the movement of the probe (32) and applies force to the bio-artificial tissue (26). The stepper motor may be controlled by a computer and the voltage signal from the isometric force transducer (34) may be translated into a digital signal for data recording. The multi-well plate (40) is moved horizontally by an X-Y positioning stage (37) that may be operatively connected to a second motor to control in which well (42) the probe (32) is contacting the tissue (26). In an alternative embodiment, a second motor controls movement of the probe in only a single horizontal direction, e.g., the Y direction, and an operator moves the probe in the second horizontal direction, e.g., the X direction. In yet another alternative embodiment, a second motor controls movement of the probe in one horizontal direction, e.g., the Y direction, and a third motor moves the probe in the second horizontal direction, e.g., the X direction.

Figure 26:
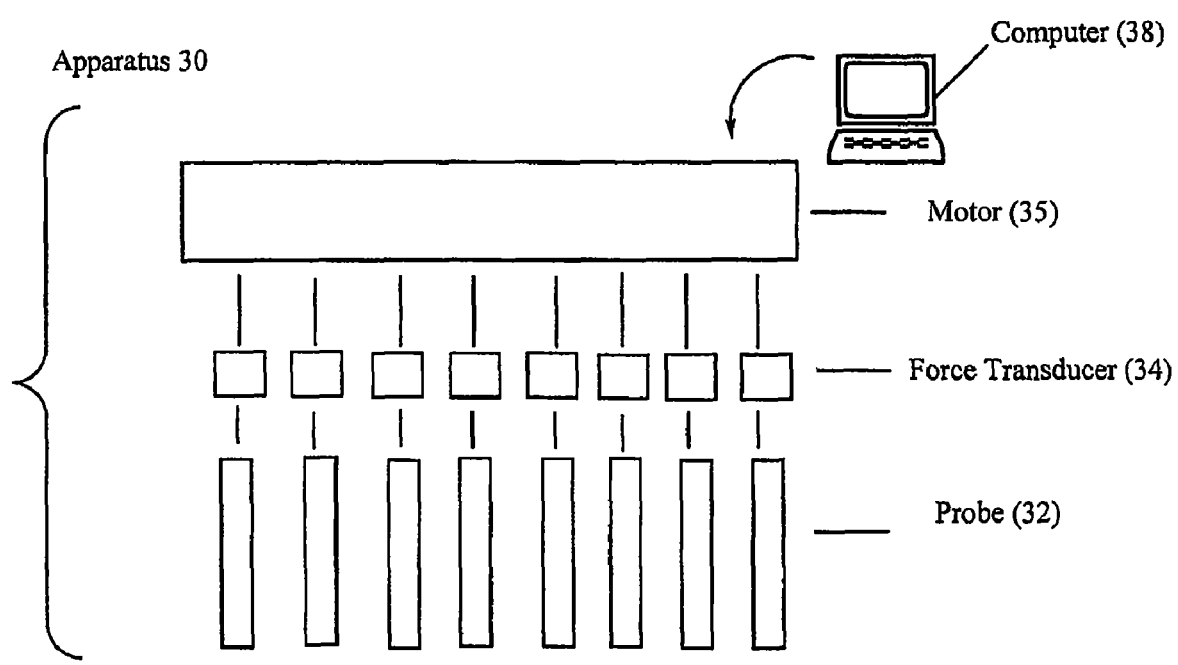
FIG. 26 shows a schematic representation of a tissue indentation system.
Figure 27:
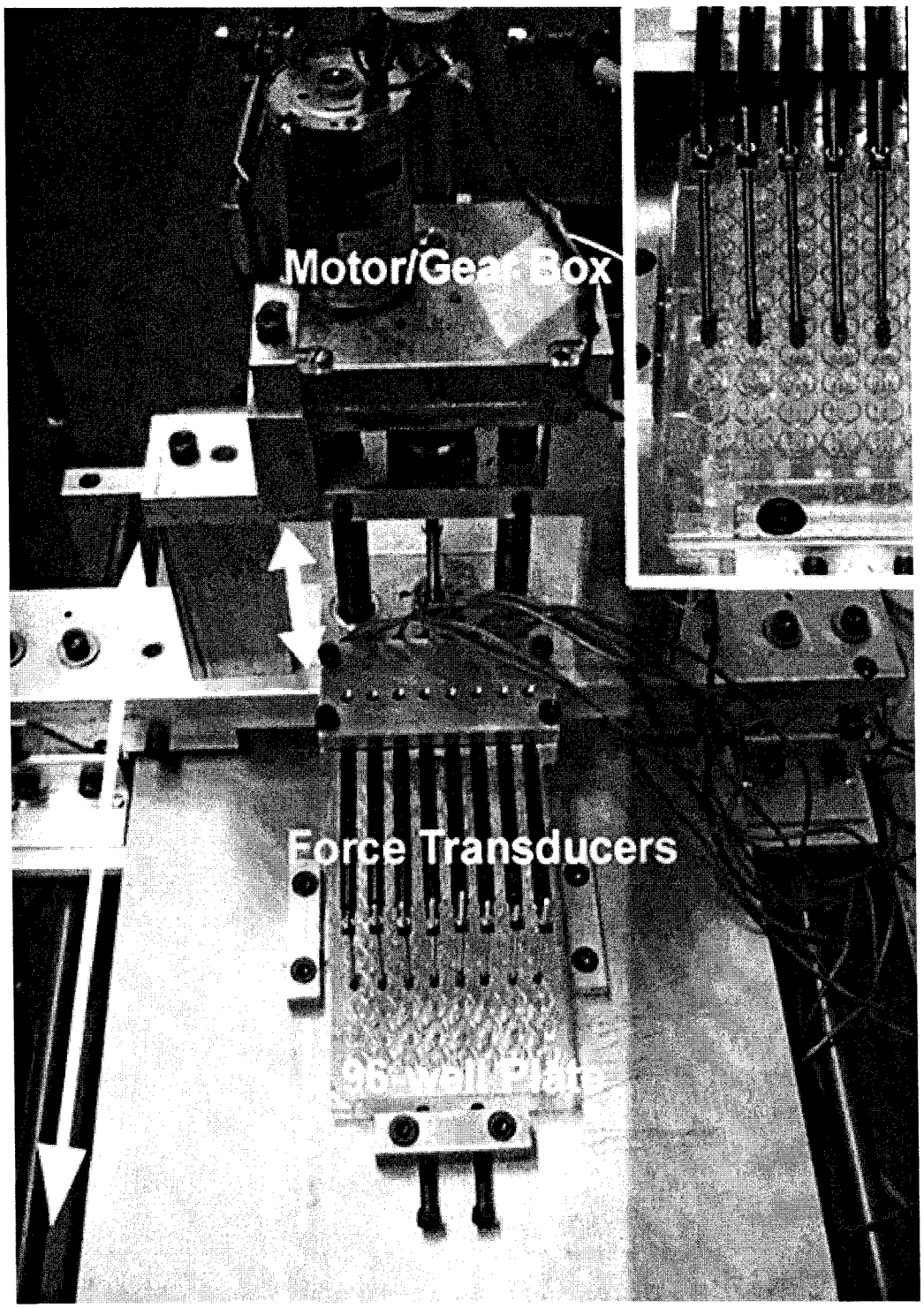
FIG. 27 is a photograph of a prototype tissue indentation apparatus.

In FIG. 26 and FIG. 27, a similar apparatus is depicted, but instead of a single probe, 8 probes (32) are connected to 8 force transducers (34). The force transducers are operatively connected to a motor (35) that controls vertical positioning of the probes. The motor (35) may also control horizontal movement of the probes (32). A holder holds the multi-well plate containing the tissues stationary and the probes (32) move horizontally from well to well. In an alternative embodiment, the probes (32) may be operatively connected to a vertical stepper motor (35) directly and also operatively connected to the force transducer (34).

Figure 29:
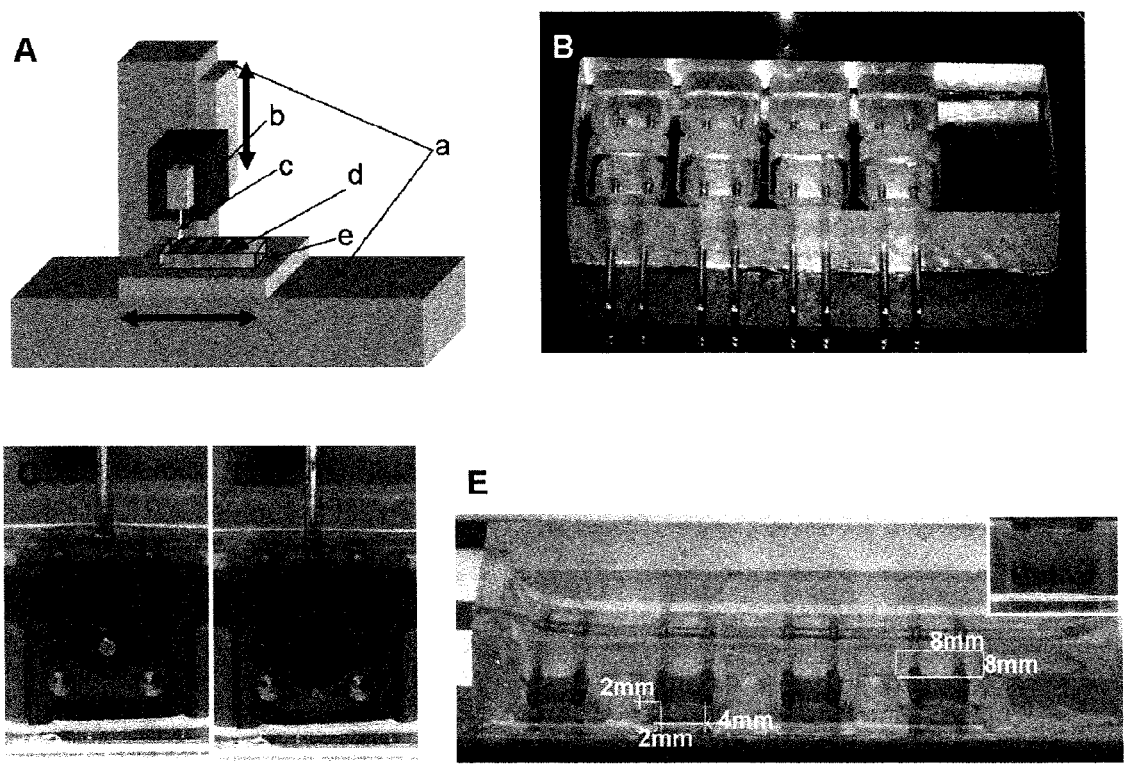
FIG. 29A shows a schematic of the tissue indentation device.
FIG. 29B shows a photograph of a tissue chamber used to form and test engineered tissues (ETs).
FIG. 29C is a photograph showing a force probe approaching an ET formed between two stainless steel bars (a scaffold).
FIG. 29D is a photograph showing the probe indenting the ET vertically and stretching it longitudinally.
FIG. 29E is a photograph showing a typical ET.
Figure 30:
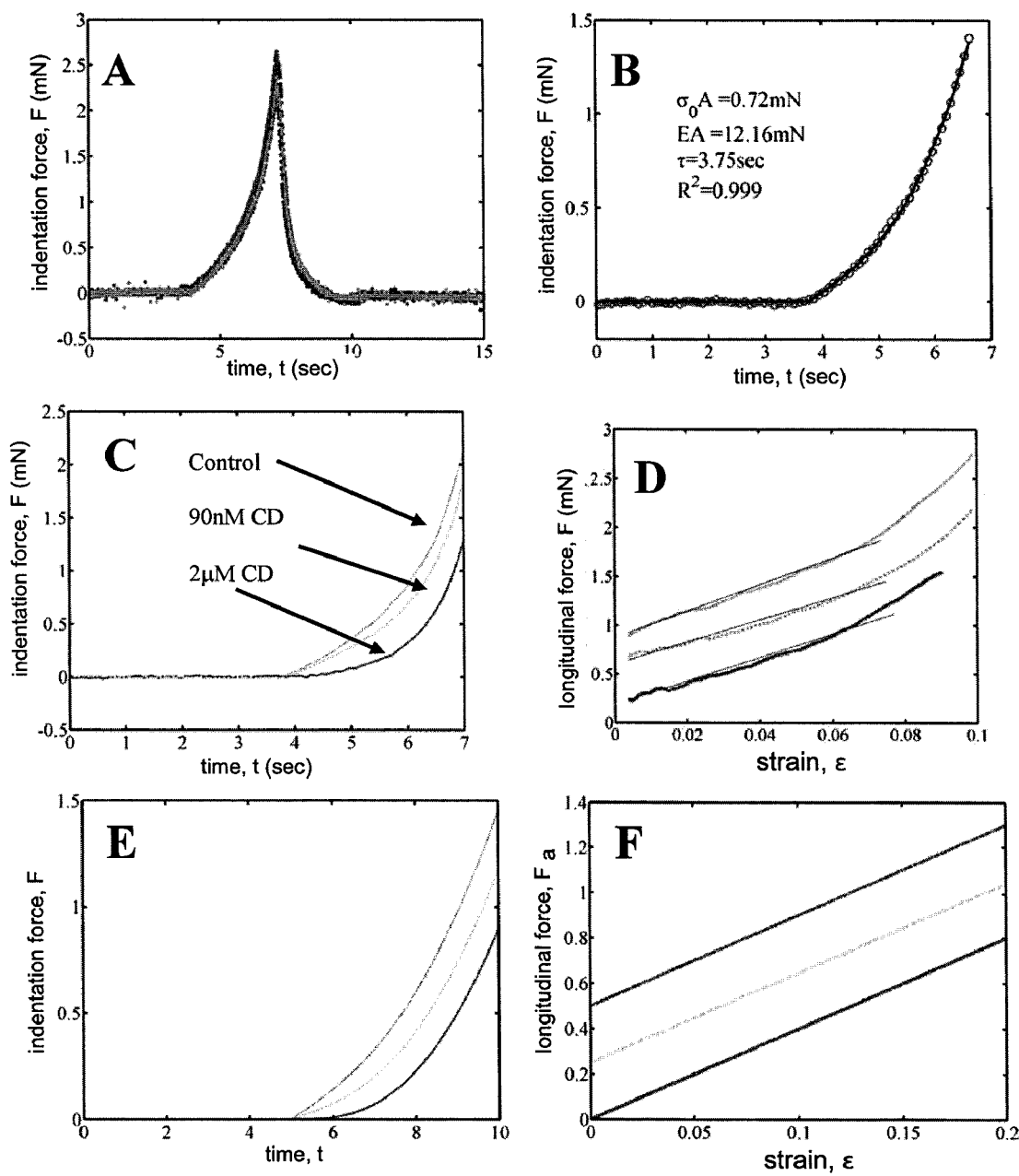
FIG. 30 is a set of graphs showing data obtained from force measurements using the tissue indentation device and comparing the data to the model described in FIG. 28 and the Examples.

The mechanical testing device used in Examples 15-18 is depicted in FIG. 29. FIG. 29A shows a schematic of the tissue indentation device: a) linear actuator slides moved by servo motor (±70 μm accuracy), b) isometric force transducer, c) force probe, d) tissue chamber, e) warm plate (37° C.) connected to a water circulation bath. The device indented 4 samples in one row automatically and an operator manually translated the chamber for the next row. Alternatively, a motor capable of moving from sample to sample in both the X and Y plane could be utilized. A personal computer recorded the force response measured by the isometric transducer and regulated the speed of indentations. The horizontal linear actuator (FIG. 29Aa, ER32-SRN300A, Parker, Wadsworth, Ohio) automatically places the center of each well at right angles below a force-probe (FIG. 29Aa-c). The bottom of L-shaped probe indents and bends the bio-artificial tissue roughly near the center (FIG. 29D). The other end of probe is connected to an isometric force transducer (FIG. 29A-*b*, model 52-9545, Harvard Apparatus, South Natick, Mass.) and moved by a vertical linear actuator (FIG. 29A-*a*, ER32-SRN1000A, Parker, Wadsworth, Ohio). During the tests, the temperature of bio-artificial tissue in the wells was kept at 37° C. using a water jacketed warm plate (FIG. 29A-*e*) connected to a circulating water bath (HAAKE C10-P5, Thermo Fisher Scientific, Inc., Waltham, Mass.). The linear actuators were controlled simultaneously by a personal computer that also recorded the signal generated by the force transducer. The choice of configuration and apparatus suitably depends on the precise application requirements and would be understood to one of skill in the art.

The system of the present invention not only uses smaller amounts of reagents due to the small size of the tissues required for testing, but also allows analysis of tissues maintained in tissue culture conditions, including maintenance of constant temperature and sterile conditions throughout the assay procedure. The bio-artificial tissue can be quickly placed in a holder at its designated position for mechanical measurements. A time-dependent function to lengthen and shorten bio-artificial tissues may be predetermined using computer software for the device. The device may be placed in a laminar flow hood to avoid contamination of the bio-artificial tissues during tests. Therefore, using the device of the present invention, the mechanical measurements can be repeated on the same set of bio-artificial tissues several times over the course of hours, days, or even weeks.

As depicted in FIG. 11*a*, FIG. 26, FIG. 28 and FIG. 29, the probe (32) may be straight or may have an L-shape. One of skill in the art will appreciate that the probe may have a variety of alternative shapes. The probe may be comprised of glass, plastic, or carbon. The probe suitably has a smooth tip, such that the probe does not damage or tear the tissue as force is applied. For example, the tip can be flat or hemi-spherical in shape. In the Examples, a 2-3 nm glass tube with a fire-polished tip was utilized. The probe may have a cross-sectional diameter between about 10 nm and about 2.0 mm, suitably between about 100 nm and about 1.5 mm, suitably between about 1 μm and about 1.0 mm, suitably between about 100 μm and about 500 μm. The probe is operatively connected to an isometric force transducer (34) (such as Model 52-9545, Harvard Apperatus South Natick, Mass.). The connection need not be direct, and in the Examples below, a beam is used to connect the probe (32) to the force transducer (34) and glue or wax are used to connect the pieces together. Any fastener known in the art may be used. In several of the Examples, the force transducer was connected to a stationary stand, and the force was applied by moving the sample vertically to contact the probe. The force transducer may also be connected to a vertical linear positioning stage (36) and a stepper motor as in FIG. 1 *a* or a vertical-horizontal motor as depicted in FIG. 26 and FIG. 27.

The motor(s) may be computer-controlled to allow for fast, smooth operation and the force transducers may also be connected to converters that convert the signal into a data stream for computer analysis.

The multi-well plate (40) may be a specially designed plate comprising scaffolds for holding the bio-artificial tissues or suitably may be a generally commercially available tissue culture multi-well plate to which scaffolds may be added. The number of wells per plate may vary. Typically plates with between 2 and 1000 wells will be utilized, suitably plates with between 50 and 500 wells will be used. In the Examples below, a 96 well plate was used.

Figure 28:
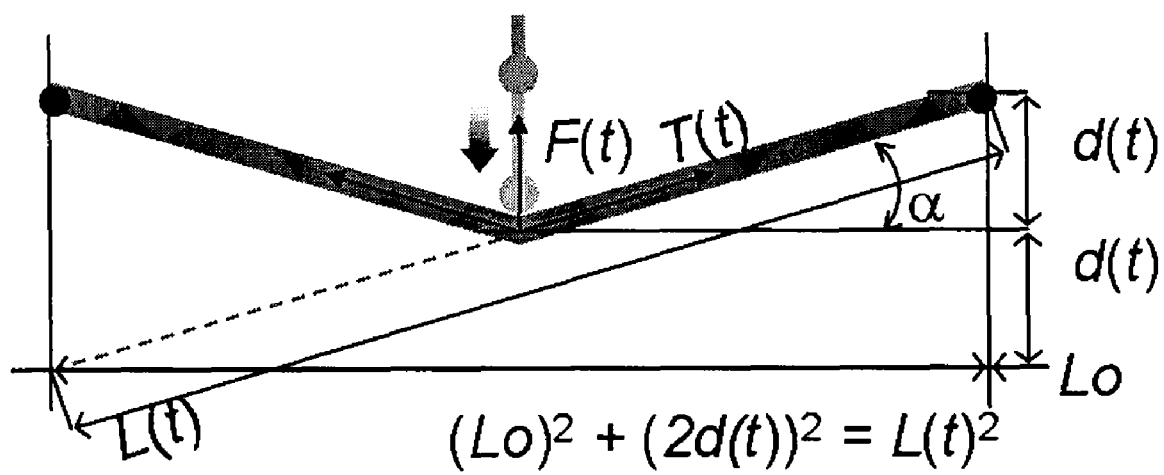
FIG. 28 shows the trigonometric relationship of bio-artificial tissue indentation and stretching in an ideal case.

The system may be used to detect; (1) the stability of measured force over a number of indentations, (2) dose dependent changes in cellular contractility and extracellular matrix (ECM) stiffness as an indication of bio-artificial tissue mechanics, and (3) a short- and long-term changes in bio-artificial tissue mechanics in response to various natural agonists, antagonists and synthetic chemical compounds. FIG. 28 shows the trigonometric relationship of bio-artificial tissue indentation and stretching in an ideal case. A bio-artificial tissue of negligible thickness and length $L_o$ (before the indentation, t=0) was represented by a thick solid-line attached to two horizontal bars (black dots). The force probe (dot with line) pushed the bio-artificial tissue vertically d(t) at its midline. As the force probe advances, the force F(t) recorded by the force transducer and a longitudinal bio-artificial tissue-force, increased by resisting the deformation. A trigonometric relationship of longitudinal force developed in bio-artificial tissue, $(F(t)=2T(t)\sin \alpha)$, vertical indentation depth d(t), ET length at time t, L(t), and 0, $L_o$, can be clearly seen by adding a dotted line extension to the figure.

Figure 12:
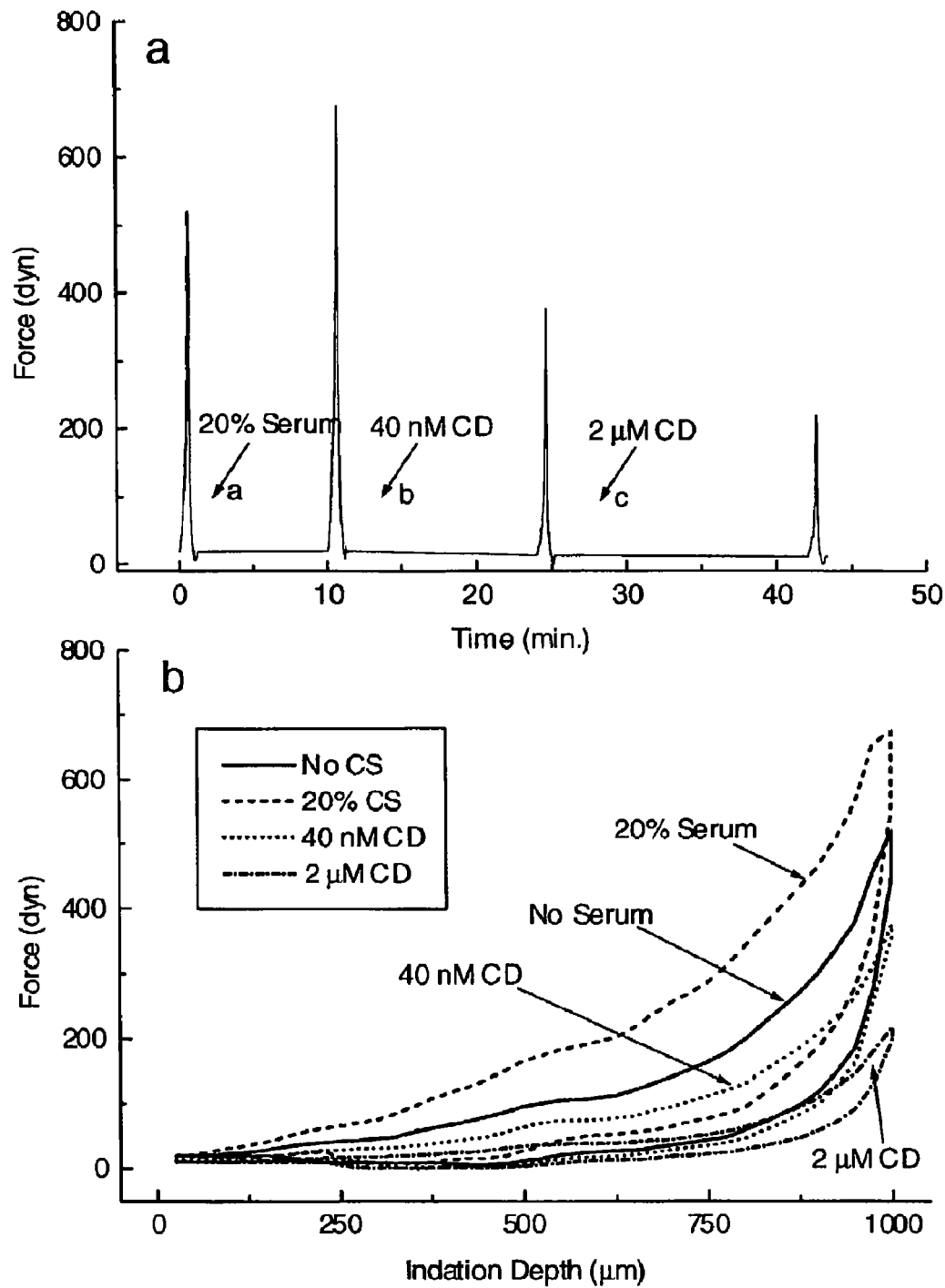
FIG. 12 shows that after the peak contractile force reaches its steady level the tissue model is activated with 20% Fetal Bovine Serum (FBS) (arrow a in FIG. 12(a) to cause an increase in force. This amount of FBS activates fibroblast non-muscle myosin.

FIG. 12 shows data obtained using the system exemplified in FIG. 11 above. The data shows that after the peak force reaches its steady level the sample is stimulated with 20% fetal bovine serum (FBS) (see arrow a in FIG. 12*a*). This amount of FBS activates fibroblast non-muscle myosin producing a contractile force that stiffens the reconstituted tissues. At about 10 minutes after the FBS addition, there is about a 25% increase in the peak force of subsequent indentations (FIG. 12*a*). Nearly 15 minutes after the addition to the medium of 40 nM cytochalasin D (CD) (see arrow b of this figure), the peak force from subsequent indentations has decreased about 40% from its initial level (FIG. 12). A further reduction of peak force was recorded 20 minutes after addition of 2 μM CD. FIG. 12(*b*) is a plot of the same data as FIG.

12(a), but FIG. 12(b) shows force versus indentation depth rather than force versus time as in FIG. 12(a).

Figure 13:
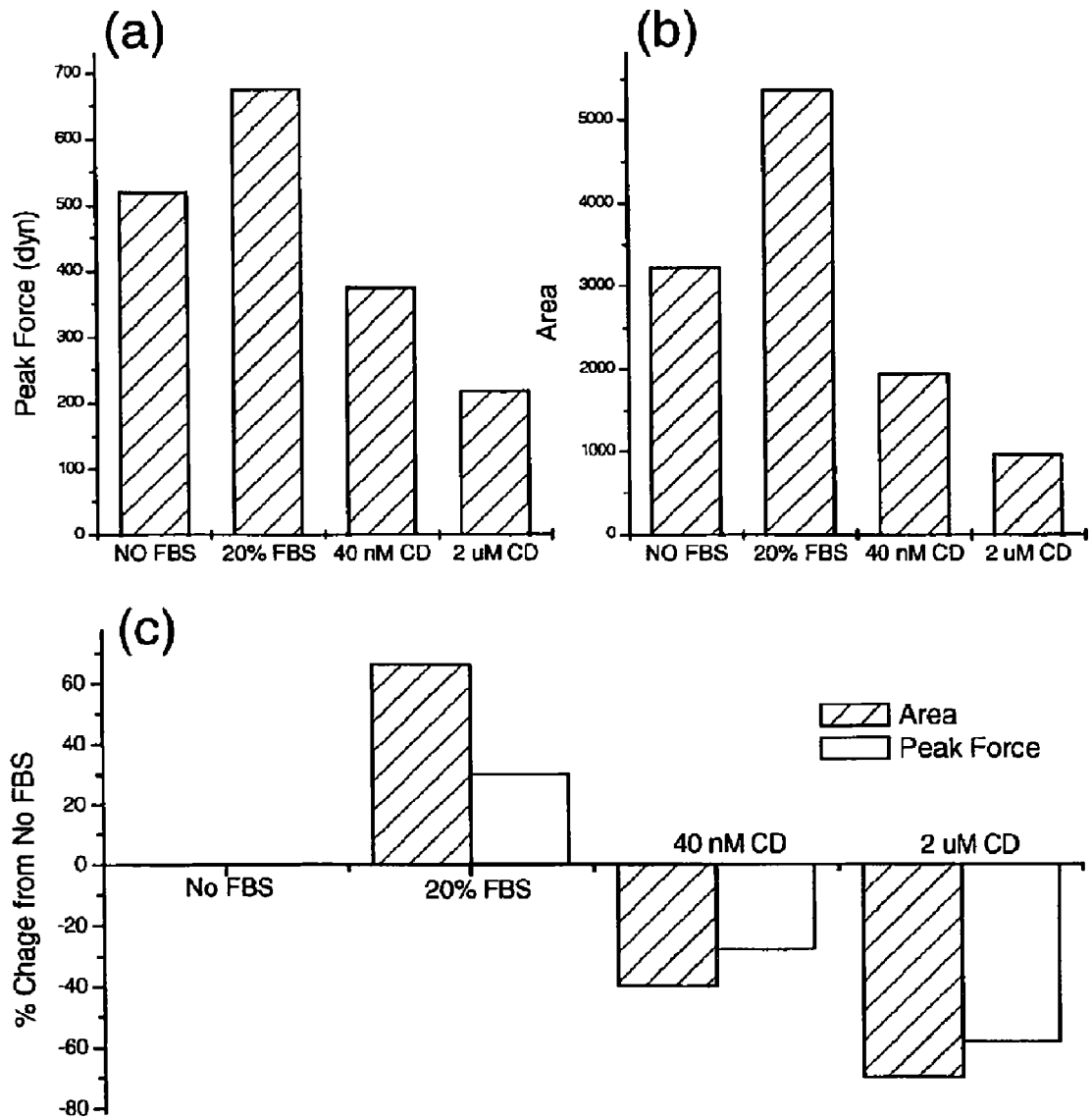
FIGS. 13(a), 13(b) and 13(c) show changes in the peak tissue contractile force and area (arbitrary unit) of hysteresis as relates to FIG. 12.

FIG. 13 is a comparison of percent changes in the peak force and area of hysteresis during the test which generated the data of FIG. 12 above. FIG. 13(a) shows the peak force (dynes) measured prior to FBS treatment (no FBS) after 20% FBS, after 40 nM CD and after 2 µM CD. FIG. 13(c) shows the corresponding changes in peak force and hysteresis (area) relative to the values obtained prior to FBS treatment.

The area of hysteresis changes to a greater extent upon stimulation and CD addition as compared to the peak force. Therefore, the area of hysteresis is a more sensitive parameter than the peak force for monitoring the changes in mechanical properties of the tissue model.

Figure 14:
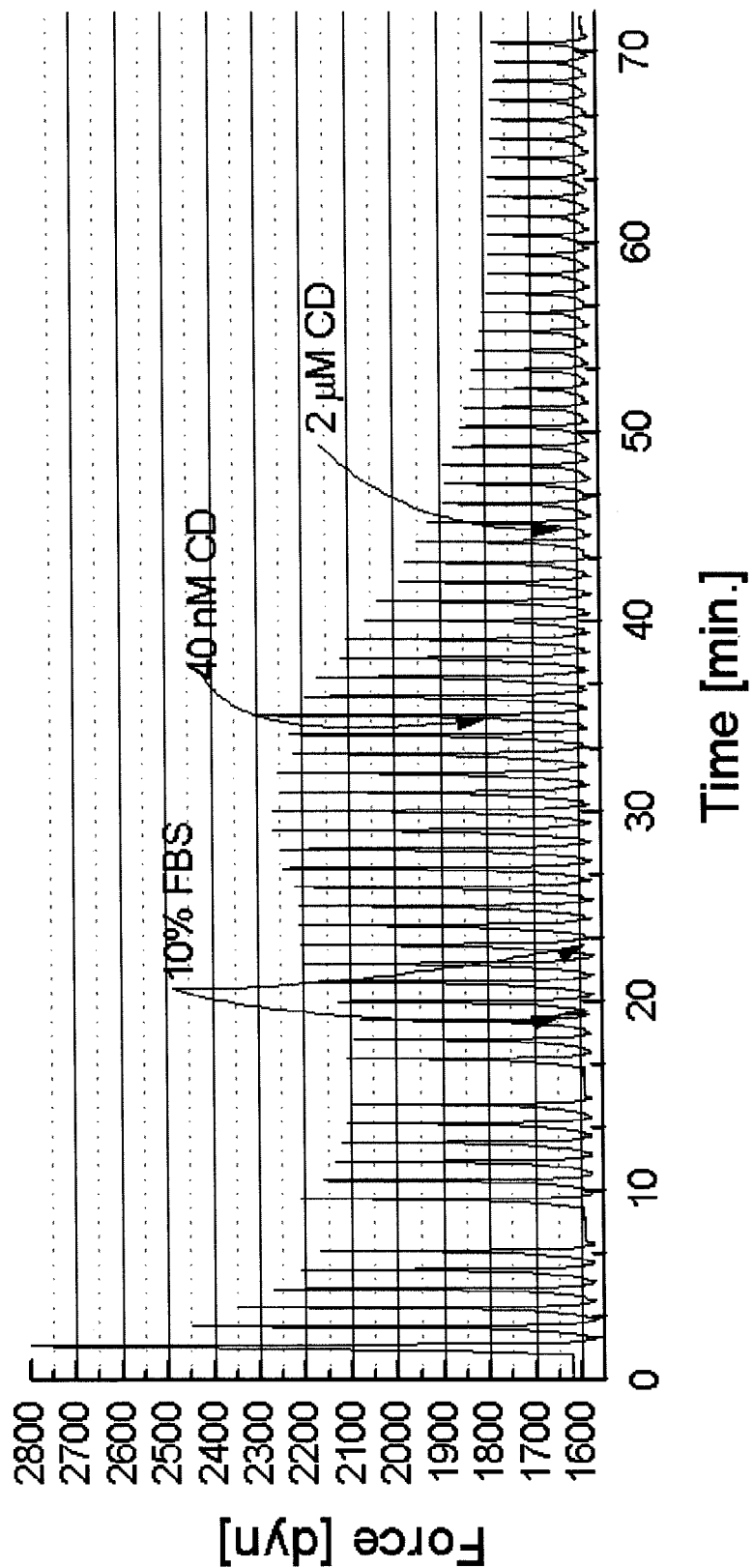
FIG. 14 illustrates a series of force responses to indentations on reconstituted tissue membranes. A small membrane in a well of a 96-well plate was repeatedly indented (each peak represents one indention.) Force responses to the indentations were recorded over 70 minutes. Peaks of indentation increased due to activation of myosin by addition of 10% FBS, whereas cytochalasin D (CD) reduced peaks in a dose dependent manner by disrupting the actin cytoskeleton. (Force scale was not offset to zero.)

FIG. 14 shows measurements of the mechanical properties of a miniaturized reconstituted tissue using a 96-well plate. The system can be used for high throughput screening since it allows rapid and parallel measurements using the multi-well plate.

FIG. 14 shows the force trace of mechanical measurements conducted using 96-well plates. A small membrane of reconstituted tissue is supported by a stainless steel wire frame. A vertical probe attached to an isometric force transducer indents the membrane and measures the force resisting the indentation. The addition of 10% FBS increases the force peak's height by 30%. The addition of CD reduced the height of the peaks by 60%.

By automating the procedures using the 96-well plate system or going to an even higher degree of parallelism, the method in accordance with the present invention may be suitably expanded to high throughput applications using the invention. One skilled in the art could further miniaturize bio-artificial tissues and make use of multi-well plates with as many as 10,000 wells. Libraries of compounds can be screened and managed based on their biological activities using the disclosed methods and tissue models.

Typically, contractile force increases rapidly over a period of a few minutes following contact of an agent with a tissue model system. The contractile force reaches a maximum value and after reaching that maximum value the contractile force may be sustained over a period of an hour or more or the contractile force may decline at a rate that is specific to the activator and a cell type. The reason for the relaxation of the force is not critical but this produces further information and data for characterization of force and stiffness response.

During activation, different pathways, involving specific sets of enzymes and co-activators, which can vary among different activating agents, carry the signal received at a cell surface receptor into the cell to activate contractile force. Hence, the development and maintenance of contractile force provides an indicator (or profile) of specific cellular responses to contact with exogenous activators and to the operation of transduction pathways from cell surface receptors to the activation of myosin. The profile for non-muscle cells includes the maximum contractile force value and the maintenance of the contractile force over time.

The invention is further described in the following examples which are not intended to limit or restrict the invention in any way.

EXAMPLES

Example 1

Preparation of Tissue Models

Bio-artificial living tissue models were prepared from cells and extracellular matrix (ECM). These models simulate natural tissues.

Chicken embryo fibroblasts (CEF's) isolated from 11-day chicken embryos (Spafas Inc., Preston, Conn.) were maintained in Dulbecco's modified Eagle's medium (DMEM) supplemented with 10% fetal calf serum (FCS), penicillin at 50 units/ml, and streptomycin at 50 microgram/milliliter. The CEF's used to make tissue models were passaged once or twice from primary cultures. Monomeric collagen solubilized in 0.02 M acetic acid (Upstate Biotechnology Inc., Lake Placid, N.Y.) was neutralized at 4° C. with 0.1 N NaOH and mixed with concentrated DMEM stock to yield a final normal DMEM concentration. The fibroblasts suspended by trypsin (FIG. 1a) were mixed with the collagen solution (FIG. 1b), the cell suspension was poured into Teflon casting wells (FIG. 1c), and the wells were incubated at 37° C. with 5% $CO_2$ (FIG. 1d). The collagen polymerized within 15-30 min and fibroblasts were captured within the hydrated collagen gel. The collagen gel formed a ring (3 mm thick, 3 cm diameter) between the inner wall of the cylindrical well and the central mandrel. While in culture the cells compressed this ring, reducing its volume about 10-fold (thickness 200-300 µm). The ring could then be removed from the mandrel (FIG. 1e and FIG. 1f) and mounted on the measuring instrument (FIG. 1g) as described below.

The types of cells that can be used to form reconstituted tissues are not limited to CEF. Cell types that have been used to form suitable tissues for mechanical measurements include chicken embryo fibroblasts, chicken embryo cardiac fibroblasts, chicken embryo cardiac myocytes, rat cardiac fibroblasts, mouse myotubes, mouse skeletal muscle $C_2/C_{12}$ cell line, normal mouse mammary gland (NMuMG) cell line and its mutant lines lacking $\alpha_1$ and $\alpha_2$ integrins, mouse fibroblasts and their mutant cell lines, REF52 fibroblasts, A7R5 smooth muscle cells, CCL39 fibroblasts and NR6 fibroblasts and combinations thereof. The cells can be isolated from chicken embryos or obtained from American type culture collection (Manassas, Va.).

Example 2

Measurements on and Mechanical Assembly of a Ring System

Mechanical measurements were carried out using a ring system. After two days of incubation (serum starvation for the final 12-16 hours), the mandrel was removed from the casting well and the tissue model-ring was removed gently from the mandrel. As shown in FIG. 1 the tissue model-ring was looped over the triangular hook connected to an isometric force transducer (Model 52-9545, Harvard Apparatus, South Natick, Mass.) by a fine, flexible gold chain. The ring was also looped over a horizontal bar connected to a sliding element moveable vertically and linearly by a stepper motor (P/N 1-19-3400 24V DC 1.8° step size, Haward Industry, St. Louis, Mo.) controlled by a micro-stepping driver (IM483 Intelligent Motion Systems) to measure stress and dynamic modulus of the sample. The micro-stepping driver was controlled by a personal computer with software which enabled the stepper motor to achieve smooth motion. An analog-to-digital signal converter (CIO-DAS1602/16, Computer Boards, Inc., Mansfield, Mass.) attached to the computer translated the voltage signal from the isometric force transducer to a digital signal for recording on a data recorder. The stepper motor controlled the stretching of the tissue. Force exerted by or on the tissue was transmitted to the force transducer by the gold chain.

The tissue sample was submerged in 50 ml Hepes-buffered DMEM (pH 7.4) in a thermo-regulated organ bath (Harvard Apparatus, South Natick, Mass.) maintained at 37° C. The two horizontal bars over which the ring was looped were initially set to hold the ring at its original contour length (corresponding to the circumference of the mandrel).

Example 3

Testing of Tissue Model System

Typically, for stiffness measurements, the tissue model is subjected to a sequence of stretch cycles. In each cycle the tissue model is slowly stretched from 0 to 20% over 30 minutes and the tissue model is then returned at the same rate to its original length by actuation of the stepper motor. The resulting increase in contractile force during the first stretch is substantially larger than the contractile force in subsequent stretches (FIG. 2a). For each stretch after the first stretch there is a further small decrease in maximum contractile force, but the decrease becomes negligible after sufficient pre-stretching. The tissue models produced contractile force in response to the activation of fibroblasts by serum. This contractile force was abolished by disrupting the actin cytoskeleton with cytochalasin D (2 μM) (FIG. 2b).

The amplitude of the force response divided by the stretching amplitude corresponded to the dynamic stiffness of the sample subjected to a preselected sinusoidal length change. The dynamic stiffness can be measured at various frequencies and amplitudes. The dynamic stiffness and tension of the FPM (fibroblast populated matrices) were measured at various strain levels by elongating and shortening the sample at a constant rate (10 micrometers/minute) up to 20% strain with superimposed sinusoidal length change (typically, 20 μm amplitude; 0.5% stain, 0.5 Hz frequency) (FIG. 1g). The apparatus is set to change the tissue length with prescribed rate and amplitude.

This determination may be accomplished by separating the cell and matrix contributions within the generated mechanical response profile since the cells, the matrix, and the interactions between the cells and matrix all contribute to the tissue stiffness of a reconstituted tissue model.

As shown in FIG. 3, dynamic stiffness correlates almost linearly to the isometric force (FIG. 3c) while their changes were measured at the original tissue length in response to the FBS stimulation and CD addition (FIGS. 3a, b). Therefore, both the isometric force and the dynamic stiffness are good indicators of the mechanical properties of reconstituted tissues. The application of this method to determine the dose-dependent decrease in the force and stiffness of the tissue model caused by the disruption of actin cytoskeleton with two different agents is described below. Data from the examples provide characterization of mechanical properties of connective tissues models, such as fibroblast populated matrices (FPM's) via uniaxial stretch measurements. The tissue model(s) resemble natural tissues in their exponential dependence of stress on strain and linear dependence of stiffness on force at a given strain.

Example 4

Figure 19:
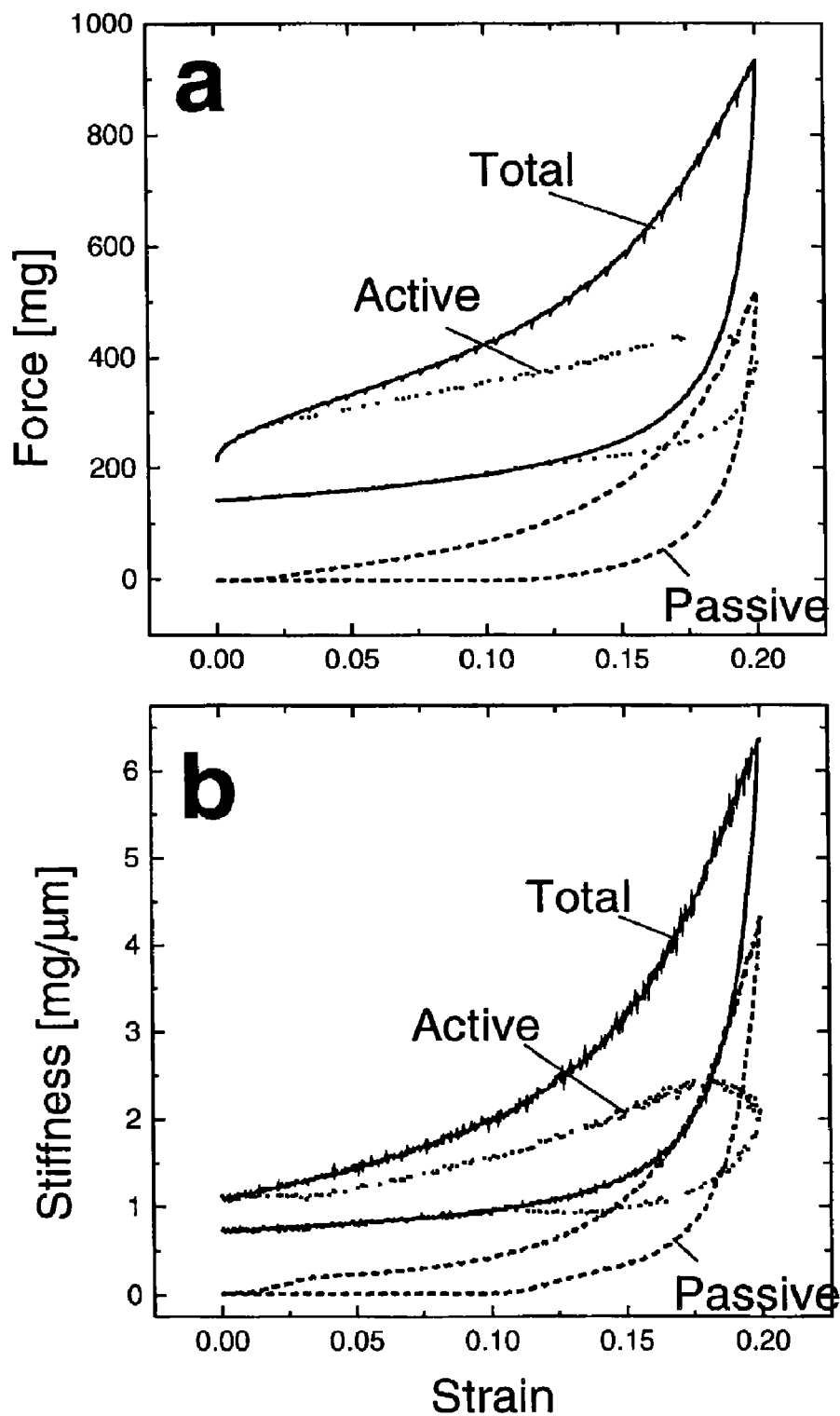
FIG. 19a shows the dependence of force on strain for a tissue model ring measured after stimulation by FBS (labeled "Total"). The ring was then treated with 2 μM CD and measured to yield the curve labeled "passive". The difference between total and passive is labeled "active.
" FIG. 19b shows dynamic stiffness derived from the same measurements.

Determination of Contributions of Cells and Matrix to Mechanical Properties of Tissue Model Using a Ring System Determination of cellular contributions and matrix contributions to the mechanical properties of reconstituted tissue models was carried out as it is highly desirable to obtain a more specific profile of the reconstituted cellular response to an activator. Activating cellular contractile forces by calf serum and disrupting F-actin by CD provide active and passive components which respectively emphasize cellular and matrix mechanical contributions. In FIG. 19, the force versus strain (a) and dynamic stiffness vs. strain (b) for a pre-stretched tissue model activated by 20% CS is shown by solid lines labeled "Total". The force and stiffness curves obtained after treatment by 2 .μM CD are shown by broken lines labeled "Passive". The difference between the Total and the Passive curves, labeled "Active", is shown by dotted lines. All the curves exhibit hysteresis. The "Active" curve increases approximately linearly with strain; the "Passive" curves increases approximately exponentially. The dynamic stiffness was measured at 0.5 Hz, (b). Note that the dynamic stiffness and the force vary similarly with strain. These measurements were carried out after a single pre-stretch cycle to avoid the large difference between the first and second stretches (see FIG. 2). It has been determined that the "active" and "passive" curves report primarily on the cellular and matrix portions of the tissue model.

The contributions of the cells and matrix are separately (and adequately) assessed. The cellular contributions are eliminated by reducing the stiffness of the cells and effectively disconnecting the cells from the matrix by addition of an effective amount of an actin filament disrupter. This is accomplished by adding CD or Latrunculin-B (LA-B) as a disruptor (for example). CD and LA-B, both, disrupt actin filament cytoskeleton organization within cells and prevent the development of contractile force and weaken cellular mechanical responses. It is therefore possible to determine the effects of activators and inhibitors specifically on cells or on the matrix. This ability to examine separately these two mechanical systems provides further specificity to this method.

The isometric force and the dynamic stiffness of two day-old tissue models, which have been serum starved for 16 hours prior to the experiment, were measured over a range of CD concentrations. The measurements were carried out serially on each tissue model, beginning with the lowest concentration of CD. For each tissue model, CD was added and force and stiffness were measured and then the CD concentration was increased for the next measurement (FIGS. 4A, B). The CD was dissolved in DMSO. The total amount of DMSO added to the organ baths containing the tissue model was less than 0.1% of the total volume of the DMEM. This quantity of DMSO had no significant effect on the force and stiffness of FPM's. The data shown were averaged over quadruplicated samples, and the same experiment was repeated at least twice. The force and dynamic stiffness were significantly decreased at a CD concentration as low as 2 nM. At this concentration, no effect was observed by confocal microscopy on the actin cytoskeletons stained with Rhodamine phalloidin in monolayer cell cultures. Both force and dynamic stiffness continued to decrease as the CD concentration increased up to 2 μM. At this concentration, the force was reduced almost to zero and the stiffness had nearly reached its minimum value. For CD concentrations higher than 2 μM, the stiffness did not significantly diminish further (data not shown). The concentration of CD needed to reduce the force and dynamic stiffness by 50% was approximately 0.25 μM.

Measurements of the effects of LA-B on the mechanics of tissue models demonstrated differences between the mechanism of action of LA-B and the mode of action of CD on the actin cytoskeleton. Incremental additions of LA-B and mechanical measurements on tissue models were carried out serially as in the studies of CD. The data were averaged for at least three samples, and the same test was repeated at least twice. The concentration of LA-B needed to produce a significant effect on the tension and the stiffness of FPM's was much higher than that required of CD (FIGS. 4C, D).

Force and stiffness had a sigmoidal dependence on LA-B concentration. The estimated half maximum concentrations for reducing the force and stiffness were 53 nM and 68 nM, respectively. The LA-B-dependent decrease of tension and stiffness was confined to a single decade of LA-B concentration, whereas the response to CD ranged over almost three decades. This strongly suggests that CD and LA-B operate by different mechanisms to disrupt the actin cytoskeleton. Small differences in the values of force at the high concentration limits of CD and LA-B (FIG. 4) were observed.

For a viscoelastic system the dynamic stiffness depends on both the elastic and viscous resistance to stretching. The viscous contribution can be measured by the phase angle, $\delta$, between force and strain.

In these tests the change of phase angle, $\delta$, due to disruption of the actin cytoskeleton was small (data not shown). Hence, in this system CD and LA-B had a relatively minor effect on the viscosity of the tissues. Therefore, it is reasonable to suppose that the viscous contribution of the cells to tissue model force and stiffness was also minor. These measurements illustrate how force and stiffness measurements rapidly and sensitively indicate the effects of these "inhibitors" via their effects on the actin filament system.

Example 5

Cardiac Tissue Models

The tissue models made using cardiac myocytes isolated form chicken embryos become contractile spontaneously. Chicken embryo extracts (CEE, Life Technologies, Rockville, Md.) have been known to be required to form spontaneously contracting artificial cardiac tissues (FASEB J July 1997; 11(8):683-94, FASEB J April 2000; 14(5):669-79). Media conditioned by cardiac fibroblasts can replace the CEE. The conditioned medium (CM) was produced by incubating a confluent monolayer of cardiac fibroblasts in 100 mm dish preincubated with DMEM supplemented with 10% FBS for 2 days. The medium is changed to DMEM containing no serum and is incubated for 24 to 48 hours to make the CM. The cardiac tissue models cultured with the CM supplemented with 10% FBS start spontaneously contracting in 4 to 5 days without adding any CEE. The cardiac myocytes grown in the tissue models spread much better (FIG. 5a) than those cultured in DMEM containing only 10% FBS (FIG. 5b). A similar difference is observed for cells growing on tissue culture dishes. The cardiac myocytes cultured in the CM (FIG. 5c) spread much better and cover larger areas than those cultured in DMEM supplemented with only 10% FBS (FIG. 5d). This suggests that factors secreted by the fibroblasts promote cardiac myocytes spreading and spontaneous contraction. Conditioning of medium to induce cardiac myocytes to spread and contract spontaneously may also be accomplished by coculturing cardiac fibroblasts as a monolayer at the bottom of the tissue culture dishes incubating cardiac tissue models. The conditioning of medium promoting spontaneous contraction of the cardiac tissue models may also be accomplished by coculturing connective tissue models containing cardiac fibroblasts. The fibroblasts can also be mixed with myocytes to form cardiac tissue models. This induces strong contraction in 4 to 5 days yet it also stops spontaneous contraction as early as 7 to 8 days of the culture. See the description of the various conditions in the supplemental table in FIG. 5.

Example 6

Cardiac Tissue with Mouse Cells

Figure 6:
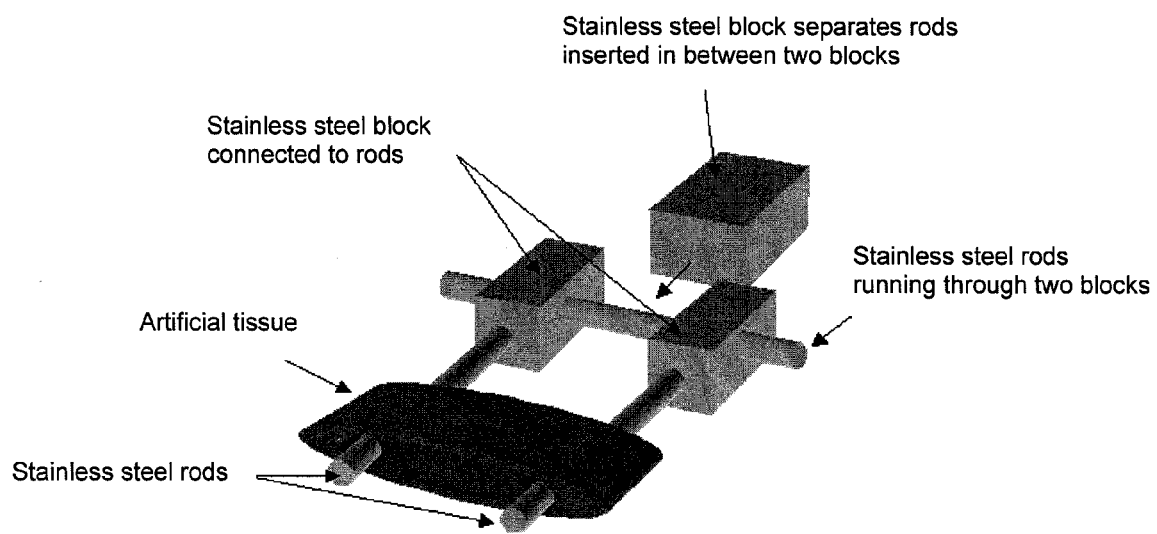
FIG. 6 is a stainless steel spacer used to culture model tissues after removal from the molds shown in FIGS. 1c and 1e.

Embryonic hearts are removed from stage E17-E19 mouse embryos. Cardiac myocytes were isolated by several collagenase (167 µg/ml) digestions after 15 min. trypsin (0.25%) treatment at 37° C. Isolated cells from the hearts were cultured on tissue culture grade plastic dishes for 1 hour to remove nonmuscle cells by the rate of adhesion to the tissue culture grade dishes (nonmuscle cells adhere much faster than the muscle cells). Non adherent cells were removed with medium and sedimented with low speed centrifugation for 15 min. For 1 ml of artificial tissue, 1 million myocytes were mixed with 0.75 mg of rat tail collagen kept in acetic acid (0.02 N), which is neutralized by adding an appropriate amount of NaOH (0.1 N), and 0.25 mg of fibrinogen kept in phosphate buffered saline. A higher concentration (more than 1×.) of tissue culture medium (DMEM) was added to the sample solution to maintain a normal final concentration of the medium. One µl of thrombin (1 unit/ml) was also added to the solution to initiate fibrin formation. The fibrin converted from fibrinogen polymerizes with collagen to form a stronger gel, which facilitates handling the sample. The 0.5 ml of sample solution was poured into a ring mold as described previously and incubated (5% $CO_2$ at 37° C.) for 30 min. The gel is removed from the mold and cultured with the spacer—two stainless steal bars (~1 mm in diameter) separated by a stainless steel block (FIG. 6). After incubation of 5-7 days embryonic myocytes spread into the collagen/fibrin gels and spontaneously twitch. The cells make contact with one another and start twitching synchronously.

Figure 7:
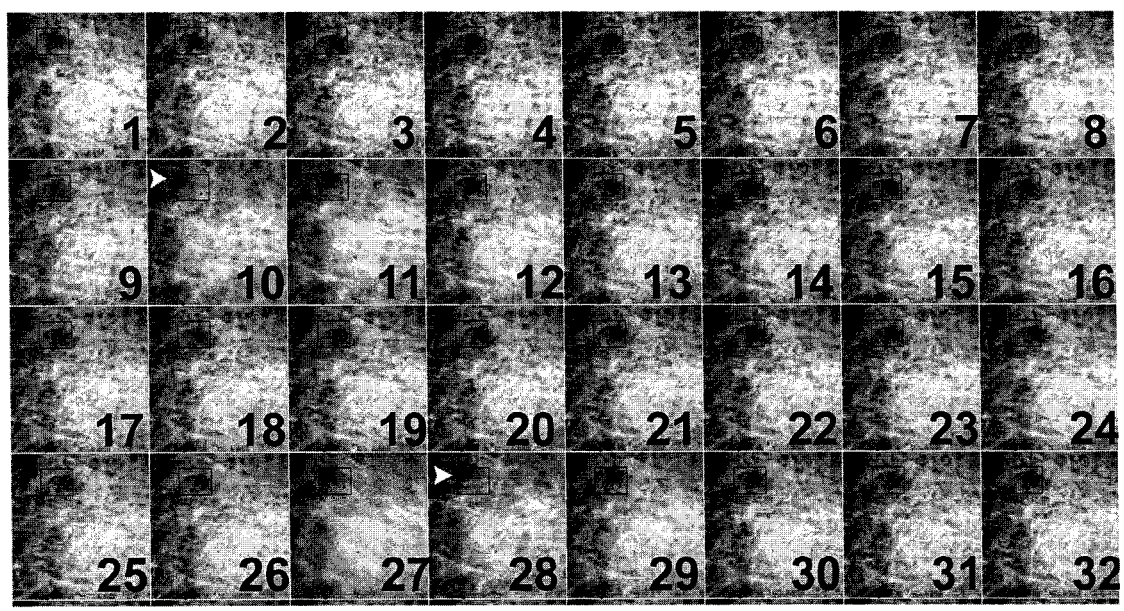
FIG. 7 shows a time sequence of images (1 through 32 with a 200-msec. interval) capturing spontaneous contraction of cardiac tissue models made using cells from embryonic mouse hearts.

A sequence of images capturing the mouse embryo cardiac tissues is shown in FIG. 7. A dark feature within the image is enclosed by a rectangular frame. The frame in each image is stationary. Displacement of the feature away from the frame periodically indicated by white arrows at image 10 and 18 indicates twitching of the sample by the cardiac myocytes (FIG. 7).

In vitro tissue models made using mouse cells and mimicking the mechanical properties of mouse cardiac tissues provide a useful test system for evaluating the effects of pharmaceutical candidates. Well established methods of for knocking out specific genes in mice has created an enormous number of mutant mice lacking specific molecules by which cardiac functions are regulated. For instance, studies using a mouse lacking type 1 NO synthase (Circulation Jun. 25, 2002; 105(25):3011-6), Connexin43 (Development April 2002; 129(8):2031-42), and familial hypertrophic cardiomyopathy linked to myosin binding protein-C (Circ Res Mar. 22, 2002; 90(5):594-601) are just few examples. Model cardiac tissue can be made using cells from a knockout mouse to study the role of a specific protein molecule in cardiac development and function. Many knockout mice do not survive after birth or even beyond a defined embryonic stage. Therefore, functional studies of the heart of these knockout mice are limited. Since cells isolated from embryonic or neonatal mice can be used to make functional tissues, the system can be used to study functions of molecules, which are inaccessible using intact tissue or whole animals. The study of knockout mice is useful for studying the efficacy of gene therapies in vitro.

Example 7

Miniaturization of Tissue Models

The samples are miniaturized by using a smaller mold (right in FIGS. 8a, b) instead of the one used ordinarily (left in FIGS. 8a and 8b). The sample sizes are determined by the diameters of the mandrels and inner diameters of the wells. The molds before (A) and after (B) assembling the parts are shown in FIG. 8. The mandrel diameters of small and regular size molds are 3/16 and 3/8 inches, respectively. The inner diameters of the small and regular size wells are 9/32 and 17/32 inches, respectively. By using the smaller mold, the size of tissues are decreased 5-fold in volume (1 ml to 0.2 ml) (* indicates the tissue samples in FIGS. 8c and 8d). The miniaturization of the tissue model allows us to do tests similar to those described in FIGS. 2, 3, 4, 15, 16, 17, 18, 19, 20, 21, 23 using regular size samples but in much smaller organ baths using less medium and consuming a fraction of the chemicals. At least a 5-fold reduction, which is equal to the reduction of sample volume, can be achieved.

Figure 9:
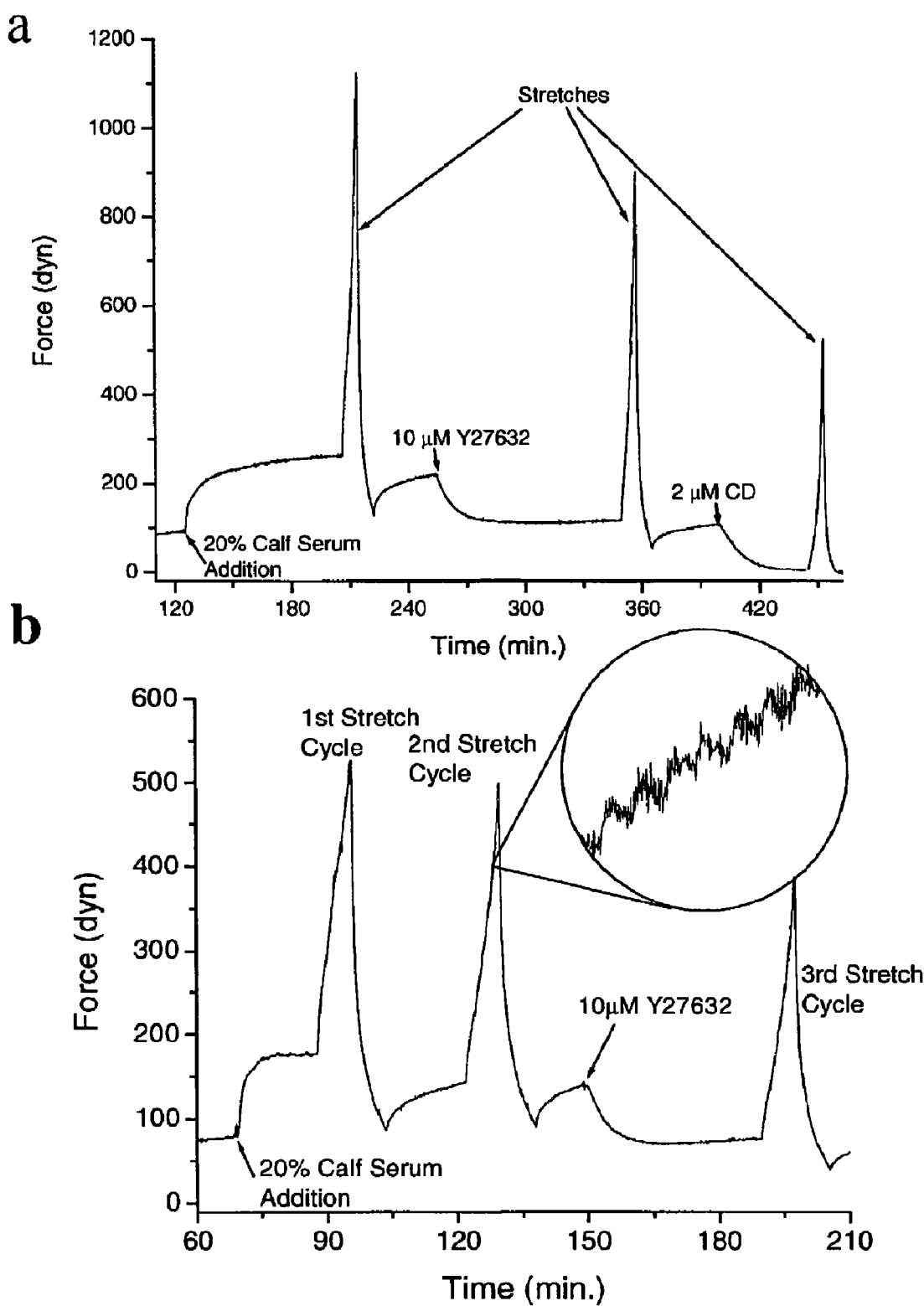
FIG. 9 is a comparison of force traces observed using small and regular size cardiac tissue models made using these molds. The change of force with time shown in FIG. 9a is observed using a cardiac tissue model made with the regular size mold. The change of force with time in response to stretch and treatment with Y27632, an inhibitor of the activation of myosin activation by Rho kinase, is shown in FIG. 9b. The insert of FIG. 9b shows an enlarged plot of force and time during the sample stretch spontaneously contracting.

To demonstrate and prove this concept, the mechanical responses of the cardiac tissue models to the treatment of serum and Y27632 are observed (FIG. 9). The tissue models are made using the regular size mold with chicken cardiac cells (9a). They typically look like the tissue models (indicated by *) shown in FIG. 8d. FIG. 9b also shows the similar trace of force obtained with miniaturized tissues, which look like the ones in FIG. 8c. Both sizes of tissues increase force in response to 20% (v/v) calf serum and forces are decreased by Y27632 treatments. Differences in magnitudes of changes in response to these chemicals using different sizes of tissue models are not greater than 2 fold. This demonstrates that the miniaturized system has a large enough range of signal to detect changes induced by pharmaceutical candidates. The miniaturized system also shows a force-response curve to mechanical stretches similar to that of the normal-sized tissues. Miniaturized samples made using chick cardiac cells show twitch responses. Therefore this system can be used to test the effects of pharmaceutical candidates treating cardiac dysfunctions (Insert in FIG. 9b)

Example 8

Tissue Model Measurements in Multi-Cell Indentation System (Using a Multi-Well Plate)

Fabrication and measurement of miniaturized reconstituted tissue specimens were carried out using membranes and strips of reconstituted tissues in wells of a 96-well plate system.

Example 9

Mechanical Assembly of a Multi-Well Plate System

A triangular frame made of stainless steel wire 1 mm in diameter was employed as a scaffold on which the reconstituted tissue formed. The wells are slightly tapered toward the bottom and the frame is securely positioned 1 mm above the bottom of the well (FIG. 11a). The non-polymerized solution of collagen containing cells and appropriate cell culture media as described above was poured into the wells filling the wells to a level 3 mm above the bottom (FIG. 11b). The 96-well plate was incubated at 37° C. with 5% $CO_2$. During the incubation, cells compressed collagen matrices by squeezing liquid out from the porous collagen matrix. Without the wire frame, the reconstituted tissue contracted into a small sphere floating in the tissue culture medium. It was discovered that by utilizing different shapes of wire frames the collagen matrix was compressed into shapes corresponding to shapes of the frames. Illustratively, a triangular wire frame made a membrane spanning among the three edges as shown in FIG. 11a. Other wire frame shapes, such as one shown in FIG. 11b, produced tissue strips with different widths. A porous support material such as a Velcro fastener was not required to facilitate tissue adhesion even to the non-porous stainless steel surfaces of a wire. The collagen was compressed to a greater extent at the outer portion of the membrane or strip. Therefore, this outer portion of the membrane can withstand stress produced by the cells and prevented it from ripping the membrane off the wire frame.

Example 10

Measurements of Force, Tissue Stiffness and Hysteresis of Membranes or Strips Using an Indentation Method (in a Well Plate System)

To assess the response of the tissue model samples to test agents, the resistance of the tissue samples to stretch is measured by a probe coupled to a force transducer. The stiffness of the tissue is related to the force required to move the probe by a specified amount once the probe contacts the tissue. The probe, consisting of a vertical glass tube whose tip has been smoothed by fire polishing, is attached to an isometric force transducer (described above). The diameter of the probe is about 2 to 3 mm and the shape of its tip can be flat or hemispherical. The probe is firmly attached to a beam and the beam attached to the force transducer by glue or wax (FIG. 11a). The force transducer is attached to a stationary frame. The 96-well plates are placed on a stage or holder that moves vertically. The stage constructed for demonstration of the method uses a micrometer driven by a computer-controlled stepper motor to raise or lower the stage at prescribed incremental rates. In this implementation the range of stage motion is 0 mm to 15 mm at a maximum velocity of 500 µm/sec. The same apparatus has been used for large-scale tissue mechanical measurements. A detailed description is provided below in the following section on force measurements.

Example 11

Measurements Using the Tissue Indentation Method (in a Well Plate System)

During the tissue formation and continued culturing of tissue models, the samples were kept in a 5% $CO_2$ incubator at 37° C. with bicarbonate buffered DMEM supplemented with 10% FBS, penicillin, and streptomycin. For force measurements the medium was changed to 150 µl of HEPES-buffered DMEM without serum. The temperature of the medium was kept at 37° C. by placing the wells on a heated plate connected to a temperature-controlled circulation bath.

The stage is raised until the probe tip touches the membrane or strip of reconstituted tissue. Contact of the tip with the sample is detected by a sudden increase in the force registered by the isometric force transducer. The stage is then lowered by 5 µm, i.e. tip is withdrawn from contact with the sample. Then the stage is moved vertically according to a saw-tooth wave-form at 3.3 µm/sec with 100 µm amplitude. During this trajectory the tip comes in contact with the tissue specimen and stretches it as the force is continually recorded by a data recorder. The velocity can be varied to optimize the sensitivity of measurements and to measure the viscosity of the sample.

After the peak force reaches its steady level the sample is stimulated with 20% Fetal Bovine Serum (FBS) (arrow a in FIG. 12a). This amount of FBS activates fibroblast non-muscle myosin producing a contractile force that stiffens the reconstituted tissues. About 10 min. after the FBS addition, there is a ~25% increase in the peak force of subsequent indentations (FIG. 12a). Nearly 15 min. after the addition to the medium of 40 nM CD (arrow b), the peak force from subsequent indentations has decreased about 40% from its initial level (FIG. 12). A further reduction of peak force was recorded 20 min. after addition of 2 µM CD.

A plot of force versus indentation depth during the membrane stretching follows a different path from that seen as the stress is relaxed by retraction of the probe from the sample, establishing a hysteresis area between the two curves. Upon addition of FBS or CD, changes in the hysteresis areas are compared in FIG. 12(b). Percent changes in the peak force and area of hysteresis for the experiment are compared in FIG. 13. The area of hysteresis changes to a greater extent upon stiffening due to myosin activation and CD addition. Therefore, the area of hysteresis is a more sensitive parameter than the peak force for monitoring the changes in mechanical properties of the sample.

Example 12

Figure 15:
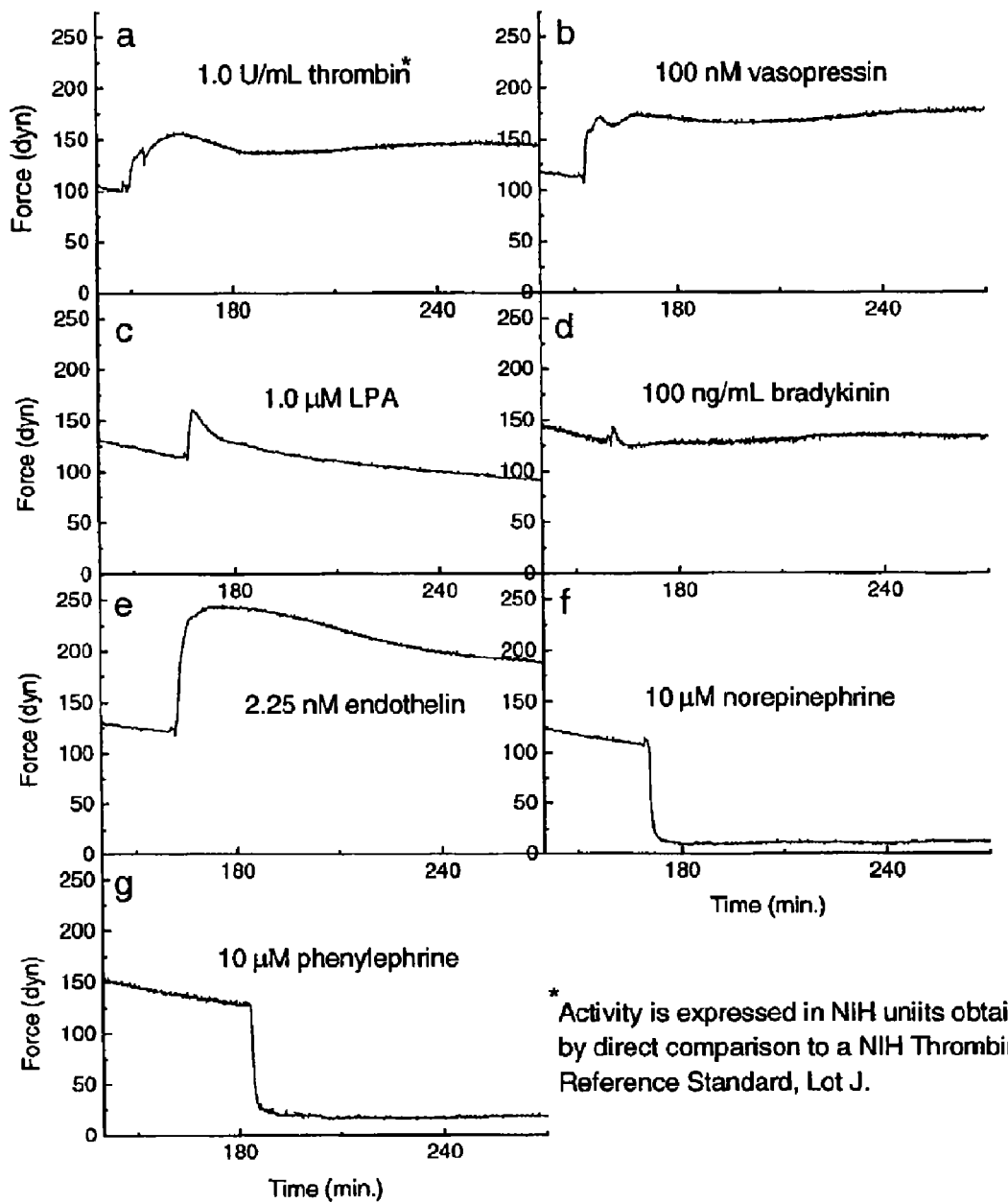
FIG. 15 shows the resulting forces (dynes) of a series of tests wherein several agonists are added to a tissue model of a ring system with smooth muscle cells. Panel a, b, c, d, e, f and g are profiles of force response by treatments of thrombin, vasopressin, LPA, bradykinin, endothelin, norepinephrine and phenylephrine, respectively.
Figure 16:
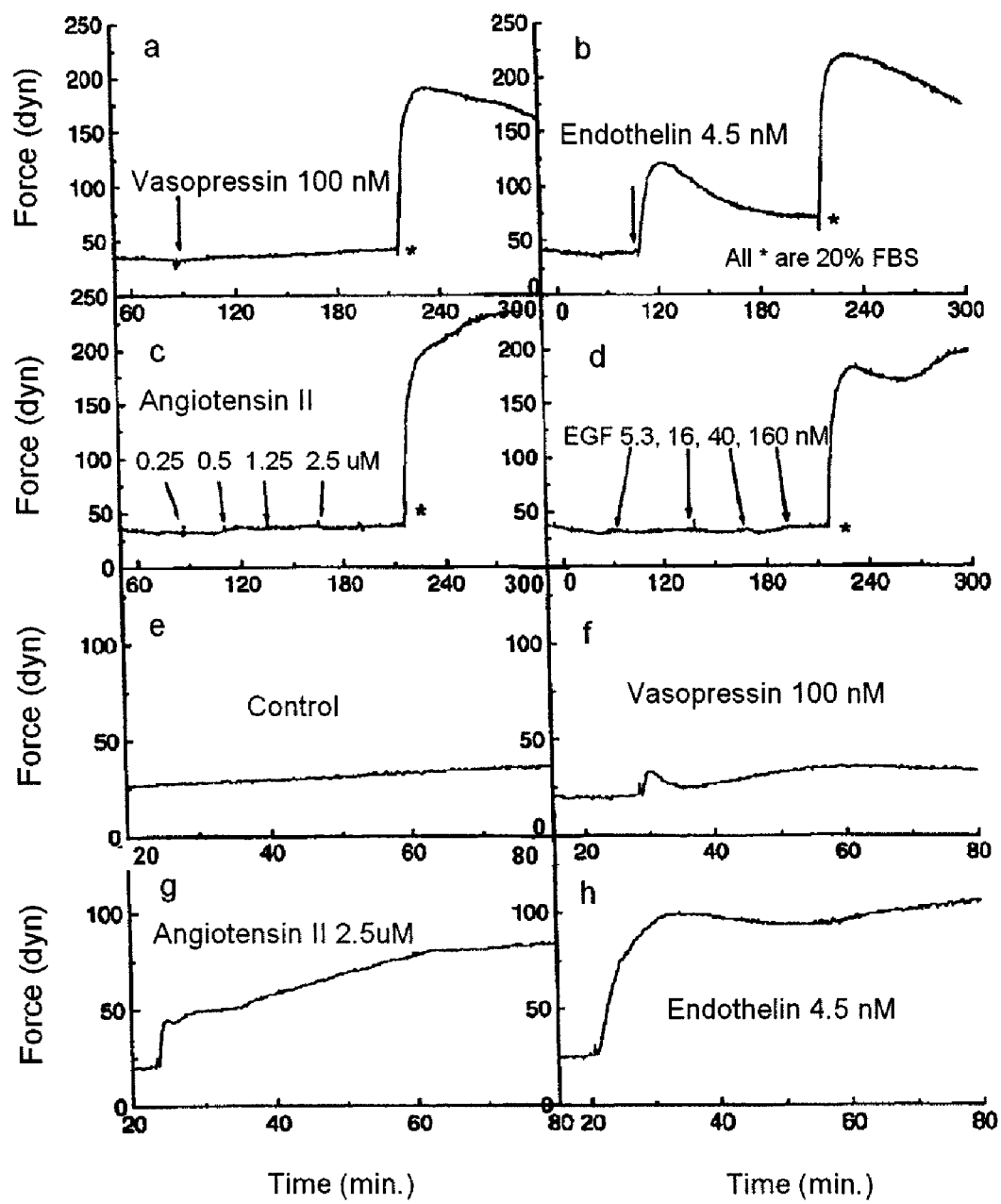
FIG. 16 shows profiles of contractile responses wherein a series of agonists were applied to a tissue model of a ring system made from chicken (panel a-d) and rat (panel e-h) cardiac fibroblasts, respectively.
Figure 17:
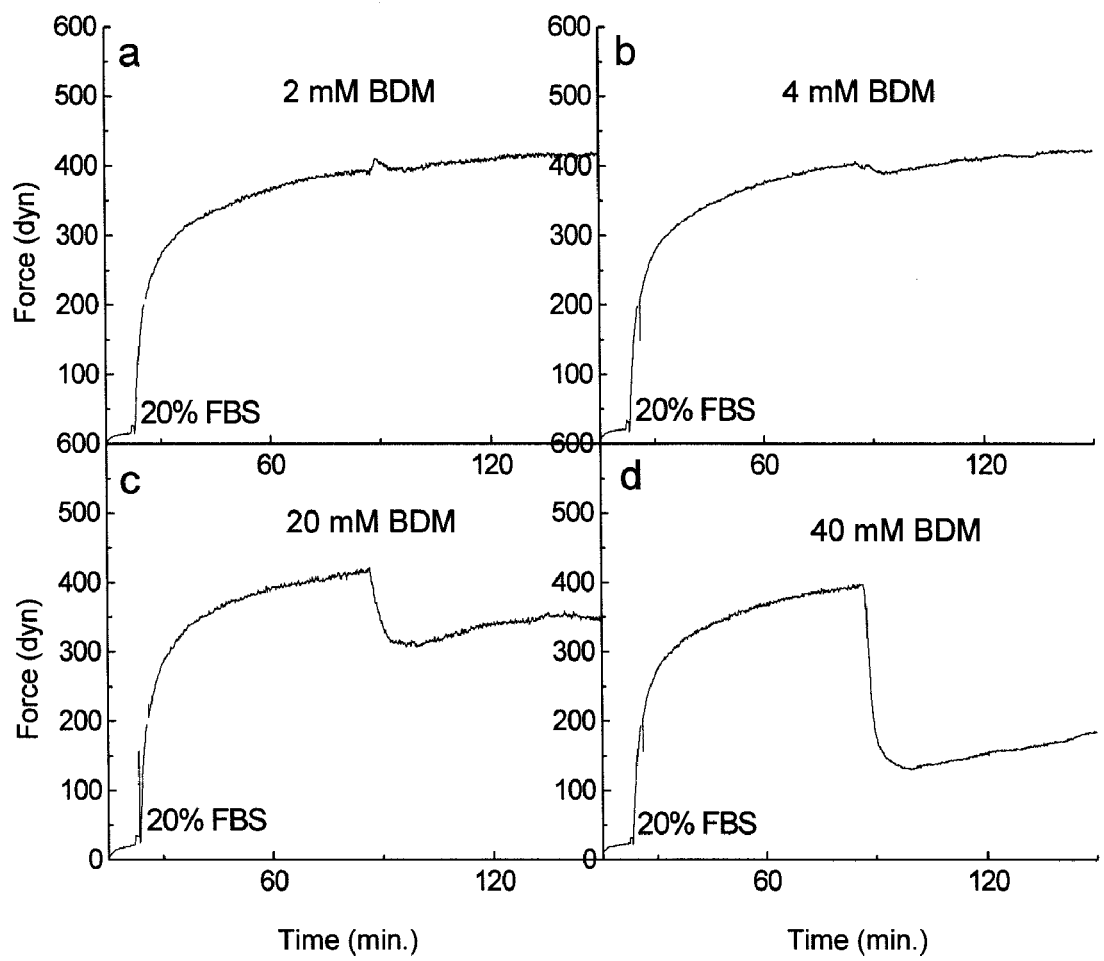
FIG. 17 shows a reduction in contractile force by inhibition of myosin contractility initially stimulated by 20% FBS.
Figure 18:
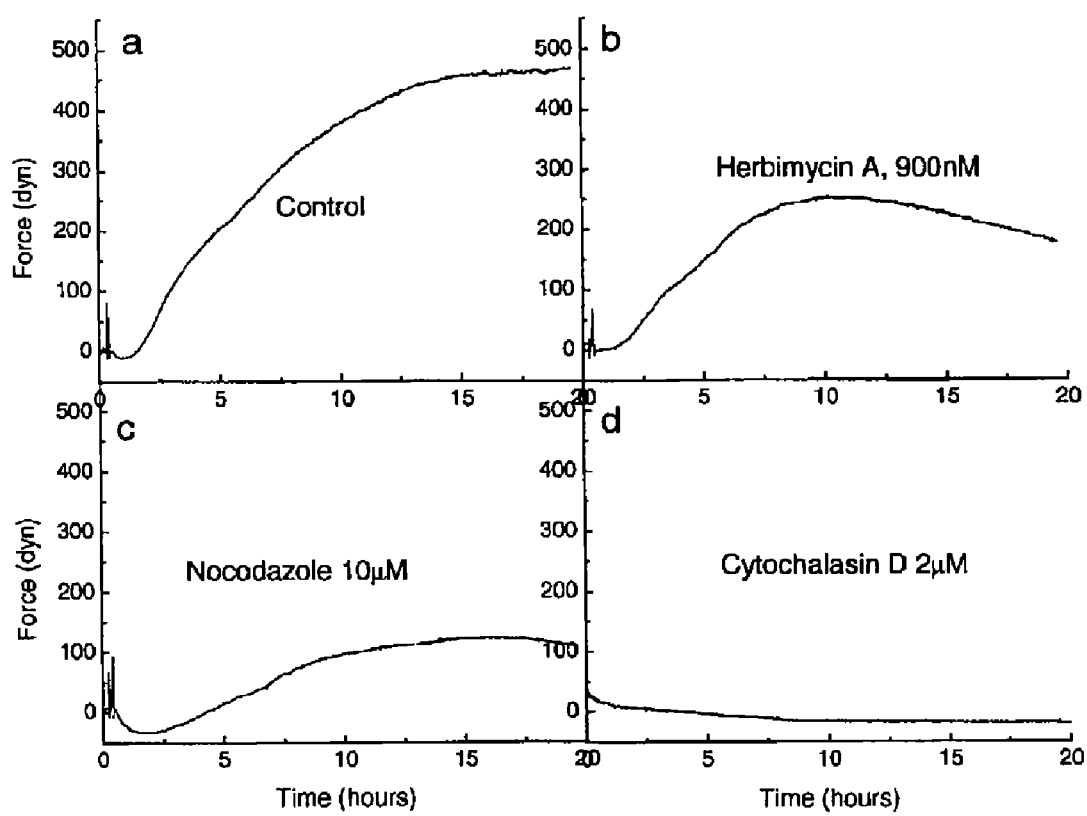
FIG. 18 shows a profile of the increase in contractile force during tissue development in a ring system treated with no chemicals (a), herbimycin A (b), Nacodazole (C), and cytochalasin (D). The ring was mounted on the force measuring system about one hour after gelation of the collagen and prior to significant remodeling and compression of the matrix by the cells.

Test Using Physiological Activators to Activate Force Response without Stretching Ring samples made using a rat embryo fibroblast derived cell line (REF52) were prepared as described previously herein. The length of the tissue was maintained at a constant level during the test. Each of the drugs indicated in FIG. 15 was added to a single tissue ring. Thrombin, vasopressin, lysophosphatidic acid (LPA), bradykinin, and endothelin contacted the ring to produce different forces that develop in different response times (FIG. 15). Norepinephrine and phenylephrine relaxed the contractility of the ring, and therefore norepinephrine and phenylephrine reduced the initial base line force of tissue indicated at the beginning of each test (FIG. 15) (reagents used were obtained from Sigma, St. Louis, Mo.).

Profiles of contractile response to different agonists applied to ring samples were made using chicken embryo cardiac fibroblasts (CECFs) and rat adult cardiac fibroblasts (RACFs) and are shown in FIGS. 16(a)-(d) and FIGS. 16(e)-(h), respectively.

RACFs responded to vasopressin (FIG. 16f) and angiotensin II (FIG. 16g) whereas CECFs did not response to vasopressin (FIG. 16a) and angiotensin II (FIG. 16c). CECFs did not respond to any dose of EGF stimulation (FIG. 16d). Endothelin stimulation contracted rings made using both CECFs (FIG. 16b) and RACFs (FIG. 16h). Time dependent force profiles after addition of FBS (20% v/v) were different depending on the pretreatment by different agonists.

For example, FBS addition resulted in a double peak of force after EGF pretreatment (FIG. 16d). The force level is sustained after FBS addition to a system previously treated with angiotensin II. Yet the force level started to decrease from its FBS stimulated peak level after treatment with vasopressin and endothelin (FIG. 16a, b).

In a related experiment, FBS was added to activate the contractile force and then a myosin ATPase inhibitor was added. The myosin ATPase inhibitor, BDM, reduced, in a dose dependent manner, (FIG. 17) the fully activated contractile force produced by prior addition of 20% FBS.

Thus the methods described herein are useful for managing the profiles not only of single compounds but also of combinations of multiple compounds applied at the same time or at different times. Managing profiles or combinations of multiple pharmaceuticals is useful both for screening purposes and also to reveal unexpected consequences caused by combinations of multiple pharmaceuticals.

The contractile force developed by the ring sample during matrix remodeling and compression can be measured by connecting the ring to the force measuring apparatus as described above within about 1-2 hours after collagen gelation. The cells begin to exert a force on the matrix after this time. Then the increase of force during tissue development (remodeling and compression) is observed over time.

A profile of force measured during the ring tissue development is shown in FIG. 18(a). Maximum force is typically reached within 15 to 20 hours. This process was also disrupted by several inhibitors as illustrated in FIGS. 18(b)-(d). The Tyrosine kinase inhibitor, herbimycin A (FIG. 18b) reduces the maximum force as does the microtubule disrupting reagent nocodazole (FIG. 18c). Cytochalasin D (2 µM) completely abolished the development of force from the beginning of the test.

This invention has broad utility including use for high-throughput pharmaceutical drug screening and treatment testing. For example, reconstituted tissues in the form of membranes or strips could be mass-produced to supply 96 uniform samples, one in each well of a 96-well plate. Simultaneous force measurements could also be achieved by using 4 or more force transducers (FIG. 11). The 96-well plate is placed on an x-y stage that positions the samples at the correct locations for the indentation measurements. Probes attached to force transducers move vertically to indent the samples (FIG. 11a). A single force transducer can be used to indent several samples within a short period of time by repositioning the 96-well plate using the x-y stage. The addition of chemical compounds and small peptides to the sample and movement of the stage and force transducers can all be automated and controlled by a personal computer. The computer also stores and analyzes the data in a database.

Example 13

Delivery of Genes and Proteins to the Cells as Agents within the Reconstituted Tissues Applications of the described method include testing procedures for delivering genes to cells. The reconstituted tissue samples can be made using cells lacking genes that contribute to cell and tissue mechanical properties. Hence, the recovery of normal tissue mechanical characteristics provides an assay for the effective delivery of the gene.

Figure 20:
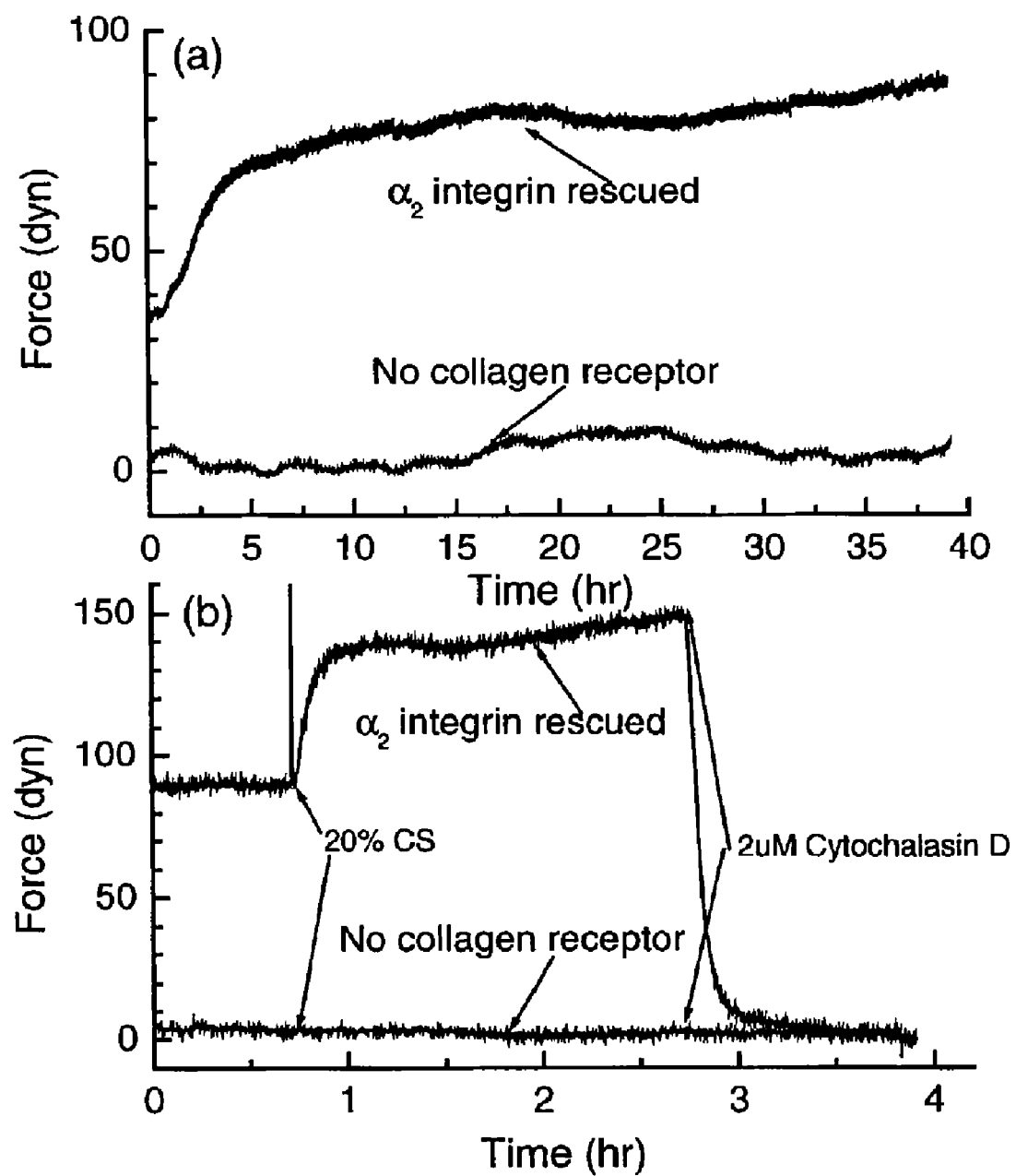
FIG. 20 shows that cells that lack the appropriate collagen-binding integrins can neither develop force during the period of tissue remodeling (FIG. 20a) nor in response to calf serum (FIG. 20b). These defects are corrected by restoring the missing subunit of the collagen binding integrin ($\alpha_2$).

The ring tissue model system can detect the effect of a genetic deletion on the ability of cells to generate force both while compressing and remodeling the collagen matrix and while responding to calf serum. Cells interact with and adhere to diverse ECM constituents through specific heterodimeric receptors called integrins on their surface membranes. Each integrin is composed of one α and one β subunit. The integrins that mediate binding to collagen are $\alpha_1\beta_1$ and $\alpha_1\beta_2$. NMuMG, is an immortalized but nonmalignant mouse mammary epithelial cell line that does not express $\alpha_1$, and $\alpha_2$ integrin. Hence, these cells interact weakly if at all with collagen matrices and therefore cannot transmit force to the ECM to generate and to maintain tissue stiffness. FIG. 20 demonstrates that cells without $\alpha_1$ and $\alpha_2$ integrin could not develop baseline force during tissue development nor could it respond to calf serum (CS) by increasing force (FIGS. 20a and 20b). Also shown is the rescue of these two functions by re-expressing normal $\alpha_2$. The cells containing the $\alpha_2$ gene normally adhered to and compressed the matrix and responded to CS (FIG. 20a, b). The methods are useful to manage the mechanical response profiles as indicators of genotype and to monitor the results of gene therapy, such as the efficiency of different methods of gene delivery.

Example 14

Pharmaceutical Candidate Testing

We demonstrated dose dependent stress relaxation of the tension in reconstituted tissues using Y27632, which has promise for the treatment of hypertension.

Figure 21:
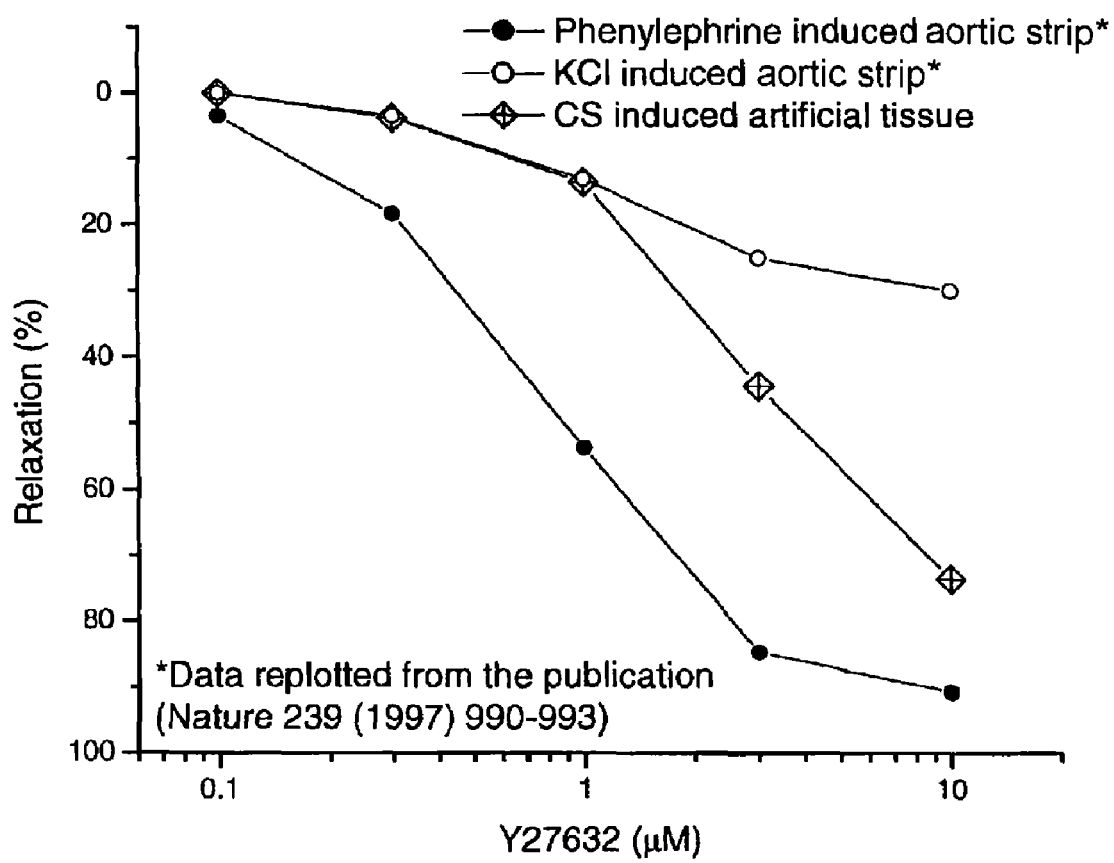
FIG. 21 is a comparison of the change in contractile force after treatment with various concentrations of Y27632, observed using tissue model and artic strips.

The connective tissue models made using NIH 3T3 cells were treated with different amounts of the candidate pharmaceutical, Y27632, a Rho kinase specific inhibitor, which has been tested for reducing tension of smooth muscle strips such as rabbit aortic rings (Nature 239 (1997) 990-993). It is one of the promising drug candidates for treating hypertension in the future. Depending on the agonists used to stimulate the tissue contraction, the degree of reduction in tension is different (FIG. 21). Y27632 reduces the tension of connective tissue models in a similar dose-dependent fashion (FIG. 21). Thus, the methods are useful for screening pharmaceutical candidates.

Figure 22:
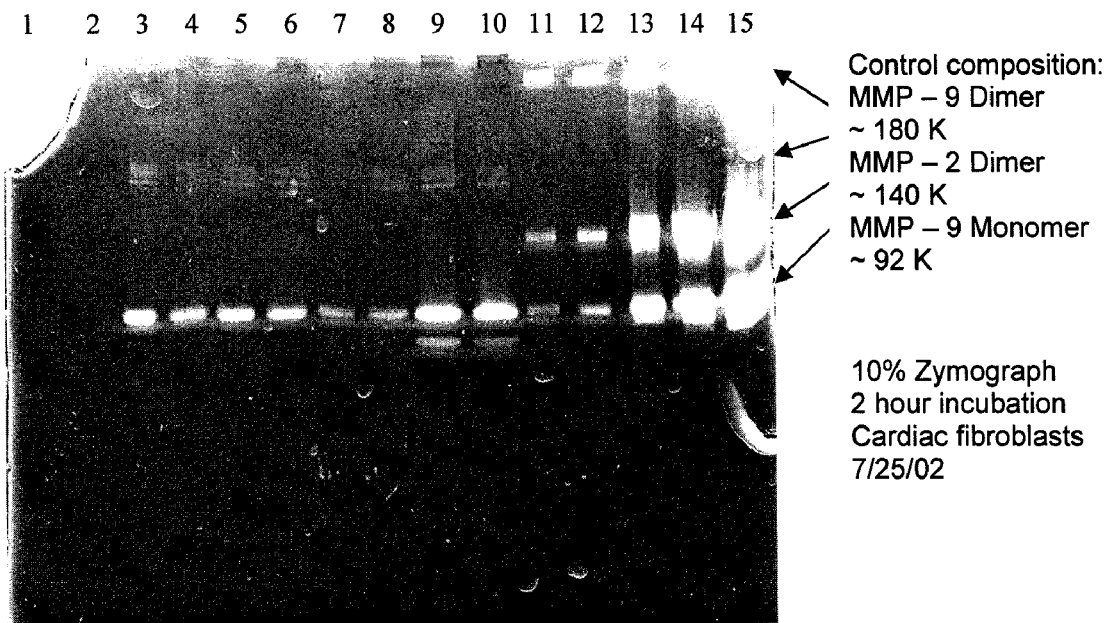
FIG. 22 shows a zymograph of MMPs secreted into the tissue culture medium by cells cultured in various conditions.
Figure 23:
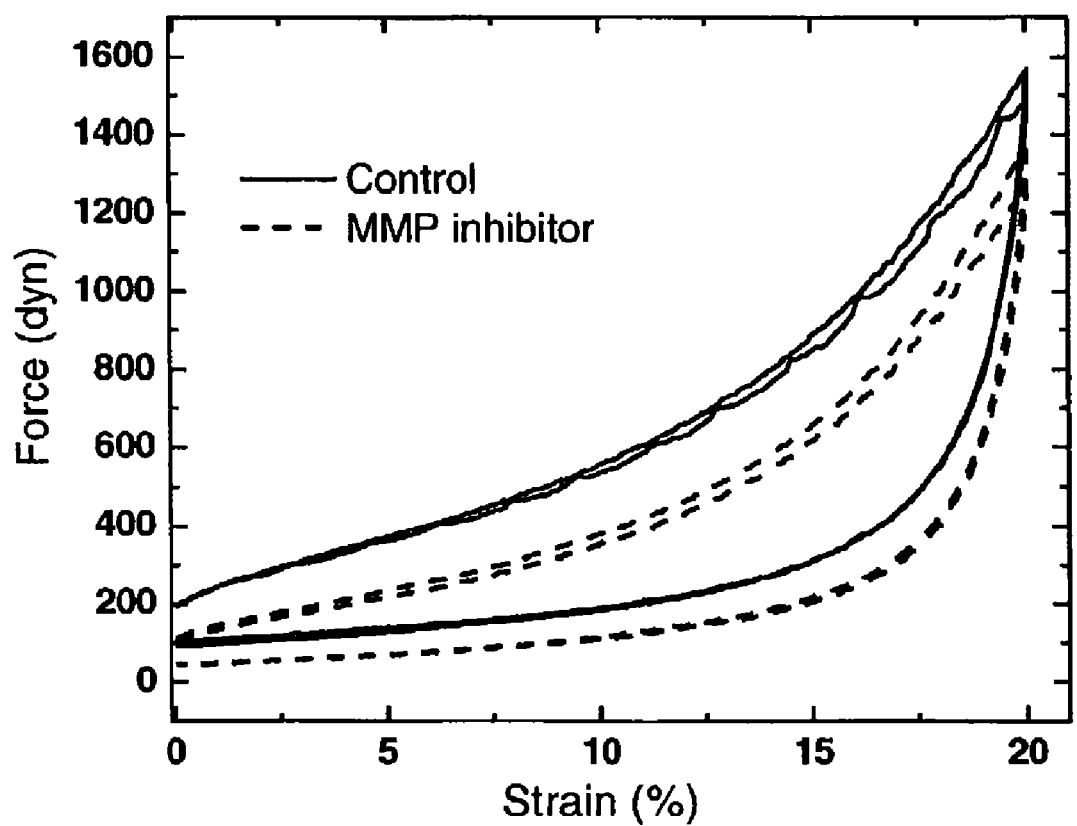
FIG. 23 compares force responses to stretch of tissue models cultured with and without MMP inhibitor GM6001.

The collagens in tissues are degraded and recycled by a family of enzymes called matrix metalloproteases (MMPs), which are secreted as latent proenzymes. The enzymes become active through proteolytic cleavage of their aminoterminal domain, and their activities depend on the presence of Zn++ and Ca++ MMP-2 activity is known to play a role in tumor cell invasion. The presence of MMPs both in pro- and active-forms is detected by a technique commonly known as zymography. Chicken cardiac fibroblasts are cultured for 2 days with DMEMs supplemented with none or 0.5% fetal bovine serum. MMP-2 and 9 are secreted by the cells into the medium and their presence is detected by the zymograph. In FIG. 22 the control lanes 11 through 15 are loaded with purified proenzymes of MMP-2 and 9. This shows that at least 0.5 ng of enzyme (lane 11) can be detected using the assay (FIG. 22). The smaller active enzyme runs ahead of proenzymes and a band of active enzyme appears at lower position than the band of inactive MMP-2. Medium conditioned by the cells growing on tissue culture dishes with no coating, or with fibronectin, or collagen coating do not show any bands of active enzymes. The medium conditioned by the cells grown in 3-D collagen matrix, i.e., tissue model, shows a band of active MMP-2 (lanes 9 and 10). This indicates that the cells on 2D substrata secrete inactive enzymes into the medium but they are not activated. The enzymes never get activated unless the cells are grown in 3 dimensional matrices. Therefore, the investigation of MMP activities affecting extracellular matrix degradation such as during tumor invasion requires a model system such as the tissue models in which the cells are growing in 3 dimensional matrices. This is especially important for discovering inhibitors of MMPs.

The effects of the general inhibitor of MMPs, GM6001 (Biomol Research Laboratories Inc. Plymouth Meeting, Pa.) (N-[(2R)-2-(Hydroxamid-ocarbonylmethyl)-4-methylpentanoyl]-L-tryptophan methylamide) on the mechanical properties of artificial tissues have been investigated. The tissue models made using cardiac fibroblasts are incubated with 50 .µM GM6001 for 6 days. The tissue culture medium is replenished every other day with fresh medium containing GM6001. The tissue model rings were subjected to mechanical tests as described above. The GM6001 treated samples (dash lines in FIG. 23) show significant reduction in mechanical properties of the samples compared to those of controls (solid lines). Although the Ki values of GM6001 for different MMPs are around nmol/l, the effects of GM6001 in animals can be observed only with a high concentration of the inhibitor (sub mmol/l) (Circ Res January 1996; 78(1):38-43). This suggests that the Ki value measured in a purified system does not directly correlate to the inhibitory effect of drug in living test subjects such as animals or tissue models. MMP inhibitors affecting the mechanical properties of various tissue models can be discovered efficiently using the high throughput system.

Possible Parameters to Analyze Curves

Figure 24:
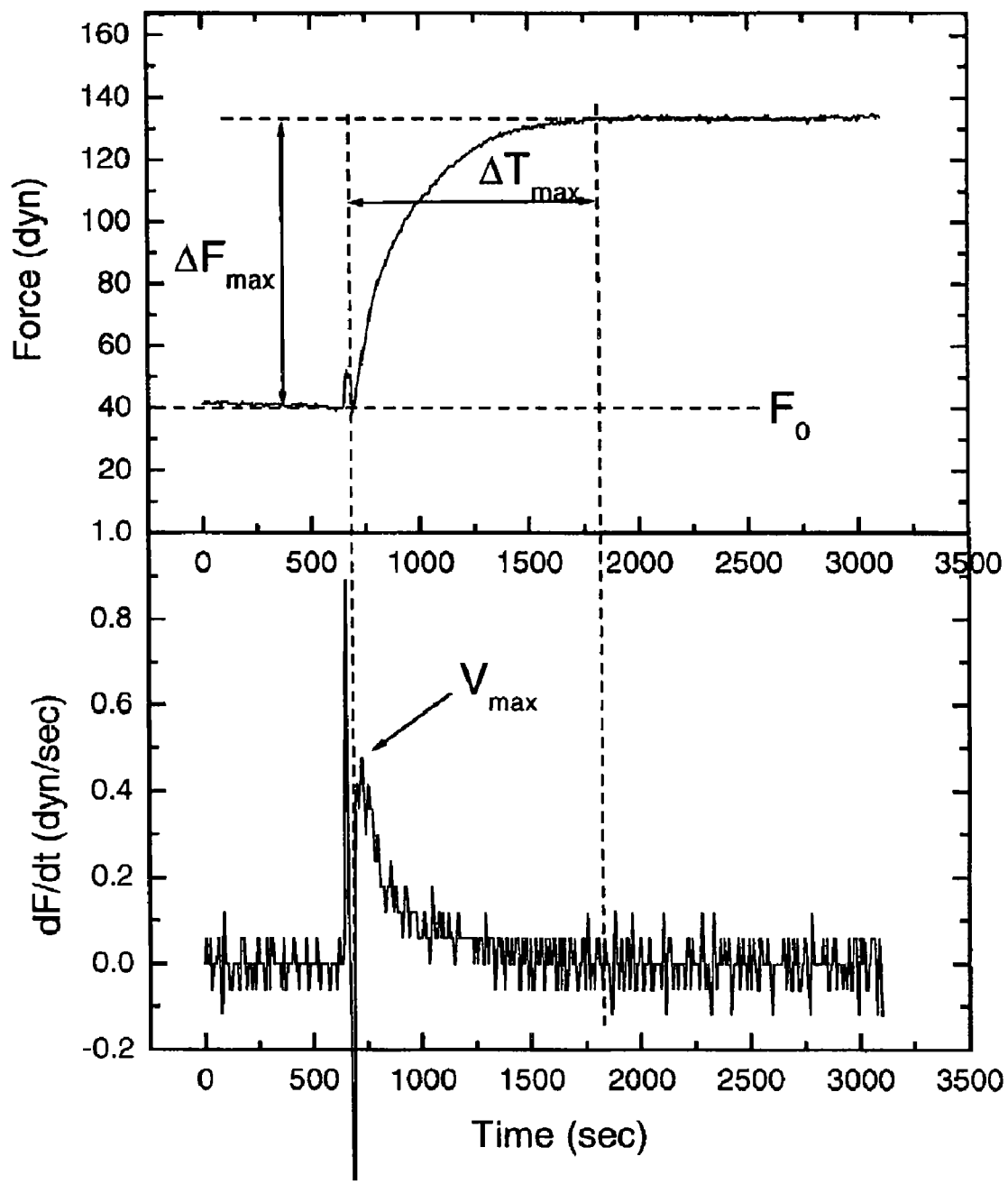
FIG. 24 illustrates the parameters by which the change in force recorded over time in response to various treatments can be represented.

The force response initiated by an agonist addition plotted over time can be presented using several parameters to describe the shape of the curve. The $F_0$ and $\Delta$Fmax represent the initial force level before the agonist addition and the maximum change in force respectively. The $\Delta$Tmax represents the time to complete the change in force level. The time derivative of the force curve represents the velocity of the change of force with time. The maximum value of dF/dt, Vmax, represents a maximum slope in the force curve. These parameters are useful to make a profile of pharmaceutical candidates in terms of the changes in the tension level of the artificial tissues (FIG. 24).

The profile of a candidate pharmaceutical is compared to the profile of a known pharmaceutical and a ranking or rating is made based on that comparison to provide information and guidance as to whether the candidate pharmaceutical would likely be an effective pharmaceutical.

Further, if desired, a test is carried out in accordance with this invention, wherein the candidate pharmaceutical is evaluated against a particular cell system which is known to be involved in a particular disease. In this embodiment, the cellular response thereto using the system of this invention is employed to provide an indication of the probable activity of the candidate pharmaceutical on a particular cell type. In a further embodiment, the pharmaceutical is evaluated in a tissue model system and compared to the evaluation of a pharmaceutical known to be useful in treating a particular disease.

In a further embodiment, the profile of the known pharmaceutical is one which is known to provide effective treatment against a known disease. In this embodiment a comparison is thus made wherein the pharmaceutical is evaluated against cells which are known to be involved in a particular disease. This embodiment is useful in determining whether a pharmaceutical is potentially useful in the treatment of heart disease or hypertension or aging for example.

Hypertension is caused by elevated contractility and stiffness of blood vessels. Drugs for hypertension can be identified using this invention. These drugs can be used to lower the blood pressure of the animal or tension and stiffness of isolated blood vessels from the animal. This invention uses artificial tissues mimicking blood vessels using tissue culture cells and extracellular matrices, the method herein can replace animal models or explanted tissues.

Artificial tissues are made to mimic specific biological functions or different types of organs and tissues including skin, muscle, heart, and blood vessels or to mimic more complex tissues by co-culturing different cell types in a single artificial tissue. Since the mechanical properties of the tissues are correlated to their structural integrity by using this invention, they are important parameters to indicate biological functions of tissues and organs.

In addition, the present invention may be suitably used to screen compounds at high speed based on their biological activities affecting the mechanical properties of the artificial tissues. For example, artificial tissues are made in small sizes to fit in one of the wells (4 mm in diameter and 6 mm in height) in a 96-well plate. The significantly miniaturized sample preparation reduces the amount of compounds used in each testing at least by 90% compared to known methods, such as using aortic rings. Since animal tissues are surgically isolated from animals, their sizes and responses to the drugs are not necessarily reproducible.

Toxicity of pharmaceutical compounds can be determined using the method of this invention. For example a different dose of ethanol causes a decrease in the level of baseline force maintained by the viable cells.

In another aspect, the biochemical properties of cells and matrices comprising model tissue are measured optically using, for example, fluorescence markers.

Using the present invention, one can create a new library of profiles of pharmaceuticals based on their effect on the mechanical properties of live artificial tissues. The number of active compounds in the library created by the instant invention using the indentation system is most likely to be less than that in the library created by a prior art test tube based screening system. Compounds selected in chemical screening procedures may include many that elicit no physiological response.

The chemical compounds screened by the artificial tissues based system will have a higher chance of having similar effects on the mechanical properties of real tissues and organs in animals and humans. Therefore, the use of animal models for an optimization stage of drug screening can be significantly reduced using the artificial tissue based high throughout screening. The invention can replace animal testing by providing a physiological response system assembled from cultured cells.

In an aspect, the results of screening are employed to identify and advance one or more candidate pharmaceuticals or drugs to an advanced stage of testing or evaluation, including possibly commercialization. In another aspect, the results of screening are employed to terminate or alter further testing or screening on a pharmaceutical or drug candidate. In another aspect, the method and apparatus described herein are used to evaluate and validate the target or locus for the drug or pharmaceutical candidate.

Example 15

Reproducibility of Mechanical Measurements with High-Throughput System

Cell and Tissue Culture

Bio-artificial tissues were generated by mixing cells and neutralized collagen, as described elsewhere (Wakatsuki et al., 2000, Biophys. J. 79:2353-2368). Briefly, cells were mixed with neutralized rat-tail collagen (Millipore Billerica, Mass.) and media containing 10% Fetal Bovine Serum (FBS). 200-250□1 of this solution is poured into wells as described below. The tissues are cultured in Dulbecco's modified Eagle's medium (DMEM) supplemented with 10% FBS and antibiotics (penicillin and streptomycin) in an incubator for two or three days. The bio-artificial tissue membrane was stretched using a mechanical testing device is (as detailed below). During the mechanical measurements, culture medium was switched to a HEPES-buffered DMEM, pH 7.4, and maintained at 37° C.

Cells used in this study included: (1) rat embryo fibroblasts (REF52 cell line) maintained in DMEM supplemented with 10% FBS split once a week (kind gift from Dr. Wysolmerski, Department of Neurobiology and Anatomy, West Virginia University School of Medicine), (2) chicken embryo fibroblasts (CEFs) isolated from 10 day old chicken embryos using a previously described protocol (Wakatsuki et al., 2000, Biophys. J. 79(5):2353-2368) maintained in DMEM supplemented with 3% FBS (passage 2 to 5), and (3) smooth muscle cells (SMC) isolated from adult rat aorta using a previously described protocol (Griendling et al., 1991, J. Biol. Chem. 266(23):15498-15504) cultured in DMEM supplemented with 10% FBS and 1% L-glutamate (passage 10-12).

Chemicals

To either inhibit or enhance cell-force generation in bio-artificial tissues, several chemicals and hormones were used during the mechanical tests. To reach the concentrations specified, appropriate amounts of stock solution of the chemicals were added to the media in which the bio-artificial tissues were immersed. The concentrations of stock solution prepared for the study were 4 mM, 10 mM, 50 µM for cytochalasin D (CD), norepinephrine, and endothelin-1, respectively. Dimethyl sulfoxide (DMSO) was used as a solvent. All the materials were purchase from Sigma Chemicals (St. Louis, Mo.) unless specified.

Tissue Chambers

A chamber to hold 8 bio-artificial tissues was machined from a polycarbonate bar (25×60×10 mm) using a tabletop CNC mill (Sherline Products Inc., Vista, Calif.). The 8 square wells of 8×8 mm contained 2 horizontal stainless-steel (medical grade) bars (1 mm diameter) which centers were located 2 mm above bottom and 2 mm beside each wall and were 4 mm apart (FIG. 29A). A microscope cover-slip (No. 1 thickness, Fisher brand) sealed the bottom of wells using silicon glue (Dow chemicals) to facilitate microscopic imaging of cells and bio-artificial tissues. A pre-polymerized solution of bio-artificial tissues was poured into the wells until the horizontal bars became immersed to half of its depth. During tissue culture, the solution gelled and entrapped cells that remodeled and compacted the gel (Tranquillo, 1999, Biochem. Soc. Symp. 65:27-42) by cell traction force. By the next day, the bio-artificial tissues detached from the bottom and side wall to form a membrane spanning between the two bars. The bio-artificial tissues stiffened to form a thin layer of tissue overlaying the bars and generated active tension within the bio-artificial tissues. The chambers were sterilized by UV before usage and kept in a 100 mm sterile Petri dish to avoid any contamination.

Testing Device

The mechanical testing device is depicted in FIG. 29A. A horizontal linear actuator (FIG. 29A-a, ER32-SRN300A, Parker, Wadsworth, Ohio) automatically places the center of each well at right angles below a force-probe (FIG. 29A-c). The bottom of L-shaped probe indents and bends the bio-artificial tissues at the middle (FIG. 29D). The other end of the probe is connected to an isometric force transducer (FIG. 29A-b, model 52-9545, Harvard Apparatus, South Natick, Mass.) and moved by a vertical linear actuator (FIG. 29A-a, ER32-SRN100A, Parker, Wadsworth, Ohio). During the tests, the temperature of bio-artificial tissues in the wells was maintained at 37° C. using a water jacketed warm plate (FIG. 29A-e) connected to a circulating water bath (HAAKE C10-P5, Thermo Fisher Scientific, Inc. Waltham, Mass.). The linear actuators were controlled simultaneously by a personal computer that also recorded the signal generated by the force transducer. The bio-artificial tissues can be quickly placed in a holder at its designated position for mechanical measurements. A time dependent function to lengthen and shorten bio-artificial tissues was predetermined using the computer software of the device. The device was placed in a laminar flow hood to avoid contamination during tests. Therefore, the mechanical measurements can be repeated on the same set of bio-artificial tissues several times over the course of hours, days, or weeks.

Reproducibility of Mechanical Measurements

To achieve the mass-production of bio-artificial tissues with reproducible tissue mechanics is a crucial step towards the high throughput applications of this technique. A typical force-time plot after two preconditioning stretches demonstrated high reproducibility of bio-artificial tissues mechanics by an almost indistinguishable 4 force-curves obtained from 4 different bio-artificial tissues (FIG. 30A).

Data Analysis

While the force-probe indents the bio-artificial tissues vertically at a constant rate, v (0.5 mm/sec), an isometric force transducer connected to the force probe recorded a resistance force, F(t). A time dependent change in bio-artificial tissues-membrane force in the longitudinal direction, T(t), was calculated from F(t) by a trigonometric relationship (FIG. 28). This rate of indentation was determined to achieve a minimum noise-level by the current device arrangement. When the probe was advancing, the bio-artificial tissues-membrane was indented d(t) (=vt) vertically by the L-shaped probe. As a result, the bio-artificial tissues-membrane was stretched $\Delta L(t)$ longitudinally from its initial length $L_o$. To characterize the material properties of bio-artificial tissues, strain, $\epsilon(t)$, and stress, $\sigma(t)$, were computed by normalizing $\Delta L(t)$ and $F(t)$ with $L_o$, and the cross-sectional area of the bio-artificial tissues-membrane, A, respectively. The strain was expressed as a function of d(t) by $$\varepsilon(t) = \frac{\Delta L(t)}{L_o} = \sqrt{L_o^2 + (2d(t))^2} - L_o = \sqrt{1 + \left(\frac{2d(t)}{L_o}\right)^2} - 1. \quad (1)$$

The stress was also expressed as function d(t) and F(t) by $$\sigma(t) = \frac{T(t)}{A} = \frac{F(t)}{2A\sin\alpha} = \frac{F(t)\sqrt{1 + \left(\frac{2d(t)}{L_o}\right)^2}}{2A\frac{2d(t)}{L_o}}, \quad (2)$$

where $\alpha$ is a small angle between the membrane and horizontal plane. While $(2d(t)/L_o)$ is reasonably small (<0.5), strain and stress can be expressed simply:

$$\varepsilon(t) \approx \frac{1}{2}\left(\frac{2d(t)}{L_o}\right)^2 = 2(\Delta Z(t))^2 \text{ and} \quad (3)$$

$$\sigma(t) \approx \frac{F(t)}{2A\left(\frac{2d(t)}{L_o}\right)} = \frac{F(t)}{4A\Delta Z(t)}, \quad (4)$$

where $\Delta Z(t) = d(t)/L_o$. \quad (5)

Fitting Experimental Data

A translation of raw data into physically meaningful parameters, such as stiffness and active pretension allowed us to compare experimental results. The experimental data was fitted to a simple mechanical model. Based on experimental observations (FIG. 30E), we can assume that for small strain, at constant strain rate, the tissue behaves like an isotropic linear elastic material with modulus of elasticity, E, and with a pre-stress, $\sigma_0$. Under these conditions, the stress measured at various strain levels depends linearly, i.e.;

$$\sigma = E\epsilon + \sigma_0. \quad (6)$$

Combining Eq. 6 with Eq. 3 and 4, while satisfying, $2d(t)/L_o<0.5$, we can write the measured poking force as:

$$F(t) = 4\sigma_0 A\Delta Z(t) + 8EA(\Delta Z(t))^3 \quad (7)$$

The slope of the curves (dF(t)/dt) changed suddenly when the force-probe touched the bio-artificial tissue membrane. The force recording included a period before the probe touched the bio-artificial tissue surface at $t=\tau$. Since Eq. 7 represents F(t) only after the membrane indentation, a more general expression, $$F(t) = 4\sigma_0 A\Delta Z(t-\tau) + 8EA(\Delta Z(t-\tau))^3 \text{ for } t \geq \tau \text{ and } F(t) = 0$$
$$\text{for } t < \tau \quad (8)$$

was used to fit F(t) to the data. Then, the stiffness, EA, the pre-force, $\sigma_0 A$, and time offset, $\tau$, was estimated (FIG. 30B).

FIG. 30A is a graph showing typical data of four independent force measurements from four individually prepared bio-artificial tissues and illustrates the reproducibility of measurements. FIG. 30B is a graph showing an example of the data fitting to a simulation for estimating $\sigma_0 A$, EA, and $\tau$. The regression ($R^2$) indicates how well the curve fit. FIG. 30C is a graph showing results when different ETs were treated with 0, 90, 2000 nM (dots, dash, line, respectively) concentrations of cytochalasin D (CD). The higher concentration of CD reduced the resistant force, F(t) detected by the force transducer compared to that of the control. FIG. 30D is a graph in which the force-time plots of FIG. 30C were converted to longitudinal force, T(t) vs. strain plots. The conversion made the curves close to straight lines especially at low strain. The CD treatments shifted the curves down, but the slopes were maintained. Data close to zero strain was not shown (due to a large amount of noise at low force levels due to the abrupt changes from 0 force). FIG. 30E is a graph showing simulated data corresponding to a model described in the Examples. Decreases in pre-force $\sigma_0 A=0$, 0.25, and 0.5 (dots, dash, line, respectively), EA=4, and $\tau=5$ simulated typical changes in force-time curves observed in FIG. 30C. FIG. 30F is a graph showing that the converted longitudinal force-strain curves also reproduced the changes shown in FIG. 30D by the CD treatments.

FIG. 30C-E demonstrated the applicability of the data analysis. The bio-artificial tissue mechanical properties were decreased by partially and completely disrupting the actin cytoskeleton with 90 nM and 2 µM cytochalasin D (CD), respectively. As a result, F(t) with CD were shifted down to produce less resistance force while stretching the bio-artificial tissue membrane. The bio-artificial tissue produced less force and showed a smooth transition from an undetectable to detectable force level, which was harder to determine $\tau$ (FIG. 30C). The bio-artificial tissues were remodeled and stored pre-stress, $\sigma_0$, longitudinally in the membrane during its development. When F(t) curves were converted to the longitudinal force, T(t) using Eq. 1 and 2, the bio-artificial tissues treated with 90 nM and 2 µM CD clearly showed reduced levels of $\sigma_0 A$ (minimum force) to compared to their untreated control (FIG. 30E). The slopes of the curves, however, did not change significantly. Series of simulated curves with different values of $\sigma_0 A$ using Eq. 7 predicted the shape of both F(t) and T(t). During the engineered-tissue development, the cells remodeled ECM using the cell traction force (Zahalak et al., 2000, Biophys. J. 79(5):2369-2381). The stiffness of the bio-artificial tissue observed by the small stretching was not affected by the reduction of cellular contractile force with CD treatments bearing on the F-actin network. The estimated sample stiffness, EA, mainly depends on the state of ECM stiffness rather than active cell force. The curve fitting to the data in FIG. 30D showed that the linear model (Eq. 8) was valid up to strains of ~6%. For curve fitting, only data points collected at less than 6% strain were used. Therefore, this expression provides good estimates for the tissue stiffness at relatively small strains. However, a nonlinear model (e.g., Freudenthal, 1966, *Introduction to the mechanics of solids*, Wiley, N.Y.) was required for considering the nonlinear effects observed in the longitudinal force-strain plot at higher strain (>~6%).

Number of ET Indentations and Estimated Parameters

Figure 31:
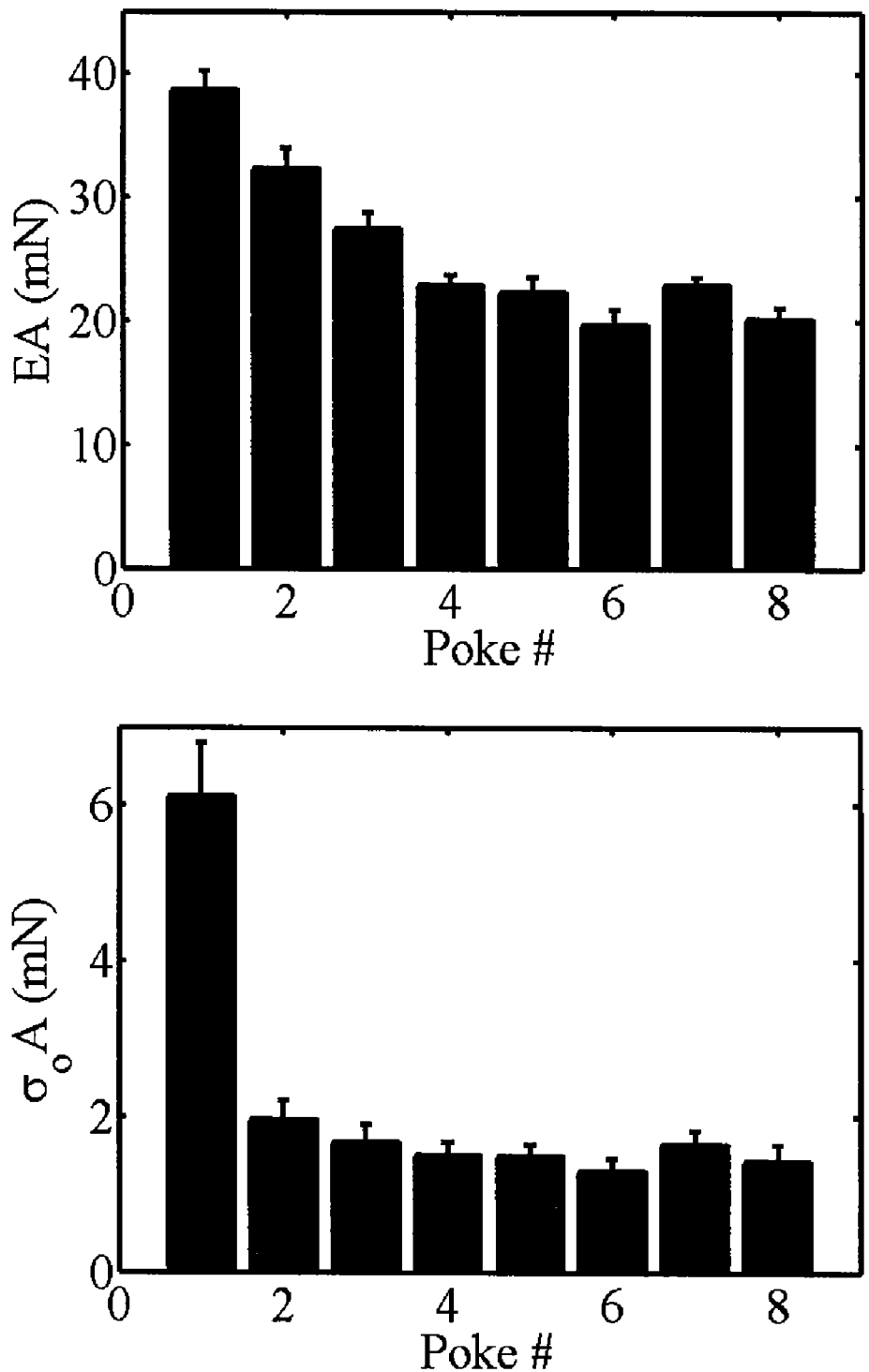
FIG. 31 is a set of graphs showing the effects of preconditioning on EA (tissue stiffness) and $\sigma_o A$ (active cell force) on bio-artificial tissues including rat embryo fibroblasts. The upper graph of FIG. 31 is a graph showing tissue stiffness changed significantly after poke #4. The lower graph of FIG. 31 is a graph showing that active force did not change significantly after poke #2. Data shown is the average of 8 datasets from 8 different bio-artificial tissues. (Bars=s.e.)

To achieve reproducible mechanical measurements of almost all the biological tissues tested, the tissues were preconditioned by stretching the samples several times prior to the measurements. The effects of preconditioning by the preconditioning indentations on the bio-artificial tissues mechanics were analyzed using the bio-artificial tissues with rat embryo fibroblasts. The freshly prepared bio-artificial tissues were kept in DMEM containing 3% FBS for 2 days and switched to serum-free DMEM 16 hours before the testing. Each bio-artificial tissues was indented vertically 8 times consecutively resulting in 20% longitudinal stretches. The tissue stiffness (EA), active cell pre-force ($\sigma_0 A$) and time delay, $\tau$, were calculated using the protocol described above. The tissue stiffness was gradually reduced until the fourth indentation, while the active force became stable after the second indentation (FIG. 31). No appreciable change in $\tau$ during the repetitive indentations indicated that the deformation of bio-artificial tissue was recovered quickly in-between the indentations. Most of the experiments described in the following sections were performed after 3 or more preconditioning indentations. The experiments detecting only cellular contractility used 1 preconditioning to reduce the total experiment time. The bio-artificial tissues without any treatments were always included as a control group to monitor changes in the bio-artificial tissues mechanics by the series of indentations.

Example 16

Detection of Effects of CS on Cellular Mechanics

The sensitivity of mechanical measurements for detecting integrity of F-actin network modulated by well known disrupter, cytochalasin D was tested. The effects of CD on bio-artificial tissues were characterized by measuring the changes in stiffness and cell force. We previously analyzed the effects of different CD concentrations on the mechanical properties of ring shaped bio-artificial tissues (as depicted in FIG. 1). The force measurement apparatus used for the bio-artificial tissues rings was previously used to measure contractility of aortic rings. In the ring system, the direction of contractile force is parallel to the direction of stretching the ring. The objective of this study was to compare the results from the ring system with those measured using the tissue indentation device.

Figure 32:
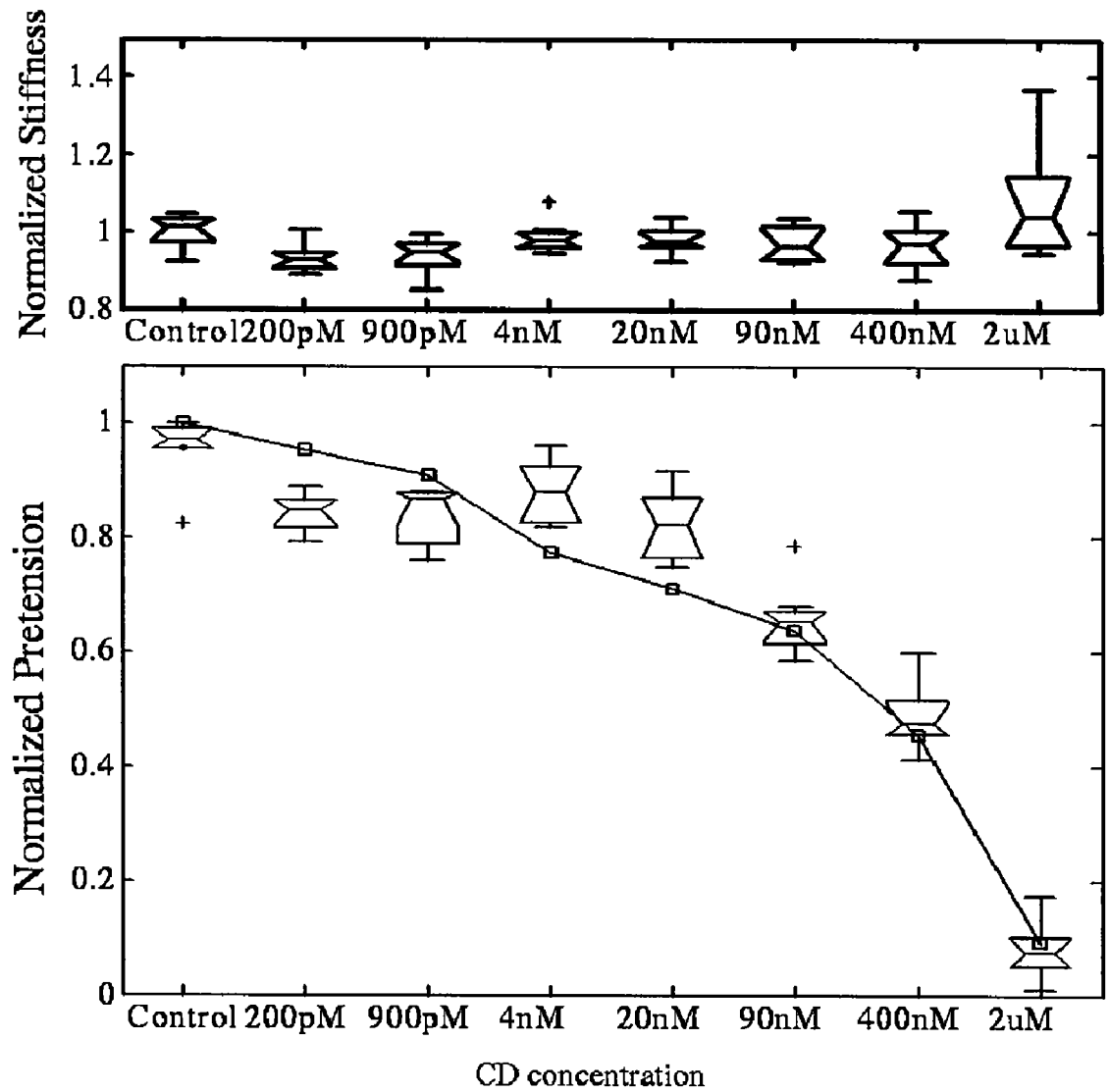
FIG. 32 is a set of graphs illustrating the effects of Cytochalasin D (CD) treatments on bio-artificial tissues including chicken embryo fibroblasts. (plus=outlier).

Following the 7 preconditioning stretches, different CD concentrations were prepared (200 pM, 900 nM, 4 nM, 20 nM, 90 nM, 400 nM and 2 μM) to test 4-6 bio-artificial tissues in each condition. The control measurements of stiffness demonstrated a great consistency among the bio-artificial tissues (Table 1). The ratios of active cell forces (CD treatment over control) were plotted against the 8 different CD concentrations as shown in FIG. 32. Two hours post-treatment, 8 samples for each CD concentration were acquired (total of 64 samples). The square dot with line represents published data from previous work (Wakatsuki et al., 2001, J. Cell Sci. 114:1025-1036) which was obtained from ring-shaped tissues. A similar plot for tissue stiffness shows no change with CD treatments (FIG. 32). The ratio between the active cell forces generated by treated and untreated tissues was used as a better estimate for the effect of CD on bio-artificial tissue mechanics. The active cell force computed by fitting the force measurements to Eq. 8 yielded very high correlation factors, $R^2 > 0.97$, for each concentration of CD. The CD concentration-dependent reduction in pre-force exhibited a profile almost identical to that observed previously (Wakatsuki, et al., 2001, J. Cell. Sci. 114:1025-1036) (FIG. 32 bottom), which validated the use of miniaturized bio-artificial tissues for detecting cellular mechanics. The EA, indicating the mechanical properties of extracellular matrix (ECM), however, did not change at all after the CD treatment.

TABLE 1

The stiffness of bio-artificial tissues before Cytochalasin D (CD) treatment ($EA_{CT}$), the ratio of post- over pre- CD treated stiffness ($EA_{CD}/EA_{CT}$), and height difference in sample surface height between post- and pre- CD treated samples.

| [CD] (nM) | $EA_{CT}$ (mN) | $EA_{CD}/EA_{CT}$ | $z_{CD}$-$z_{CT}$ (μm) |
|---|---|---|---|
| 0 (control) | 11.993 ± 0.275 | 0.999 ± 0.015 | −7.718 ± 5.506 |
| 0.2 | 10.692 ± 0.211 | 0.932 ± 0.013 | −8.925 ± 9.257 |
| 0.9 | 10.896 ± 0.436 | 0.938 ± 0.016 | −21.761 ± 8.982 |
| 4 | 10.973 ± 0.278 | 0.986 ± 0.015 | −23.707 ± 13.222 |
| 20 | 10.770 ± 0.344 | 0.979 ± 0.013 | 4.550 ± 7.653 |
| 90 | 11.276 ± 0.371 | 0.970 ± 0.016 | −22.054 ± 12.989 |
| 400 | 11.515 ± 0.351 | 0.964 ± 0.021 | −17.607 ± 6.533 |
| 2000 | 12.279 ± 0.148 | 1.077 ± 0.050 | −35.318 ± 15.189 |

Example 17

Detection of Mechanical Changes in ECM

Figure 33:
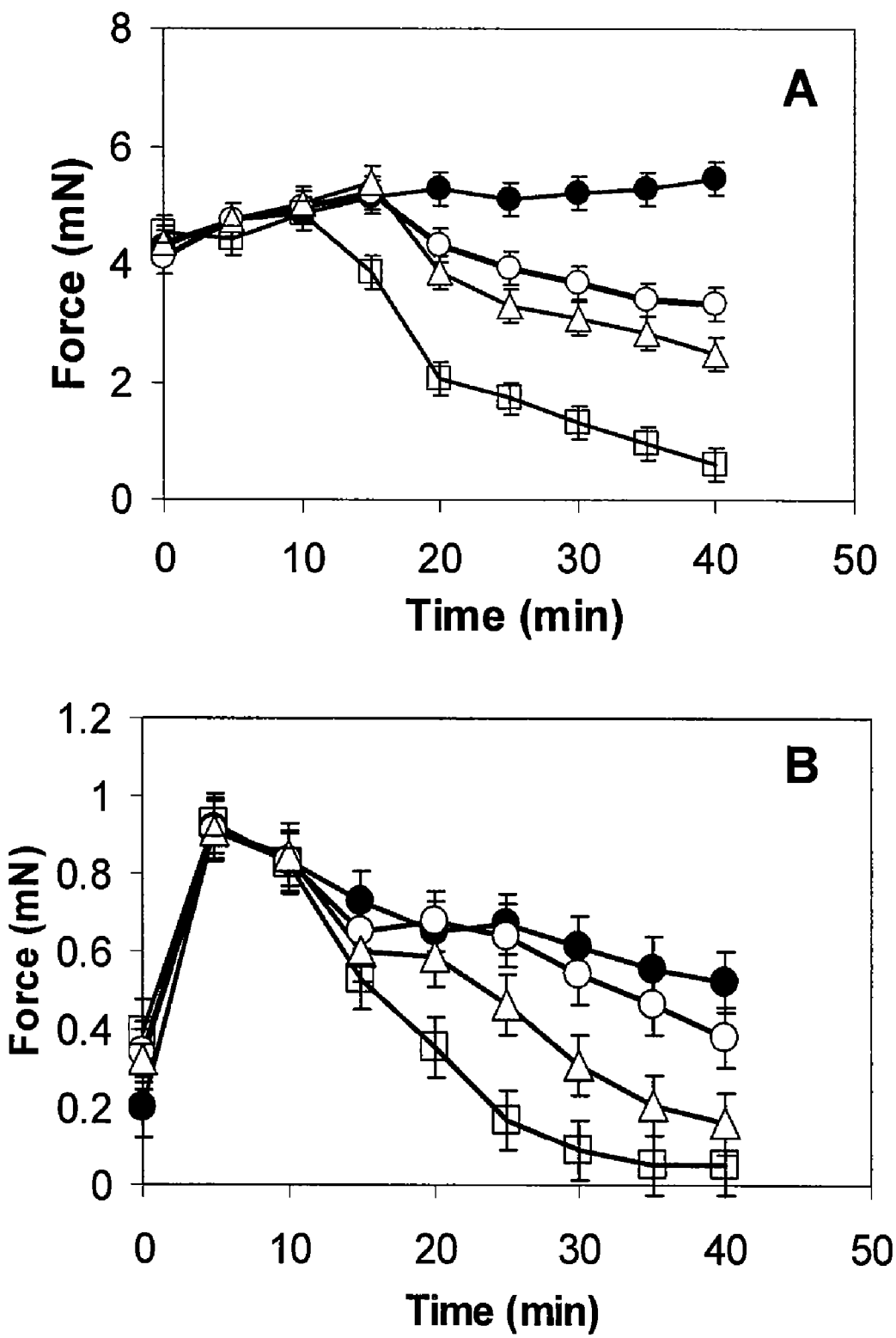
FIG. 33 is a set of graphs showing the effects of endothelin and collagenase treatment on mechanical properties of the bio-artificial tissue.

To verify the sensitivity for detecting changes in the mechanical properties of extracellular matrix (ECM) by the device, different concentrations of collagenase (1, 10, 100 U/ml) were administered to the different sets of bio-artificial tissues at time indicated by the arrow (b) in FIG. 33. All the bio-artificial tissues were treated with Endothelin-1 (50 nM, arrow a) to make sure the cells were responding to a contractile stimuli. FIG. 33B shows pre-tension data indicating that the cellular contractility was increased immediately after endothelin treatment.

FIG. 33A shows the product of elastic modulus, E, and cross sectional area A, EA, representing the tissue stiffness recorded before and after treatment with Endothelin (50 nM) and collagenase (type II) indicated by the arrows a and b, respectively. Experimental groups are separated into control (no treatment, filled circle), and treatments with 1, 10, 100 U/ml collagenase indicated by open circle, open triangle, and open square, respectively. After addition of 1 U/ml collagenase, the pre-tension, i.e. cellular contractility, was maintained compared to that of untreated control. About 10 min after the same treatment, EA began to be reduced, indicating a change in matrix stiffness and EA continued to decrease throughout the experiment. Although higher concentrations of collagenase treatment decreased both pre-tension and EA, 10 U/ml collagenase didn't reduce the pre-tension significantly for ~10 min. At the same time point, the drop of EA treated with 100 U/ml collagenase was already significant. While the collagenase digested the collagen matrix and affected ECM stiffness, the cell-ECM connection was slowly disrupted. Therefore, the cellular contractility was decreased especially with higher concentrations of collagenase. Nevertheless, the dataset indicated the measurement system sensitively detected incremental changes in ECM mechanics depending on the level of collagen degradation by the increasing concentrations of collagenase. At the 20 min time point (10 min after collagenase treatment), the apparent reduction of EA, but not pre-tension, indicates the EA was more sensitive to treatments affecting the extracellular matrix.

Example 18

Time Dependent Measurements of Acute and long Term Responses

Figure 34:
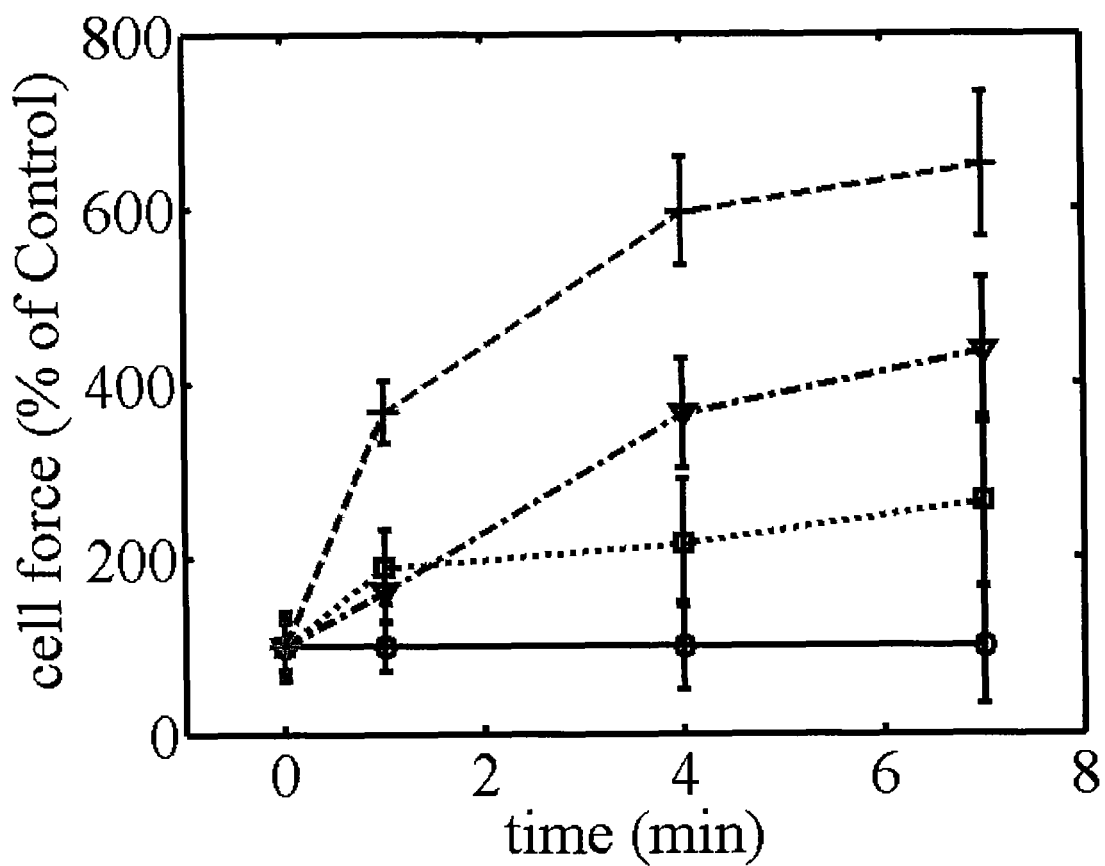
FIG. 34 is a graph showing the time progression of active force of bio-artificial tissues including smooth muscle cells from rat aorta in response to 50 nM Norepinephrine (squares), 100 NM Endothelin (triangles) and 10% Fetal Bovine Serum (plus signs). The data were normalized to Control (circles) (100%=0.49 mN). Each data point represents the average of 4 samples (bar=s.e.).
Figure 35:
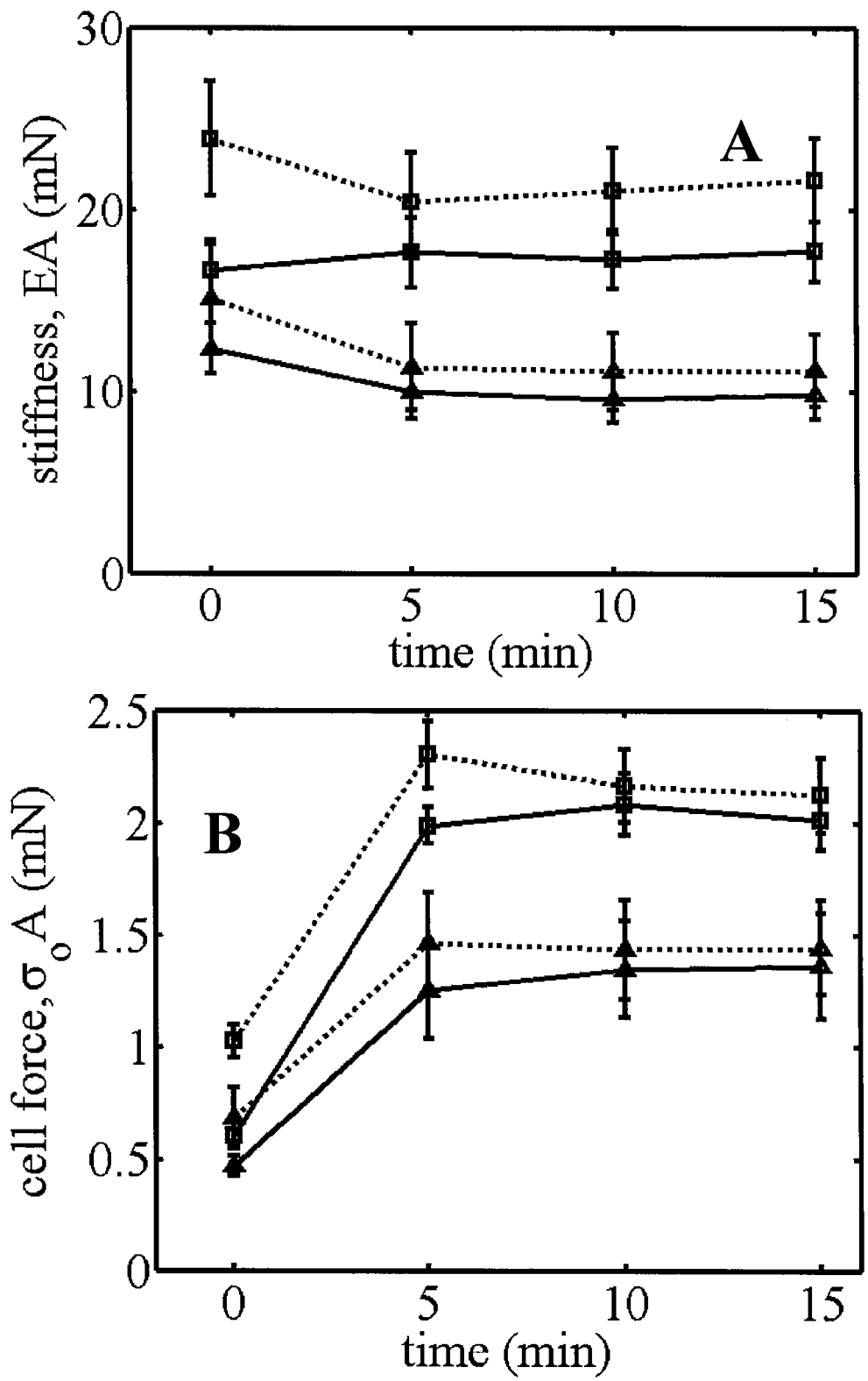
FIG. 35 is a set of graphs showing the stiffness and cell force of bio-artificial tissues including rat embryo fibroblasts measured using the same tissue sets on day 3 (squares, solid line) and day 6 (triangle, dotted line). Squares represent tissues in chambers pretreated with 10% FBS culture medium and triangles represent chambers pretreated with 5% Pluronic. Each point represents the average of 4 data points (bar=s.e.).

To test the system's ability to measure acute time-dependent response after treating the ETs, vasoconstrictors, norepinephrine and endothelin-1 and general constricting agent, fetal bovine serum (FBS) were added to bio-artificial tissues with smooth muscle cells (SMCs) isolated from rat aorta ($10^6$ SMCs per ml of bio-artificial tissue solution at bio-artificial tissue formation). The force generated by these bio-artificial tissues was measured at 0, 1, 4 and 7 min after adding the agents. In all cases, cell forces increased over time reaching their maximum value at 7 min (FIG. 34). The total acquisition time for 64 data points was 40 minutes. The consecutive indentation of the same sample reduced the time period of data collection compared to those using 64 different samples (FIG. 32).

A long-term monitoring of bio-artificial tissues mechanics was demonstrated using bio-artificial tissues including rat embryo fibroblasts. The acute force response to 20% FBS on fibroblast bio-artificial tissues was tested on the same samples on day 3 and 6 after the bio-artificial tissue formation. The time dependent response to 20% FBS was tested over a period of 15 minutes on both days. The effect of overnight treatment with 5% Pluronic F127 to induce tissue remodeling was used as an experimental condition. After preconditioning, four indentations measured bio-artificial tissue mechanics before and after FBS addition every 5 min for 15 min. At the end of the experiment, the medium was changed to DMEM with 3% FBS and incubated another three days and the experiment was repeated. The stiffness of these bio-artificial tissues did not vary appreciably after adding FBS. However, cell force increased 3 to 4 times at 5 min and was maintained with respect to that before FBS treatment. (FIG. 35A, B). The appreciable reduction of the stiffness and cell force pretreated by Pluronic pretreatment indicated a change in the remodeling rate induced by the treatment, although the mechanism by which the remodeling was regulated is unknown. Nevertheless, the experiments demonstrated that applicability of the system to detecting long-term effects of chemicals.

While the invention has been described in terms of various specific embodiments, those skilled in the art will recognize that the invention can be practiced with modifications within the spirit and scope of the claims.

All patents, publications and references cited herein are hereby fully incorporated by reference. In case of conflict between the present disclosure and incorporated patents, publications and references, the present disclosure should control.

We claim:

1. An apparatus for culturing a bio-artificial tissue, comprising:
   a multi-well plate having a plurality of wells therein;
   at least one of the wells including a scaffold formed of a non-porous material and without a fastener to facilitate tissue adhesion;
   the scaffold having at least one elongate member with a cross-sectional diameter between about 100 μm and about 2.0 mm, and disposed within the well above and substantially parallel to the bottom of the well; and
   further comprising at least one leg for supporting the scaffold above the bottom of the well.

2. The apparatus of claim 1, wherein the scaffold is at least about 0.5 mm above the bottom of the well.

3. The apparatus of claim 1, wherein the scaffold is at least about 1.0 mm above the bottom of the well.

4. The apparatus of claim 1, wherein the scaffold is metal.

5. The apparatus of claim 1, wherein the scaffold is plastic.

6. The apparatus of claim 1, wherein the member is tubular.

7. The apparatus of claim 1, wherein the member has a cross-sectional diameter of about 1.0 mm.

8. The apparatus of claim 1, wherein the scaffold is circular.

9. The apparatus of claim 1, wherein the scaffold includes two parallel, spaced apart members.

10. The apparatus of claim 1, wherein the scaffold is triangular.

11. The apparatus of claim 1, wherein the scaffold is supported by the side of the well.

12. The apparatus of claim 1, wherein the scaffold is attached to the side of the well.

13. An apparatus for culturing a bio-artificial tissue, comprising:
    a multi-well plate having a plurality of wells therein;
    at least one of the wells including a scaffold formed of a non-porous material and without a fastener to facilitate tissue adhesion;
    the scaffold having at least two parallel, spaced apart members, each positioned within the well and disposed above and substantially parallel to the bottom of the well; and
    further comprising at least one leg for supporting the scaffold above the bottom of the well.

14. The apparatus of claim 13, wherein the scaffold is at least about 0.5 mm above the bottom of the well.

15. The apparatus of claim 13, wherein the scaffold is at least about 1.0 mm above the bottom of the well.

16. The apparatus of claim 13, wherein the scaffold is metal.

17. The apparatus of claim 13, wherein the scaffold is plastic.

18. The apparatus of claim 13, wherein the members are tubular.

19. The apparatus of claim 13, wherein the members have cross-sectional diameters of about 1.0 mm.

20. The apparatus of claim 13, wherein the scaffold is supported by the side of the well.

21. The apparatus of claim 13, wherein the scaffold is attached to the side of the well.

22. An apparatus for culturing a bio-artificial tissue, comprising:
a multi-well plate having a plurality of wells therein;
at least one of the wells including a scaffold formed of a non-porous material and without a fastener to facilitate tissue adhesion;
the scaffold having at least one elongate member, and disposed within the well above and substantially parallel to the bottom of the well; and further comprising at least one leg for supporting the scaffold above the bottom of the well.

23. The apparatus of claim 22, wherein the scaffold supports tissue adhesion of the bio-artificial tissue and suspends the tissue above the bottom of the well.

24. The apparatus of claim 13, wherein the scaffold supports tissue adhesion of the bio-artificial tissue and suspends the tissue above the bottom of the well.

* * * * *